(12) United States Patent
Schnable et al.

(10) Patent No.: US 8,779,233 B1
(45) Date of Patent: Jul. 15, 2014

(54) QTL REGULATING EAR PRODUCTIVITY TRAITS IN MAIZE

(75) Inventors: Patrick S. Schnable, Ames, IA (US); Jinliang Yang, Ames, IA (US); Ruth A. Swanson-Wagner, The Hague (NL); Dan Nettleton, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 105 days.

(21) Appl. No.: 13/180,986

(22) Filed: Jul. 12, 2011

Related U.S. Application Data

(60) Provisional application No. 61/364,104, filed on Jul. 14, 2010.

(51) Int. Cl.
*A01H 1/04* (2006.01)

(52) U.S. Cl.
USPC .......................................... 800/267; 800/275

(58) Field of Classification Search
None
See application file for complete search history.

(56) References Cited

U.S. PATENT DOCUMENTS

| | | | |
|---|---|---|---|
| 7,250,552 B2 | 7/2007 | Han et al. | |
| 7,423,207 B1 * | 9/2008 | Vosseller | 800/320.1 |
| 2008/0227091 A1 | 9/2008 | Han et al. | |

OTHER PUBLICATIONS

Veldboom et al. Theor Appl Genet 88: 7-16, 1994.*
Bommert et al., "Thick Tassel Dwarf1 Encodes a Putative Maize Ortholog of the *Arabidopsis* CLAVATA1 Leucine-Rich Repeat Receptro-Like Kinase," Develop. 132(6):1235-1245 (2005).
Tang et al., "Dissection of the Genetic Basis of Heterosis in an Elite Maize Hybrid by QTL Mapping in an Immortalized F(2) Population," Theor. Appl. Genet. 120:333-340 (2010).
Austin et al., "Comparative Mapping in F(2:3) and F(6:7) Generations of Quantitative Trait Loci for Grain Yield and Yield Components in Maize," Theor. Appl. Genet. 92:817-826 (1996).
Veldboom et al., "Genetic Mapping of Quantitative Trait Loci in Maize in Stress and Nonstress Environments: I. Grain Yield and Yield Components," Crop Science 36:1310-1319 (1996).
Veldboom et al., "Genetic Mapping of Quantitative Trait Loci in Maize in Stress and Nonstress Environments: II. Plant Height and Flowering," Crop Science 36:1320-1327 (1996).
Veldboom et al., "Molecular Marker-Facilitated Studies in an Elite Maize Population: I. Linkage Analysis and Determination of QTL for Morphological Traits," Theor. Appl. Genet. 88:7-16 (1994).
Beavis et al., "Identification of Quantitative Trait Loci Using a Small Sample of Topcrossed and F(4) Progeny from Maize," Crop Science 34:882-896 (1994).
Swanson-Wagner, "Differential Regulation of Transcript Accumulation in Inbred and Hybrid Maize," Ph.D. Final Defense Seminar, Iowa State University, Jul. 14, 2009.
Liu et al., "High-Throughput Genetic Mapping of Mutants via Quantitative Single Nucleotide Polymorphism Typing," Genet. 184:19-26 (2010).
Liu et al., "Mu Transposon Insertion Sites and Meiotic Recombination Events Co-Localize with Epigenetic Marks for Open Chromatin Across the Maize Genome," PLOS Genet. 5(11):1-13 (2009).
Swanson-Wagner, "Analysis of Differences in Gene Expression and the Genetic Regulation of Transcript Accumulation in Maize Inbred and Hybrid Lines," Ph.D. dissertation, Iowa State University, Oct. 15, 2009.

* cited by examiner

*Primary Examiner* — Shubo (Joe) Zhou
*Assistant Examiner* — Keith Robinson
(74) *Attorney, Agent, or Firm* — LeClairRyan, A Professional Corporation

(57) ABSTRACT

The present invention relates to a method for determining an ear productivity trait in maize, which involves analyzing genomic DNA from a maize plant, germplasm, pollen, or seed for the presence of a molecular marker linked to a QTL associated with an ear productivity trait in maize. Also disclosed are methods of selecting a maize plant with a desired ear productivity trait; reliably and predictably introgressing an improved ear productivity trait into a maize line; and producing a maize line having a desired ear productivity trait. A kit for selecting a maize plant by marker assisted selection of a QTL associated with a desired ear productivity trait; an isolated nucleic acid comprising a QTL associated with an ear productivity trait in maize; and a transgenic plant comprising a recombinant nucleic acid genetically linked to a locus in maize, are also disclosed.

16 Claims, 31 Drawing Sheets

| Marker | SNP Context Seq | SEQ ID NO: |
|---|---|---|
| SNP_35511 | CGGCTGGCTCAACGAGTGACTTTTTTTTGCGTCTGTATACCTATGTATGTATCTGTCATG[G/C]TAC AAGTTCGCTATATGCTGATTTAATAATAAGAGAGAACTTACTAGTAGACTATTGTAT | SEQ ID NO:1 |
| SNP_98111 | AGGCTACAAACACAAGAACCACAACATCTGCGTGCGTAGGCAGAGACTCAAAAGGCCAGC[C/T]CTG TATGAAAATTCTAATGATACAATCCTTCAAGGTGATCGACGAAGGTATATTCCGTTT | SEQ ID NO:2 |
| SNP_23951 | GGATAGCTGCTGCTTCGCAGGCAGTGCGTCCACATGAAGCCTACATTCAGAGCCATCACA[T/G]GCC TATGCAAGCTTCTGCCCACAACAATCTCCTGTTGTCAATCTGATACTTTTGAGCACG | SEQ ID NO:3 |
| SNP_79262 | GGTTTCTGTGTTTTTATGTCAAGACCTCACGCATATCGCGCGGAGTAGCTAAGCTCCACC[G/A]TAT ATTGCTTGCGACGTATGATCCTTGTTTTATTTAAGTGTGTTGGCGTTTTATC | SEQ ID NO:4 |
| SNP_19249 | TGCCTTGATACATTGTTACAGAGAAACAAAATCAAAAACTTAAGAATGTCCGATACATCT[T/G]CTG TGAATGCACAATACAGTCACACGGCCACTTTTATAAAAGGAAAACGGACCTATCGCC | SEQ ID NO:5 |
| SNP_0984 | TTGATGATGGTAATATGTATTCTCAGACTCGACACATGTGTGCAACTCATTTAACACACC[G/A]CCA CAGGAAGGTAAGCTTCGCAATCCGATAGAGGGATGCTTACAAATAGCCTAAATCAT | SEQ ID NO:6 |
| SNP_99055 | TTTGTCCGTCCTTGTTTCTTTTCTTTTTTCCAGTCGAGAGAGAGACAGAGCTGGCTAAAGA[T/C]CAG GGAGAAGCTGGCACGTAATAGGGTCGATAGTTAAGCATGATCATCCTGTGTATTTGC | SEQ ID NO:7 |
| SNP_77055 | TTGTATCGGTTTGTTCAGAGTTTTACGGTGTGGGAACATTAGTAGAAATGTCATTTCACT[G/T]CCT TCTTTTCCCCGCTGGATCGCATTTCACAAAATATTTCCACCATTCTTGCAGAGAAGC | SEQ ID NO:8 |
| SNP_45551 | TTTATCTTACAGAAATACATACCTCAATCATCGGTCTCTCCA[T/G]GCAAAAAGATAACGAAACAAA CCTAGACTAATGAGCTGAAGACCAGTATAAAATAGGTCG | SEQ ID NO:9 |
| SNP_30953 | CCCATCATCAGATATCTAGATCGAAGCGGGGGTCCGAAGGCAATTCATGAATGGAGTGAC[A/G]ACG ATAGGCAAGCTAGTACAAACTTTTGATCCATCAGCCATGCACGGCATGGAACGGAACA | SEQ ID NO:10 |
| SNP_84678 | TGGTGATTCTGTCTGGTTGATATTTGCTACTGATATTGGTCCCATTTGAGATATGCGTTG[C/A]TGC TAGTCTCGTCTTTCTCTGCGCTTGATTTATCGTTATACATCGCTCCATCGCTCGCTG | SEQ ID NO:11 |
| SNP_89298_2 | GGGATGTCTTACTGCAGGGTACGGCTGTTGAAAGGATGCCACAGGTTATGTACAGAAGAC[C/A]GCA CACCAGGTTGACGCCAGGAACCCATGTGCGCAAAATGTCATGCCTTGCACCGCACCA | SEQ ID NO:12 |
| SNP_32823 | ACCAATTAATTTCTGCAAAGTGAGTAATTCGTCTACAGCTTCATGTGAGGAAGAGCTGTT[G/C]AAC AGCGCCCTGAAGGACGAATATGGCATAACCAGAGTATTCGCCTACAGCTTCAAGTAA | SEQ ID NO:13 |
| SNP_4623 | ATTTATGTTCATTTCTTCTTTTCTTAAAGAAGCATGCACTAAGAACATGAAGGATGCATG[C/T]CAT GGAAAGTTTTTGAAAGTCATTGAAACGTATGAGCTCCTCATGCAATGCATTATTCTC | SEQ ID NO:14 |
| SNP_90941 | GTTTTCCTGTACTAAGTATATTGTATATTATTCCAGCAGCGATGTGATCTTCAAATTCAT[C/T]GTG ATGTATTCGACACCACGCTAAAGGATGGTCTGAGCAAACTTTCTTCAGCTCCTCAAT | SEQ ID NO:15 |
| SNP_81248 | GAAGGGATGTGATGTGTATCTCTTAGGCTAGACTGCTTCAGCTAGTTTTCTGTGACTGCT[A/T]CAT GAATCCATGGATTACTGATTTACTGGGCTTGTGCTTTGTATGATGCTGCCATCTG | SEQ ID NO:16 |
| SNP_82913 | GCTGTGAGCATTCGTTTGTAGGAAAAGTGAGAACGGATGTGTATCAATCCGTGTTGGGTG[A/C]CGA TGACTCACGGATGAATCAAATATTTCCGTATATTGCGGCCAAAACAGTTCTATCTCA | SEQ ID NO:17 |
| SNP_93907 | TATTCATCCTGCTTCATGTGTAGCTTTCATGGAAATTGTGTATGTAACCCAAATCATGGG[C/T]GCA TTACAGACCTAACGGAAAAAAGTCAGTGCTGCGCCTTTAGAATGCAGCTTGCTCTCT | SEQ ID NO:18 |
| SNP_90380 | AACCTGGTCAGTACTACTTTTAGCACAAACTTTTAGCCGCGTGGAACACTCTTCCACAGCAC[T/C]ACC ACCGCCACATCGCAAACACTAATTTACGATCCGCGAAATCTACCCCAAGGTGGCACA | SEQ ID NO:19 |
| SNP_49724 | TGAGTTATTCTCAGGCTGCGCCACAGAACCATCGATGGAAGTACCCAGCAT[C/T]GTTACGCGCTCA AAACCAAGCACCCACACACAAATGCTACCGGTAAACGGCCAATGCCCT | SEQ ID NO:20 |
| SNP_51496 | GATTTTTTGTTCCACAATTGTTATCTGTAACAAGAACATCTACATCTGTGATGACTCACC[A/G]TTA ATAAATGTGTCCCGGTGTACCATTTGTTTTTTTCTTTGAGCACTGGCAGTAGCAGG | SEQ ID NO:21 |
| SNP_11948 | CTCTGTGTATCTACCATCTTGGGATGTACTGAATTGAGTTTGGGACGTGTATCTACCTAC[C/G]ATC TTGTATTGTCAGCTCAAGGATGTAGCAAACTAGTAGCAACTTCAAAAAATGAGATGT | SEQ ID NO:22 |
| SNP_18689 | CCCCATAGCAAAGACCGCCTTTCCACCACGTGATATTTCAACAGCCCAACGATTTCTTAC[A/T]CAG TAATTAAGCATATTCCAGTGAAAATCCAAAGCGACATTTGTGTTAACCAAGCGAATG | SEQ ID NO:23 |
| SNP_61221 | ATTACATCAACGAGGGCATTAACAAATCAATCGACTTAAATTTCGTTTCCCCAATGATGC[G/A]ACT TCCAAAGTTCAGCTGTCACATTTCATTTAGATGGACTAAGCTACTGCAGATAATCTA | SEQ ID NO:24 |

Figure 3A

| Marker | SNP Context Seq | SEQ ID NO: |
|---|---|---|
| SNP_105143 | AAACTGAGTGCTAAATTTTGTTTCTTGTTACTAACCGTTAAGAATCACGAGATGGTTAAT[G/A]ATG GTTGAGCTTGTCCAGAAAACATGGATAAGTGAGGTCTCAAAAAATGTAGCATCTTTT | SEQ ID NO:25 |
| SNP_84372 | AAGTTGACTTGGCTAAGGTCTATTGATTAGATGGATTAAGAGAAGTGTTTCGGCTGCCGA[G/A]GTC GTAATATTATGATTCAACATATAAGTACTAATAATCAGTGGGCAAAGCTTCGTTACT | SEQ ID NO:26 |
| SNP_27764 | AAACCACATAGTAGTAGTAGAAGTACATGGTAAAGGACGATGGAACATATATATGACACT[C/G]TTG ATAGATCTAACAGATGTTCAACTTGTTCTCCATGGTAAAAACATGTTGTTCAGCACA | SEQ ID NO:27 |
| SNP_95039 | AATTTCGAAGTTCTAAACATCTATTGCCGGGATAAAAATTCTCCATATGAATCTCCTCCC[T/G]AAT TCGAGCTTCAGAACACCTAGATAAAAGAGGGATTAGACCCTATGCCAGACAAAGCTCT | SEQ ID NO:28 |
| SNP_75795 | GCTTGTTCAAGAGAACGCTGGTAACATGTTTGCTATATATCTGGGGAGTCCATTTCGTAG[C/T]GAG GAATGATTACACGGCACCATTCTTATCGTCTTATCCAACCACGGGCTCATGTATATT | SEQ ID NO:29 |
| SNP_70805 | AATAATCCAAACAGTATACGGCCCAACCGAGTAACCTCATACAAGAACCTAAAGAGAGAG[G/A]AAA AAACCGCGGATCCAACAACCAATTACACCGTCCCTACTAAGGTAATGTTAAAAAGAA | SEQ ID NO:30 |
| SNP_43846 | AGTACTAGTATAAGCACATCATAATAATATATAGTATATATAGGAGGAGTCCATACATAA[C/T]TAT GGCATATATATGCAGTACGCACACTACAGTCCAGCAGGCCGGCGGTACGACGGTAGG | SEQ ID NO:31 |
| SNP_98032 | TTGGCTTCGTTCGTGCTTTTGCTATATGGTGTAGCGTCCTTGCCTGTAAAGAAATCCCAT[A/G]TCA CCAGAAGAATTTGAGACGTCAACAGTCATCAAGTACTATAAAATTTAGATGCCTTTT | SEQ ID NO:32 |
| SNP_63437 | ACGCTTGTTGTACCATGCAGCCTCTTGTTGATGTATGTTGGCACTCGTTTGTTTCTCCAA[G/T]GCA CGTGTTCGGTAACAGTATATAGATGGCTACCTGTGCGTATGTTGGCGCACTTCATGC | SEQ ID NO:33 |
| SNP_94161 | CGCGATTCCGTCACCGAACAAACAAACAAACAAACAACAAACCCCTCCGCGGCCACTCATC[T/A]TCA GTCCAAAACGACACTTCCACCCCGGCAACAGTCAAGCTCACTTTCCGCGAGCAGGAG | SEQ ID NO:34 |
| SNP_34738 | ATTGTTTTTCATTGCGAACACTCTAGTAGGCCATTTATCTACGGTTTTTCACTATATT[C/T]ATT AAGATATTATGAGATTTCACATTGCCTTGTAAAGACAAATCTCTAGCCATGTTTGGT | SEQ ID NO:35 |
| SNP_88270 | ATTCACGACCCATTTAATCAGGAACCACGCACAATGTGTATATCATAAATAGAAATCCCC[A/G]ATT GCAGATAACAATTGTGGAATAGAAACGTAATACAAAAGGTAGATTTTAGAAAGGACA | SEQ ID NO:36 |
| SNP_2880 | CGTTCAAGTGAGATATTCAATTGTTCAGATATTCAAATTCTTTGAAAAACTCAGCACAAA[C/T]ATT CAAATGTTCAGATATTCAAATTCTTCGAAAATGTTCAGACTTTAGACAAAAAGTAAC | SEQ ID NO:37 |
| SNP_36300 | CCACCTCCGAAGATACTGTAGATTCCTATGATCATTTGGCTGCATTGTTCCGGCCACCTG[A/T]CGC CGTCTCGCCGGTTGGAGCAGCAGGACCAAATTCCCTTGCGTGGCTCCTGCTCTTTGC | SEQ ID NO:38 |
| SNP_77712 | AGAAATGTTCATTGTCATATTGGGCATCCATCCACAGGCACAGTTCAGCGGGATTTTAAG[T/G]CTG AGTTCATCGCTTTTTCAACCCGTCCGAAGCTACCAACATCAGAGCGGTAGGGGAGGC | SEQ ID NO:39 |

Figure 3B

| Marker | Forward primer Seq | SEQ ID NO: | Reverse primer seq | SEQ ID NO: |
|---|---|---|---|---|
| SNP_35511 | ACGTTGGATGGTCTACTAGTAAGTTCTCTC | SEQ ID NO:40 | ACGTTGGATGGCGTCTGTATACCTATGTATG | SEQ ID NO:79 |
| SNP_98111 | ACGTTGGATGCGTAGGCAGAGACTCAAAAG | SEQ ID NO:41 | ACGTTGGATGTACCTTCGTCGATCACCTTG | SEQ ID NO:80 |
| SNP_23951 | ACGTTGGATGCAACAGGAGATTGTTGTGGG | SEQ ID NO:42 | ACGTTGGATGTGAAGCCTACATTCAGAGCC | SEQ ID NO:81 |
| SNP_79262 | ACGTTGGATGCAAGGATCATACGTCGCAAC | SEQ ID NO:43 | ACGTTGGATGGTCAAGACCTCACGCATATC | SEQ ID NO:82 |
| SNP_19249 | ACGTTGGATGGCCTTGATACATTGTTACAG | SEQ ID NO:44 | ACGTTGGATGTAAAAGTGGCCGTGTGACTG | SEQ ID NO:83 |
| SNP_0984 | ACGTTGGATGACTCGACACATGTGTGCAAC | SEQ ID NO:45 | ACGTTGGATGTGTAAGCATCCCTCTATCGG | SEQ ID NO:84 |
| SNP_99055 | ACGTTGGATGTATCGACCCTATTACGTGCC | SEQ ID NO:46 | ACGTTGGATGGTGCGTCCTTGTTTCTTTTC | SEQ ID NO:85 |
| SNP_77055 | ACGTTGGATGTTGTGAAATGCGATCCAGCG | SEQ ID NO:47 | ACGTTGGATCTCAGAGTTTTACCGTGTGGG | SEQ ID NO:86 |
| SNP_45551 | ACGTTGGATGACATACCTCAATCATCGGTC | SEQ ID NO:48 | ACGTTGGATGACTGGTCTTCAGCTCATTAG | SEQ ID NO:87 |
| SNP_30953 | ACGTTGGATGCATGGCTGATGGATCAAAAG | SEQ ID NO:49 | ACGTTGGATGGATATCTAGATCGAAGCGGG | SEQ ID NO:88 |
| SNP_84678 | ACGTTGGATGGCGATGGAGCGATGTATAAC | SEQ ID NO:50 | ACGTTGGATGTTGCTACTGATATTGGTCCC | SEQ ID NO:89 |
| SNP_89298_2 | ACGTTGGATGTGTTGAAAGGATGCCACAGG | SEQ ID NO:51 | ACGTTGGATGTGACATTTTGCGCACATGGG | SEQ ID NO:90 |
| SNP_32823 | ACGTTGGATGTCTGCAAAGTGAGTAATTCG | SEQ ID NO:52 | ACGTTGGATGGCGAATACTCTGGTTATGCC | SEQ ID NO:91 |
| SNP_4623 | ACGTTGGATGTTGCATGAGGAGCTCATACG | SEQ ID NO:53 | ACGTTGGATGGCATGCACTAAGAACATGAAG | SEQ ID NO:92 |
| SNP_90941 | ACGTTGGATGATTATTCCAGCAGCCATGTG | SEQ ID NO:54 | ACGTTGGATGTCAGACCATCCTTTAGCGTG | SEQ ID NO:93 |
| SNP_81248 | ACGTTGGATGGTGATGTGTATCTCTTAGGC | SEQ ID NO:55 | ACGTTGGATGGCACAAGCCCAGTAAATCAG | SEQ ID NO:94 |
| SNP_82913 | ACGTTGGATGGTTTTGGCCCCAATATACGC | SEQ ID NO:56 | ACGTTGGATGCGGATGTGTATCAATCCGTG | SEQ ID NO:95 |
| SNP_93907 | ACGTTGGATGGCAGCACTGACTTTTTTCCG | SEQ ID NO:57 | ACGTTGGATGCTGCTTCATGTGTAGCTTTC | SEQ ID NO:96 |
| SNP_90380 | ACGTTGGATGCACAAACTTTTAGCCGCGTG | SEQ ID NO:58 | ACGTTGGATGTCGCCGATCGTAAATTAGTG | SEQ ID NO:97 |
| SNP_49724 | ACGTTGGATGTGAGTTATTCTCAGGCTGCG | SEQ ID NO:59 | ACGTTGGATGTGTGGGTGCTTCGTTTTGAG | SEQ ID NO:98 |
| SNP_51496 | ACGTTGGATGAACAAATGGTACACCGGGAC | SEQ ID NO:60 | ACGTTGGATGCAAGAACATCTACATCTGTG | SEQ ID NO:99 |
| SNP_11948 | ACGTTGGATGTGCTACATCCTTGAGCTGAC | SEQ ID NO:61 | ACGTTGGATGACTGAATTGAGTTTGGGACG | SEQ ID NO:100 |
| SNP_18689 | ACGTTGGATGATAGCAAAGACCGCCTTTCC | SEQ ID NO:62 | ACGTTGGATGTCGCTTTGGATTTTCACTGG | SEQ ID NO:101 |
| SNP_61221 | ACGTTGGATGCGACTTAAATTTCGTTTCCCC | SEQ ID NO:63 | ACGTTGGATGCTGCAGTAGCTTAGTCCATC | SEQ ID NO:102 |

Figure 4A

| Marker | Forward primer Seq | SEQ ID NO: | Reverse primer seq | SEQ ID NO: |
|---|---|---|---|---|
| SNP_105143 | ACGTTGGATGCCGTTAACAATCACGACATG | SEQ ID NO:64 | ACGTTGGATGCAGACCTCACTTATCCATCT | SEQ ID NO:103 |
| SNP_84372 | ACCTTCGATGGATTAAGAGAAGTCTTTGGCC | SEQ ID NO:65 | ACGTTGGATGTAACGAAGCTTTCCCCACTG | SEQ ID NO:104 |
| SNP_27764 | ACGTTGGATGGGAGAACAAGTTGAACATCTG | SEQ ID NO:66 | ACGTTGGATGGAAGTACATGGTAAAGGACG | SEQ ID NO:105 |
| SNP_95039 | ACGTTGGATGGCCGGGATAAAAATTCTCCA | SEQ ID NO:67 | ACGTTGGATGTGGCATAGGTCTAATCCCTC | SEQ ID NO:106 |
| SNP_75795 | ACGTTGGATGCTTGTTGAAGAGAACGCTGG | SEQ ID NO:68 | ACGTTGGATGACGATAAGAATGGTGCCGTG | SEQ ID NO:107 |
| SNP_70805 | ACCTTCGATGCCAACCGAGTAACCTCATAC | SEQ ID NO:69 | ACGTTGGATGAGTAGGCACCGTCTAATTGG | SEQ ID NO:108 |
| SNP_43846 | ACGTTGGATGAGTATATATAGGAGGAGTGC | SEQ ID NO:70 | ACGTTGGATGGGACTGTAGTGTGCGTACTG | SEQ ID NO:109 |
| SNP_98032 | ACGTTGGATGTGCTATATGGTGTAGCGTCC | SEQ ID NO:71 | ACGTTGGATGGTACTTGATGACTGTTGACG | SEQ ID NO:110 |
| SNP_63437 | ACGTTGGATGTACCATGCAGCCTCTTGTTG | SEQ ID NO:72 | ACGTTGGATGCGCACAGGTAGCCATCTATA | SEQ ID NO:111 |
| SNP_94161 | ACGTTGGATGAAACAACAAACCCCTCCGC | SEQ ID NO:73 | ACGTTGGATGAAGTGAGCTTGACTGTTGCC | SEQ ID NO:112 |
| SNP_34738 | ACCTTCGATGACTACGCCATTTATCTACGG | SEQ ID NO:74 | ACGTTGGATGCAGATTTGTCTTTACAAGCC | SEQ ID NO:113 |
| SNP_88270 | ACGTTGGATGATCAGGAACCACGCACAATG | SEQ ID NO:75 | ACGTTGGATGGTATTACGTTTCTATTCCAC | SEQ ID NO:114 |
| SNP_2880 | ACGTTGGATGCAAATTCTTTGAAAAACTCAG | SEQ ID NO:76 | ACGTTGGATGGTTACTTTTTGTCTAAAGTC | SEQ ID NO:115 |
| SNP_36300 | ACGTTGGATGCATTTGGCTGCATTGTTCCG | SEQ ID NO:77 | ACGTTGGATGAAGGGAATTTGGTCCTGCTG | SEQ ID NO:116 |
| SNP_77712 | ACGTTGGATGCTTCGGACGGGTTGAAAAAG | SEQ ID NO:78 | ACGTTGGATGGTCATATTGGGCATCCATCC | SEQ ID NO:117 |

Figure 4B

| Marker Name | Context Seq | SEQ ID NO: |
|---|---|---|
| PZA01216.1 | GGTATGTTCATTTTGCTATATTTATGGTGAACCGTTGAATGTGACTGGGATAATGATGT[C/T]AGAAA AGGCATTGAAACTTCTCATCGGTGCCCATCCAGTTAATTTCTACGACCGTAAAAAAATAACCCACTGCA ACTGTTTTACAAGAAGTATTCATGTG | SEQ ID NO:118 |
| PZA01497.1 | ATACGTATACCGGAGATGAAAGGAGACGGAGGCAGTGAAGAAATATCCTTTTTTTTCTTCTCRTTTTTC ACGAGGATGCSGTGCACTGCTCCCAGAATGCTGTGTCCAATTTACAAACGCACAGGTGGCACATGAACT AGCAGAGTAGCT[C/T]TMTCTTGAAAGGAAACTGTATTTGGGGTCGATGAACCCTCTGGTGTTATTCT TCAGACKGGTAAACGATKTAAC | SEQ ID NO:119 |
| PZB00183.4 | GCTCCAGTTCATCAGSCGGTGSGACTGCCGATGCCTACCCARATAGCTCCTACTAGAGACGTCAGCTTC GTCGGC[A/G]GCGAAGGCGTCCGAATGCCCGACGCCGCAGGAGGCGACCAGACCGGGACCAGGCGC CCTCTCTGCCGGTCCAGCTGCTCGAAGCCTCCGACGCYGACGGAGCAAGCAGAGCWTCTCGCCTGTGGT TCCGASGCTGCTGGAAGRCGTCGTGCTGGCGAGCGCCRTTGTTGGTTCTACGCGCAGCTGGCGGGGCTT CGGCTCKKGGGTGGAGATGGAGATGCGCGTGGAACGGAACCTGCGCCCTGGTGTCCTCCTCCTC--- GCTGTTCGCTACTRCTAGATCGGCGGAGACCTCTGTTCCAGCTCTGTTC | SEQ ID NO:120 |
| PZA02450.1 | GACCTACTCATCATTTTCCTGAACATTTTCCAGAACGGTAACTTGTACATTATGTCTACTGCTGCCATT TTTTAATGAGCCCAGGTATCTGACAAAAGTGAAATGTCAAATATCAGGTCAAGGCAAGGAGAAAGAAAA GGTGGAGAAACTGCATAT[G/T]TTTCAAACCATAAACGTGACAGAGCCTAACGAMACGTTCATTACTGA CCTCRACACCRTTAGGCCCTATTTTGTTGCGGGATATGAACTTC | SEQ ID NO:121 |
| PZA01993.7 | TTGCAATCTCATATCTTGAATCTCACACCAAGCATAATAATTCACATTGAAAG[C/T]GTCTGACCTAT CCTCTAGCAGTTGTCGACAAATTTSTCCAGTT- CATGTACAGTAGAAACCGATGCGTTGCAGTYTCAGAACATCTTCACTTC---AGATA | SEQ ID NO:122 |
| PZA03142.5 | AGTGCCCGCGCTTGATGTCCGGGCGCAGGTAGTTGGTCCACCGCAGCCGGCAGCTCTTRCCGCACCGGT TCAGCCCTGCATGCATGC-----------------------------CCRCR--- RGTCGCTYAAGAAATGACGAGCACG------ AGGCRAACAACTAGGTCACGCATGCAGCACCAGGMRGC- CGGGC[C/T]GGGCTCGACCGAGGAACAGAGCAC--ACGTA---- CGTACCCGCGAGCTTGGGGAGCATGCGCCAATTTCCGGCRCCGTTGGCCTGGACGTAGTCGACGAGCAG CTTGTCCTCCTCCAGCGCCCACTGTCCCTTCTTGATCCCMTTGCTGTSGCAGCACGGASTTCTYCCCAT GGCGRTCGGTCGCTCTC-----CGTC | SEQ ID NO:123 |
| zb21.1 | CTACAAAGTGACCAACCATTTCATCGAATTGCTTCAAACCCGAGAGCCGCAAGATAATAGACGAACGAT CAGCTCCAGCCACCTGTAAGTACAATCACAAA[C/T]RGTAAGAGCAATGGATCACTYGTG-------- ----GAGGCTTGTGTTTACAAATAATRGCCAACAACAKGTTACCTCN-NNNATCCTCAAATAATGG-CC | SEQ ID NO:124 |
| PZA00210.1 | TCCCTTAGGAAGTATCTACATCAGCAGGAGCCTCACTCAGTTCCCCTCAACMTAGTGCTGAAATTAGCT CTAGATATYGCTCGYGGAATGAGCTACCTACACTCCCAGGGTATACTCCATAGRGACCTGAAATCAGAG AACRTACTTCTGGGAGAAGATATGTCAGTCAAAGTYGCAGATTTCGGGATTTCATGCTTGGAATCACAG TGTGGAAGTGGCAAGGGGTTTACAGGAACCTACAGGTGGATGGCTCC[A/G]GAGATGATCAAAGAGGA ACATCATACTAGGAAAGTGGACGTGTACAGC | SEQ ID NO:125 |
| PZA02427.1 | CMATGGTACACGTAACCCGGACCMGTGGTGACGTCGAAGGGGAMGCGGSTCTCCTCCGGCGACGCGGCG TCTGTGAGCGGCTTCAAGCCCACCAGGATCC[G/T]GGTTACCGCGCTGGGCCGCACCTTGAAGACGTT CTTCCAGCCGCGCTCCTGCCGCGGCACGACGTGCCTCCGCSMCCCGCCCAGGTGGCCGTCGACCCCGCA CGCGCCGCGTCGTTCCGGCGCTTCATGCAGTCCCTGAASTCGTCCA | SEQ ID NO:126 |

Figure 5A

| Marker Name | Context Seq | SEQ ID NO: |
|---|---|---|
| PZA02585.2 | CTTCCTGATCTTCTTGGCRGTCGTGCAATTCCCCATGCTGTTCTGGCTCGGCAACATATGTGGCTGACC TTTGATCCTATTGGTCGGGCCACAGACCTGTTTCTTCTTCTTCAGAATAGGCATGTGCTACTTCTG GCTTGSTGATGAA[A/T]CTTAGGTTTATCGTGGAGATGGTACAGAACTATTAGCTATAGATATCTGGG CAATCGAAAACTGTTTTTGTTTCTGTTAGCTATAKAGGCGAAA | SEQ ID NO:127 |
| PHM2100.21 | GAAGGGGGGGGCCCGGAGNAAATTWCTYYCCSSSSGGGWAWWWAWCWWWAWARARADHHHHMMMVRNVS CRRRRRDRRMHMHNVBSNDRDDNNBNNNNNHWWADDNBSSCC------TTTTT-------GB-BTK- G-SCYWW-TYY--M--CC-Y-H---A-A-W-C--AG---AW-W-TW-M-CY--SKH-HBGRYYYDWY- YH-WAM--AWWT-TTTT---WAAAA-TKAGKT--A-CG-AWA-RRGG-----YYYW-AADAWKGC- DTWACCMGTYTWAAAA--AS-GTCMGAAYCMY-TCC-M-GGCCYTT-BG-GAAMMMCKRG- GTAAAAGGTTYRAAYCGRKGCBNADATWA--ATT--CAHGATCRNAWVAA--NRKKWT----TACTTTK-- TMRRKSMRBGC-TAHTYGTYMA-GTCMGRGRA-TGACAGBTH-SHWHCCAATY-- GCAWMATCTKGTTYTRKGGDG--AYGTYGYKCTGAWRTRT--CTGCCCKCTTCT- CGACAGATAGTAGAGGAAGCTGGTGGGGTGGTAACTCGCATGGAYGGTGGAGAGTTTACGGTCTTCGAT CGCTCTGTTCYTGKTTCCAACGGACTTGKTCATGGACAGGTTTGTTTGTTGT[C/G]AACAATTTGGCA TATT-GTTTGTGGYKTTCATGGACAGGTTTTGTTCTTAGTGTTGTCTGTG-- TGGACAGCTTTTGGAYCGGATCGGCCCTCCTACTGAAGACCTTAAGAAGAAAGGGATCGACTTCTCGTT GTGGTTCAAGCCTGACAA-TACCCKACYGACTTTTGAGC-GCAYCAAGG---------CA-------- CCACCACCAGCCATKGCCACCATAATAAA-GCAGCCATCATTTKKDRRRVM | SEQ ID NO:128 |
| PZA00521.3 | ARTTCCCATGAAAAGGAGACCRGKATGCTTTTGTATCAATGCTTGAGGCACTATGCAATGCAGAAAAG ACAACAGAGGCTATTGATCTACTGCATATGATGCCTGAAAAGGGGATTACTACACATGTTGGAATGTAT AATATGAT[A/C]TTTTCTGCTCTTGGGAAGCTGAAGCAGGCTGTCTTTCATGAGCAGCCTCTATGATAC GATGAGAGCCAATGGTGTTGTTCCTGATGTTTTCACGTA | SEQ ID NO:129 |
| PHM5599.20 | AAAAAAAGYGSAGDVVKRRKRMBEWGBYMNNKMRRAMRVRRAAVVNNDDNNRRRRDDNDNEDNNNDRVN RHDVRRRARADNCCVAR-TYMDRRM--K-ARVRRVGG-ATCCVG-TGCCGSSGVMRACCGG- TTYRAVGCYATCSGVACCSTBGTCCCGSG- SATGGTCAAGCTGGTGGMGGAMACMRCCGAMCAVGTYCWHSRNTTYGARGKKCC- GGAGATGATAGAGAGTAAGCTAGCTAG---SAMRCRM--TBRWYTYAGGA------- MTGSWTGTWATCTWAATCTTAAAAAA----- ATSATTTGCTTTGCYAGGGGACCGGTTCKCGTGGTTCAARGACGARGAGTTCGCGAGGCAGACGATCGC GGGGGCTMAACCCGCTGTGCATCCAGCTGCTGAC[C/T]GAGTTCCCCATCAAGAGCAAGCTGGACCCGG AGGTGTACCGGCCAGCRGAGTCCGCCATCACCAAGCAGATCCTGGAGAACC-AGATGAAC- CGCSCGYTCACCSTGGAGCAGGCCGCTGGCGGCGAAGCGGCTCGTTCATCCTGGACTACCACGACCTGTTC CTGCCCTACGTGCACAAGGTGCGG-AGCTGCAGGACKCGACGCTCTACGCCTSSSGCACCRTCT- CTTCSTGACG-R--MCBK-YAC--KDBSHHDNBSGKKDWA | SEQ ID NO:130 |
| PZA00193.2 | ACTTTMCRGGCCACACCAATTCTGCTTGGTTCTTGAAGATACATTCTTCCTATGGTGCCMCCTATATAA AAGCCATTTCTGG--- TTATGTTTATCCTTGACATGTCAACAGAT[C/T]AGTGTTGGGTTGCAGTCATGCGGTCCTTAAGTCYM CGACAAGGCGAGAAGTCATTGCTKCTAGCATTGTGATCGTCGGCCAC-- AAGTAATCWAAAAGTGAGAGCTACTTGTTCCTAGCAAATGGAGAAGGGCCATATATAGGTTKATGATCA AATTCAGT--------GTATGCAAGCAGCATATTTTGTTTAGAGWTAGCTTT | SEQ ID NO:131 |
| PZA00445.22 | ACAACCTACTAGCGTCATGTTCTTT----------TTTTYTTCTTCTT--- TCCCTTACAATCCCTTAGTTCTTGCAAGCA- CAGGTGTACATATAASTAA[A/T]TTCTGGTCATTGACTGATCTTCTTTKTTCTCGCAAACAAYTGCAG CCCGCACAAGCTTCAGGCCGTCTGCAAAAGTGGGGCGGCAAAGGCACCGATGAACT | SEQ ID NO:132 |

Figure 5B

| Marker Name | Context Seq | SEQ ID NO: |
|---|---|---|
| PZA02151.3 | GTCCACAGRGGAAGGAGAGGTGGGTACAACAAGAGTCCTGTACGGAGCCGTTCACCCCCCGCCAGGAAA AGGTCACMTAGCGCATCGTGCACGGTCAGTTTC[C/T]AGGAGCCACCTTTCTAGGTCAGTATCAAAGTC TCCACCAGTGCATCATCCCTCSCCACTTGATTCTCCATCTCTGGAGCGTGCAAGTGATGG-AAATCTCG | SEQ ID NO:133 |
| PHM15427.11 | ANANNNNNNANTANGGARAARAATMWKGGRR-A-G-YTTTKR-A-DRA-B-SG--WW-RG-TT-W-RG- G-GGNA-HA-MA---AYY-AA-MGG-TWGGAT---CAA-A-GA-MRAHWGGG-KTA-CC-MGG-RA- CGGGG-RGKTTYTTGG-SATTTT-TGTYTG--SAA-HHA- MTTYTGMAAGCYTGCCCAGGGGTTAMTTYTCCTGKTAT- SGVACCGAAAGCSCGKCAMGACGACGGCAGCCTGGACCTGATTCTCGTCCATGGAAGCGGCAGGYTGAG ACTGTTTTGSTTCYTTGTTGCCTATCAGYTCTGCTGGCATCTTCTRCTCCCCTACGTGGAATATGTCAA GGTATGTATCGTGACTTTCTTTGTATCTGTTTACAGCGCTTGTTGCGGCGGTTCATGTACCTATAGGGC TTA----------- GTAGATATCCTTCACCTTACTAGCATGCTCTTTCCTAGAACA[C/T]AGGACTCCATCAGTTTGTCWTC GCTTCTTAGATGMCCGTGCACTGATGTGGYATTTTGTTGTTGCGRCAATGATT- GCTCGCAGATAAAAGAAGTGAAGGTTAGGCCAGTTGGCAGTACCCACAGTGGTTGTGGYGTCGACGGTG AGCTTCTKGATGGAGAGSGCGGTGCTGAATGGCAGTGCTCGCTGCTTCCAGMAC- AAGGCAGGCTGCTTG-CMR-G-ATCC-B--GK-SY--RVB-NNRNKKKGAAARAAAA | SEQ ID NO:134 |
| PZA00521.3 | ARTTCCCATGAAAAAGGAGACCRGKATCCTTTTGTATCAATGCTTGAGGCACTATGCAATGCAGAAAAG ACAACAGAGGCTATTGATCTACTGCATATGATGCCTGAAAAGGGGATTACTACAGATGTTGGAATGTAT AATATGAT|A/C|TTTTCTGCTCTTGGGAAGCTGAAGCAGGTGTCTTTCATGAGCAGCCTCTATGATAC GATGAGAGCCAATGGTGTTGTTCCTGATGTTTTCACGTA | SEQ ID NO:135 |
| PZA02207.1 | TBSSSSYTCACTAAGTGTGATTGTAACAGTGGTACCTCTTGTGTTCTGTGTTCCGCGATGTTGCAGTTG GTTGCTTGATCGAAAGATGTTTCA[A/G]CCTCCCATCTGCTAGCTATGATACAGATGGTYCCTGATAA TAATGATGACATATTCTGTGATGGATGCCACRRCATTTTTTKKTTTTGTTTTTGCATTCAGATATTTCR GCTTCCTKRTAGTTTTACATGTCCCAACTAGGAATGAGAAC | SEQ ID NO:136 |
| PHM565.31 | TTKVNNBN-----W-HM-AVR----CTGAAGA-TTGCTGAAGGAGTGGGAGTCTAGC-AAA--YY-K-- --- TTCCGTGTCCCAAACGTCCTGCTCACAGGGTACCGCCAGAAGGCCTTGCTGGACA[A/G]GGCCGAGAT GCTGCTCGACGGCTTCTTGAAGAAGGGAAAGACGCCTCCTTCGACCAGCTGGGGGATYGTGGCAATCGG CTATGCGGGAAAAGGTGATGTGGCGAAAGCTTATGAGATGACCAAGAACGCCCTCTCTGTGCACGCCCC CAATACTGGCTGGATCCCTAGGCCTTCCATGCTTGAGATGATACTTAAGTACYTCGGAGACGAGGGGGA GGTCAAKGATGKHKAAGCTTKCGTTAGTCWGCT---- GAAAGCTGCTGTGCCASTGGACTCTGATATGACCGAGGCCTTTGTCKAGGGGCTCK------ TKCSAGGGAADAAAKGAWKGCTR--- AARAGGCARCGGAAKCTCCTCGCGGGGATBWTATTGCCTRARCTBGYWKTCSGTKTTT-CASCGCTKC- KYCYVAAWKG--TC-W- NYTBWNNNEYHCRADHBDNBBNNHENNBNNNYNENNHNVNNNNNYNBHHENKBRYYYNCTNTTNNCGCNA | SEQ ID NO:137 |
| PZA03578.1 | ATGCAGCAGAGAATACTGTGGAAGKTGAYGATAAGAAAGAGGAAGCCCCWGCTGTNGATGCAGCAGAGA AGAAYGAGGAAGGTGATGATAAGAAAGAGGAGGAGCCCCCTGCAGAA[A/G]ACTGTTGAGAAAGAG GTGGTCCCTGCTGTAGATGCAGCAGAGAATACTGAACAAAGCACCGGTGGGCAAGCACAGCCTAAYGAT GTTGSTGCCCCA | SEQ ID NO:138 |

Figure 5C

| Marker Name | Context Seq | SEQ ID NO: |
|---|---|---|
| PZA00300.14 | AAAAAA--<br>TCCTCTTGTCTATCCGACRCCMAAACATAGGTCTAAGGTCYRSTTTYGRTYGYGKTCGTTC-<br>TMACRTGRGCTACRRTRCCRYTGTCTATRGACATATGTCTCAARCYTAGTTTTCGTYRTGGTCKATCTC<br>TCATCKGTTACRSTTTTAC-GCTAYCTA-------IGGGTGACAGISKAASMSTCIAASGGTTTTRIT-<br>------GWG-<br>AAGWITTTTCTTAATACAATACWYNNNNNNNNNNNNNNNNNNNNNNNNNNNNNNNNNNNNNNNNNNNN<br>NNNNNNNNNNNNNNNNNNNNNNNNNNNNNNNNNNNNNNNNNNNNNNNNNNNNNNNNNNNNNNNNNNNN<br>NNNNNNNNNNNNNNNNNNNNNNNNNNNNNNNNNNNNNNNNNNNNNNNNNNNNNNNNNNNNNNNNNNNN<br>NNNNNNNNNNNNNNNNNNNNNNNNNNNNNNNNNNNNNNNNNNNNNNNNNNNNNNNNNNNNNNNNNNNN<br>NNNNNNNNNNNNNNNNNNNNNNNNNNNNNNNNNNNNNNNNNNNNNNNNNNNNAGGRGTTRTCTTAGC<br>CYWCAGGTCATTTTKTT-<br>ACMGTCTGAATTTCTTAYACTTTYTAGGTCAGTAGTAACTTGTAGATTTYGACTTGATTTTCACAGGCC<br>TGATTAAAPGCATTGAARYTTATCCARCMKATCAAGACAAATACMCAGGTAYCACTTATGCAGATTTGT<br>TCCAGTTAGCAAGTGCTACGGCGATTGAGGTCACTGTCCTTTCTCTGATTAAGTATCTGACTTGGTCAC<br>TTKATCACTCAAGTCTATGYAGTCATATGTTTTGTCAATCACATGATACAGGAAGCTGGTGGTCCAAAA<br>MTTCCAATGAAATATGGACCKGTTGATGTCACAGCAKCTGARCAGTCTCCRCCCGACGGGAGGCTTCCY<br>GGTCAGTGTTTCYAATGGGTTCTTCATTCCATATCAATGTTTCATT[A/G]TTGTTTTGTTCAATG-<br>CTTGCAATGTGAYTIATGACAGGTGCCTATC | SEQ ID NO:139 |
| PZA00067.10 | CGGAACTGTAGTTGCAATTCGTAATTCCAGCATGCATTCCACAATRTCACAAAACACCTAAACRTAAAT<br>CTCTCTMTATTAAGTCAGATACCAACATTTTTGCCTATTAATTGCAGCTAGCAAATGCCTCCCCGGACG<br>TCATCAACACGCTGATCCCAGACCATGCTAGGCGGGCATCTTGGGCTCACTTTATTGCCCACC[A/G]CT<br>GGACCATAGGCGAAGGCTCTATGGTGTTTAAACCTTGCTCTTCTGATTCTCGTTGTGCCATAGGCAA<br>TTCAAGGTGTAGAATCTGACCATTATTGGAAAGCCAAACACGAGCTGGCGCAATGTGTTGCATAAGGA<br>GAGGCGGTATGTTSGTGYAGCCAGCCTTTTGYCGCCTGTTTTAATGCAAAATCTGATTT | SEQ ID NO:140 |
| PZA01563.1 | AAAGACAGCTAATGTCCTGACGCGAAGTGATCTGCGAGCTCGCAGAAGAGGTCGCAGGCATCATCGGCA<br>TGCTGATGACTAGTTTCCTATTGTGAATGTTG[G/T]GTAGAAGTGCTGTGGAATACCCWAGAC-<br>ATTACCATTTTATTTGGGCCTCATGCCCC | SEQ ID NO:141 |
| PZA00647.9 | CGTTYGAGGYGGATCGTATCTGYCKGY----ACGCAGTGTTTGGSMAAA--------<br>TACTTGGGAGTCGCAAGAAAT---TGTGTAAATTAT---<br>AGA[A/G]GAGGATGGCGACGAAGCACGCATGTGTTACGTAGTTGGCGTTTGTGTGCACATGGTGGTGG<br>GCAGGGK-------CTAG-------AGGGTTTATHTTTRGGTTATTTTCSYAGTGGAATGWATCTTA | SEQ ID NO:142 |
| PZA01095.1 | TTGTGGTCTTGGGAGTYGGAGTTTGATTTCAAGGCGRAGCAAAATCTTRCAGAGATCGCTGAGGAACTG<br>CCTCATCTGTAGCCTGTTTCTTAAAATAATCT[C/T]CAGTTCTTTACTTCCCTGTAGCCTCTATAAG | SEQ ID NO:143 |

Figure 5D

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| B73 | 0.2595 | 27.1442 | 137.4 | 22.9893 | 362.29 | 17.1534 | 92.6875 | 0.1017 |
| B73xM0001 | 0.3101 | 28.1164 | 181.28 | 33.8449 | 584.33 | 17.463 | 181.5 | 0.1049 |
| B73xM0002 | 0.2679 | 26.4717 | 163.18 | 27.4389 | 607 | 15.9049 | 161.5 | 0.1116 |
| B73xM0004 | 0.3237 | 27.8184 | 179.57 | 32.5551 | 593.16 | 15.7855 | 192.4 | 0.1194 |
| B73xM0005 | 0.3312 | 24.9233 | 167.28 | 20.9466 | 454.08 | 13.9758 | 148.87 | 0.1085 |
| B73xM0006 | 0.2748 | 25.5387 | 195.95 | 27.959 | 679.77 | 16.9334 | 187.92 | 0.0882 |
| B73xM0007 | 0.377 | 27.8707 | 234.14 | 41.6269 | 797.84 | 15.3992 | 299.18 | 0.1334 |
| B73xM0008 | 0.3225 | 28.7335 | 171.83 | 33.3876 | 608.43 | 16.2448 | 196.87 | 0.1059 |
| B73xM0010 | 0.2719 | 24.9718 | 166.44 | 21.6692 | 588.72 | 17.2854 | 158.64 | 0.1201 |
| B73xM0011 | 0.3265 | 29.7292 | 173.29 | 36.7821 | 615.85 | 16.2761 | 200.31 | 0.1303 |
| B73xM0012 | 0.3045 | 29.7283 | 210.41 | 35.6542 | 661.18 | 15.4226 | 201.68 | 0.1143 |
| B73xM0013 | 0.2773 | 26.9557 | 171.75 | 28.8212 | 591.29 | 16.8877 | 163.3 | 0.1223 |
| B73xM0014 | 0.2633 | 26.2687 | 167.46 | 25.9295 | 558.84 | 16.0012 | 145.88 | 0.1419 |
| B73xM0015 | 0.3443 | 28.3233 | 182.58 | 33.3802 | 583.4 | 16.7054 | 205.19 | 0.115 |
| B73xM0016 | 0.2814 | 29.974 | 186.04 | 30.4703 | 659.37 | 17.5389 | 182.22 | 0.08767 |
| B73xM0017 | 0.3084 | 27.6901 | 183.9 | 36.6454 | 656.43 | 17.3747 | 201.69 | 0.1368 |
| B73xM0021 | 0.2478 | 26.7921 | 173.18 | 27.9359 | 607.05 | 16.4917 | 152.03 | 0.1264 |
| B73xM0022 | 0.3122 | 27.9593 | 158.47 | 31.1828 | 497.24 | 17.3587 | 153.55 | 0.1408 |
| B73xM0023 | 0.3453 | 26.4406 | 199.84 | 33.3168 | 641.09 | 15.7028 | 217.09 | 0.1068 |
| B73xM0024 | 0.3354 | 26.3232 | 191.37 | 28.8058 | 482.32 | 15.2159 | 153.55 | 0.1241 |
| B73xM0025 | 0.3028 | 29.6752 | 190.91 | 40.2341 | 567.79 | 16.9306 | 171.45 | 0.1266 |
| B73xM0026 | 0.3249 | 27.6211 | 183.27 | 37.2246 | 545.28 | 15.8354 | 174.72 | 0.107 |
| B73xM0027 | 0.3286 | 26.435 | 194.1 | 30.4513 | 592.75 | 15.1728 | 195.48 | 0.1227 |
| B73xM0028 | 0.2783 | 26.6366 | 169.89 | 25.3544 | 577.48 | 15.9628 | 155.77 | 0.1012 |
| B73xM0029 | 0.2908 | 26.4605 | 179.54 | 28.6736 | 640.68 | 16.4532 | 184.07 | 0.1137 |
| B73xM0030 | 0.271 | 25.8424 | 169.78 | 29.9544 | 512.13 | 17.1311 | 153.4 | 0.1009 |
| B73xM0031 | 0.3026 | 27.0307 | 175.82 | 29.882 | 570.2 | 15.3025 | 170.5 | 0.1432 |
| B73xM0032 | 0.3555 | 26.3289 | 176.4 | 28.2879 | 531.45 | 14.4228 | 183.09 | 0.1337 |
| B73xM0033 | 0.2949 | 27.2646 | 158.08 | 24.8191 | 440.75 | 15.3438 | 131.76 | 0.1015 |
| B73xM0034 | 0.2805 | 28.5391 | 157.66 | 29.1271 | 620.44 | 18.178 | 174.71 | 0.1372 |
| B73xM0035 | 0.3149 | 26.2485 | 180.37 | 26.9169 | 505.83 | 14.8047 | 156.68 | 0.118 |
| B73xM0039 | 0.3108 | 28.8997 | 179.31 | 33.6196 | 677.77 | 17.3061 | 209 | 0.1122 |
| B73xM0043 | 0.322 | 26.6904 | 193.78 | 28.0799 | 511.55 | 15.5254 | 162.64 | 0.1127 |
| B73xM0044 | 0.307 | 27.198 | 189.59 | 30.9399 | 606.45 | 15.7789 | 185.3 | 0.1224 |
| B73xM0045 | 0.295 | 28.1607 | 183.67 | 30.9309 | 704.58 | 17.2086 | 206.12 | 0.1326 |
| B73xM0046 | 0.2676 | 26.206 | 171.16 | 28.811 | 563.65 | 16.4189 | 153.18 | 0.1043 |
| B73xM0047 | 0.3019 | 24.929 | 191.78 | 25.0654 | 583.08 | 16.032 | 173.8 | 0.1166 |
| B73xM0048 | 0.2886 | 26.1159 | 182.1 | 27.4087 | 449.74 | 14.7765 | 137.67 | 0.12 |
| B73xM0051 | 0.3098 | 25.432 | 164.5 | 24.4078 | 459.16 | 15.9868 | 144.89 | 0.1372 |
| B73xM0052 | 0.2849 | 26.8314 | 157.48 | 26.542 | 494.21 | 16.5933 | 137.95 | 0.148 |
| B73xM0053 | 0.3164 | 28.1179 | 157.33 | 25.7426 | 503.87 | 16.89 | 156.26 | 0.1039 |
| B73xM0054 | 0.2818 | 28.4499 | 163.08 | 30.978 | 659.09 | 17.9552 | 188.03 | 0.146 |
| B73xM0055 | 0.3107 | 30.2395 | 179.29 | 35.4068 | 623.64 | 17.5596 | 193.87 | 0.1269 |

Figure 6A

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| B73xM0056 | 0.2726 | 27.44 | 169.7 | 30.7976 | 660.03 | 17.4709 | 178.11 | 0.1212 |
| B73xM0057 | 0.2981 | 27.1025 | 176.38 | 27.2853 | 578.86 | 16.2581 | 172.09 | 0.131 |
| B73xM0058 | 0.2644 | 30.4467 | 182.44 | 33.9425 | 706.48 | 19.6622 | 183.47 | 0.1077 |
| B73xM0059 | 0.304 | 29.3215 | 161.88 | 33.1415 | 630.57 | 16.7667 | 191.36 | 0.1267 |
| B73xM0060 | 0.33 | 30.2356 | 179.79 | 35.9485 | 562.79 | 16.5075 | 185.17 | 0.117 |
| B73xM0061 | 0.3071 | 26.9444 | 174 | 36.2395 | 584.67 | 16.0219 | 191 | 0.0738 |
| B73xM0064 | 0.3365 | 26.7835 | 168.88 | 30.6917 | 531.33 | 15.7784 | 179.56 | 0.1153 |
| B73xM0065 | 0.2818 | 28.784 | 175.47 | 27.7036 | 648.04 | 18.1512 | 180.73 | 0.1122 |
| B73xM0066 | 0.1977 | 19.5575 | 101.53 | 7.8955 | -7.859 | NA | -2.0902 | 0.1138 |
| B73xM0067 | 0.2961 | 29.1853 | 204.82 | 39.8805 | 708.79 | 16.2886 | 209.28 | 0.1191 |
| B73xM0069 | 0.2666 | 27.0921 | 167.51 | 27.0508 | 567.19 | 15.7779 | 151.35 | 0.1357 |
| B73xM0070 | 0.2847 | 24.6849 | 156 | 20.1382 | 440.55 | 14.8029 | 125.33 | 0.1124 |
| B73xM0071 | 0.2518 | 27.404 | 152.48 | 24.9957 | 533.27 | 16.9949 | 132.29 | 0.1197 |
| B73xM0075 | 0.3148 | 27.1813 | 189.12 | 33.566 | 579.03 | 15.5646 | 180.29 | 0.1148 |
| B73xM0076 | 0.326 | 28.0846 | 187.86 | 34.9719 | 573.16 | 17.4676 | 179.23 | 0.09064 |
| B73xM0077 | 0.3394 | 28.5536 | 210.3 | 39.366 | 748.98 | 16.917 | 254.95 | 0.1531 |
| B73xM0078 | 0.3363 | 28.453 | 173.33 | 36.0084 | 540.19 | 16.8252 | 180.16 | 0.1127 |
| B73xM0079 | 0.3059 | 24.8338 | 167.02 | 28.0315 | 487.36 | 14.9727 | 158.23 | 0.1103 |
| B73xM0080 | 0.3197 | 26.9056 | 167.47 | 29.1389 | 544.13 | 15.7142 | 169.81 | 0.1167 |
| B73xM0081 | 0.2885 | 26.4711 | 181.93 | 31.6459 | 639.01 | 15.906 | 184.36 | 0.0933 |
| B73xM0083 | 0.3447 | 28.1369 | 167.53 | 29.9941 | 514.75 | 15.019 | 181.1 | 0.1405 |
| B73xM0084 | 0.313 | 26.6476 | 187.76 | 28.44 | 590.23 | 15.7056 | 185.14 | 0.1015 |
| B73xM0085 | 0.2824 | 25.0313 | 156.75 | 26.6963 | 517.35 | 16.7402 | 153.68 | 0.1375 |
| B73xM0086 | 0.2917 | 25.7823 | 171.58 | 26.2372 | 574.63 | 16.9091 | 168.63 | 0.1439 |
| B73xM0088 | 0.3115 | 28.5759 | 201.69 | 41.515 | 694.16 | 16.3236 | 216.87 | 0.1145 |
| B73xM0090 | 0.3098 | 27.6035 | 183.2 | 29.7685 | 630.01 | 17.576 | 192.64 | 0.09848 |
| B73xM0091 | 0.3121 | 28.3291 | 178.12 | 32.085 | 609.06 | 16.0602 | 190.49 | 0.1322 |
| B73xM0092 | 0.3247 | 25.4252 | 181.72 | 24.6308 | 619.51 | 15.8535 | 202.11 | 0.1428 |
| B73xM0093 | 0.2985 | 25.5809 | 201.04 | 29.3307 | 630.51 | 15.5789 | 188.07 | 0.1033 |
| B73xM0095 | 0.3295 | 30.2535 | 176.39 | 34.3908 | 577.19 | 17.0787 | 183.57 | NA |
| B73xM0096 | 0.3039 | 26.8474 | 182.05 | 31.5766 | 638.62 | 16.209 | 196.81 | 0.09762 |
| B73xM0097 | 0.3131 | 26.3553 | 184.04 | 29.6558 | 588.29 | 15.1427 | 181.54 | 0.138 |
| B73xM0098 | 0.2864 | 26.0877 | 186.39 | 28.1589 | 584.41 | 16.6328 | 166.19 | 0.122 |
| B73xM0099 | 0.3451 | 27.9588 | 184.14 | 35.096 | 526.08 | 16.6067 | 176.12 | 0.1255 |
| B73xM0100 | 0.2969 | 25.5007 | 173.56 | 28.7216 | 498.78 | 14.2774 | 148.09 | 0.129 |
| B73xM0101 | 0.3319 | 28.0719 | 195.12 | 32.2307 | 633.99 | 16.0261 | 207.27 | 0.1098 |
| B73xM0102 | 0.3367 | NA | NA | 38.0738 | 764.25 | 19.8722 | 257.27 | 0.09284 |
| B73xM0103 | 0.322 | 26.9912 | 190.99 | 30.8157 | 619.81 | 15.5317 | 197.82 | 0.1166 |
| B73xM0104 | 0.3101 | 28.144 | 165.88 | 27.3816 | 472.08 | 16.0363 | 142.66 | 0.1345 |
| B73xM0105 | 0.3074 | 26.3984 | 182.52 | 32.885 | 595.71 | 16.1994 | 180.99 | 0.128 |
| B73xM0106 | 0.3057 | 26.3683 | 174.39 | 27.528 | 509.12 | 16.5049 | 156.48 | 0.06513 |
| B73xM0107 | 0.2691 | 26.998 | 181.44 | 31.5489 | 635.43 | 15.1491 | 169.26 | 0.1158 |
| B73xM0109 | 0.3099 | 26.512 | 187.36 | 27.7666 | 573.02 | 15.5144 | 177.96 | 0.1034 |
| B73xM0110 | 0.3312 | 28.4706 | 183.96 | 37.9613 | 614.11 | 16.9469 | 201.94 | 0.1092 |

Figure 6B

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| B73xM0113 | 0.2631 | 28.0617 | 147.66 | 24.2872 | 522.17 | 19.0758 | 129.31 | 0.09075 |
| B73xM0114 | 0.2819 | 27.4205 | 188.22 | 32.8694 | 657.54 | 16.8195 | 188.59 | 0.1457 |
| B73xM0115 | 0.315 | 28.2104 | 198.7 | 32.4641 | 626.89 | 16.0885 | 197.24 | 0.111 |
| B73xM0116 | 0.3659 | 26.9832 | 174.11 | 28.5788 | 525.44 | 15.9639 | 188.8 | 0.08741 |
| B73xM0117 | 0.3328 | 27.9861 | 222.29 | 38.3702 | 710.27 | 15.9627 | 236.5 | 0.1099 |
| B73xM0118 | 0.3155 | 26.7717 | 187.11 | 30.9926 | 613.88 | 16.04 | 191.38 | 0.1212 |
| B73xM0120 | 0.2979 | 28.3668 | 186.31 | 34.1538 | 718.07 | 18.8496 | 213.37 | 0.09768 |
| B73xM0121 | 0.3079 | 26.6292 | 176.14 | 28.6534 | 564.71 | 17.1895 | 173.22 | 0.1096 |
| B73xM0122 | 0.32 | 27.8995 | 157.31 | 28.6237 | 500.61 | 16.7833 | 169.2 | 0.1139 |
| B73xM0123 | 0.3188 | 24.5946 | 195.09 | 24.4953 | 585.68 | 14.52 | 182.8 | 0.1028 |
| B73xM0124 | 0.2723 | 27.3256 | 185.33 | 28.7176 | 634.18 | 17.1697 | 175.24 | 0.1297 |
| B73xM0125 | 0.2448 | 29.1155 | 182.25 | 32.611 | 592.44 | 17.2059 | 139.09 | 0.09623 |
| B73xM0126 | 0.3177 | 25.8731 | 190.89 | 30.197 | 543.73 | 14.8095 | 172.95 | 0.1037 |
| B73xM0127 | 0.3136 | 26.9867 | 194.88 | 34.1478 | 629.78 | 15.7746 | 198.27 | 0.1244 |
| B73xM0129 | 0.3249 | 29.2382 | 191.79 | 37.7068 | 619.71 | 16.24 | 201.9 | 0.1341 |
| B73xM0130 | 0.2902 | 25.4749 | 167.24 | 26.0344 | 556.52 | 16.6732 | 151.39 | 0.09043 |
| B73xM0131 | 0.3169 | 26.5891 | 191.42 | 30.0734 | 630.76 | 15.7303 | 201.22 | 0.1109 |
| B73xM0132 | 0.3309 | 27.0813 | 186.08 | 30.8376 | 575.98 | 15.456 | 189.23 | 0.154 |
| B73xM0133 | 0.3064 | 29.4285 | 180.77 | 34.3598 | 618.98 | 16.6212 | 190.3 | 0.1059 |
| B73xM0138 | 0.2999 | 25.3037 | 159.97 | 22.4477 | 494.39 | 14.9309 | 148.85 | 0.1499 |
| B73xM0141 | 0.3405 | 29.2962 | 182.49 | 34.2248 | 669.11 | 17.0368 | 226.13 | 0.08872 |
| B73xM0142 | 0.2738 | 26.3302 | 165.36 | 25.2784 | 537.58 | 17.4188 | 151.5 | 0.1071 |
| B73xM0143 | 0.2677 | 29.5453 | 175.04 | 32.1487 | 503.14 | 16.106 | 136.43 | 0.09557 |
| B73xM0144 | 0.3152 | 28.0045 | 193.71 | 35.3415 | 638.48 | 15.9763 | 198.7 | 0.1227 |
| B73xM0145 | 0.3163 | 29.4406 | 167.09 | 37.1712 | 525.83 | 19.2391 | 164.07 | 0.1212 |
| B73xM0147 | 0.3128 | 26.6207 | 185.18 | 29.4473 | 598.73 | 15.5105 | 186.81 | 0.1337 |
| B73xM0149 | 0.2646 | 26.862 | 170.61 | 29.3068 | 650.69 | 18.6618 | 170.5 | 0.1084 |
| B73xM0150 | 0.2826 | 24.274 | 152.94 | 19.4662 | 466.23 | 16.0045 | 131.58 | 0.1258 |
| B73xM0151 | 0.2876 | 29.4213 | 175.25 | 30.2844 | 686.51 | 18.0357 | 196.64 | 0.08479 |
| B73xM0152 | 0.3118 | 26.252 | 169.55 | 32.0868 | 604.43 | 16.4573 | 181.5 | 0.08977 |
| B73xM0154 | 0.3283 | 26.6253 | 190.29 | 34.3098 | 660.87 | 15.2626 | 212.24 | 0.1292 |
| B73xM0155 | 0.3441 | 25.7286 | 199.14 | 33.0832 | 575.71 | 15.1614 | 197.62 | 0.1232 |
| B73xM0156 | 0.3126 | 29.2853 | 169.76 | 29.9742 | 634.64 | 18.6352 | 197.1 | 0.1323 |
| B73xM0157 | 0.2943 | 28.3187 | 198.38 | 33.2948 | 640.92 | 17.0086 | 187.26 | 0.1383 |
| B73xM0160 | 0.2898 | 27.69 | 183.01 | 32.1438 | 653.34 | 17.5097 | 184.5 | 0.1012 |
| B73xM0160A | 0.3039 | 27.616 | 176.25 | 31.1063 | 605.55 | 16.9416 | 184 | 0.1268 |
| B73xM0161 | 0.3356 | 26.3175 | 192.58 | 33.2661 | 520.99 | 15.2718 | 173.6 | 0.1163 |
| B73xM0162 | 0.2825 | 27.4193 | 172.42 | 29.0666 | 631.94 | 16.3621 | 179.26 | 0.1161 |
| B73xM0162A | 0.267 | 27.0522 | 181.84 | 30.8981 | 608.23 | 17.8773 | 162.16 | 0.106 |
| B73xM0163 | 0.2948 | 28.6792 | 189.36 | 34.2046 | 630.09 | 17.7311 | 184.38 | 0.1308 |
| B73xM0165 | 0.3196 | 28.233 | 169.85 | 31.4613 | 614.87 | 17.8335 | 195.03 | 0.1051 |
| B73xM0166 | 0.3099 | 25.2282 | 178.13 | 26.7965 | 486.18 | 14.6912 | 146.21 | 0.1286 |
| B73xM0167 | 0.2557 | 27.6055 | 171.56 | 28.595 | 599.99 | 16.5939 | 148.92 | 0.1195 |
| B73xM0168 | 0.3321 | 29.6078 | 180.13 | 38.515 | 599.18 | 18.208 | 193.58 | 0.1145 |

Figure 6C

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| B73xM0169 | 0.2861 | 28.5674 | 143.97 | 25.9357 | 298.58 | 19.1748 | 98.1504 | 0.1267 |
| B73xM0173 | 0.3093 | 28.4041 | 174.61 | 31.3411 | 588.61 | 16.9158 | 180.59 | 0.1071 |
| B73xM0174 | 0.3166 | 27.005 | 188.46 | 32.7953 | 513.58 | 15.1595 | 175.3 | 0.1202 |
| B73xM0176 | 0.2945 | 27.4412 | 169.52 | 29.6208 | 591.51 | 17.157 | 174.82 | 0.1278 |
| B73xM0177 | 0.3244 | 29.5096 | 204.83 | 38.1799 | 676.08 | 16.9821 | 218.12 | 0.1226 |
| B73xM0178 | 0.2878 | 28.0398 | 175.46 | 32.3741 | 698.65 | 17.8257 | 201.85 | 0.09085 |
| B73xM0179 | 0.3158 | 27.606 | 188.41 | 30.6407 | 608.75 | 15.3211 | 191.05 | 0.09952 |
| B73xM0180 | 0.3216 | 26.2836 | 173.51 | 27.0455 | 563.59 | 16.2188 | 177.73 | 0.1146 |
| B73xM0181 | 0.3025 | 29.7013 | 188.12 | 36.2445 | 679.71 | 17.9615 | 204.44 | 0.1116 |
| B73xM0185 | 0.2897 | 26.5551 | 183.97 | 29.4089 | 638.06 | 17.1099 | 178.12 | 0.09866 |
| B73xM0187 | 0.308 | 30.2933 | 174.41 | 32.7023 | 664.9 | 17.8709 | 204.18 | 0.13 |
| B73xM0188 | 0.3052 | 29.8018 | 184.08 | 32.6425 | 543.22 | 17.4734 | 166.58 | 0.1051 |
| B73xM0189 | 0.3583 | 28.6137 | 180.91 | 37.9238 | 648.7 | 17.8861 | 226.9 | 0.1055 |
| B73xM0191 | 0.2928 | 26.4914 | 159.58 | 25.254 | 474.76 | 16.028 | 144.27 | 0.1158 |
| B73xM0192 | 0.1919 | 30.6147 | 177.68 | 30.5342 | 594.31 | 16.9716 | 109.81 | 0.08821 |
| B73xM0194 | 0.3092 | 31.343 | 189.1 | 38.9674 | 671.93 | 18.3769 | 209.09 | 0.1122 |
| B73xM0195 | 0.3408 | 27.8783 | 178.19 | 35.3488 | 569.27 | 16.1932 | 187.07 | 0.1168 |
| B73xM0196 | 0.3041 | 30.4218 | 181.28 | 38.9166 | 621.1 | 17.6845 | 186.13 | 0.1022 |
| B73xM0197 | 0.2721 | 28.6628 | 165.7 | 33.1256 | 633.53 | 17.1766 | 172.65 | 0.0906 |
| B73xM0198 | 0.3481 | 27.7774 | 176.04 | 29.7992 | 487.3 | 15.9418 | 155.42 | 0.1144 |
| B73xM0199 | 0.2204 | 22.3869 | 136.49 | 17.7517 | 316.12 | 14.0975 | 96.6883 | 0.1256 |
| B73xM0200 | 0.299 | 29.1341 | 196.89 | 36.6559 | 682.01 | 16.3888 | 200.86 | 0.1264 |
| B73xM0201 | 0.3176 | 29.0577 | 182.74 | 35.1432 | 743.49 | 18.4306 | 233.66 | 0.134 |
| B73xM0203 | 0.3201 | 28.6493 | 186.98 | 33.4681 | 625.2 | 16.6719 | 198.14 | 0.1067 |
| B73xM0204 | 0.2932 | 26.9812 | 177.54 | 30.5402 | 636.78 | 15.4159 | 186.05 | 0.1125 |
| B73xM0205 | 0.3572 | 28.2665 | 196.43 | 37.8177 | 602.81 | 15.5329 | 212.35 | 0.09405 |
| B73xM0206 | 0.2936 | 25.692 | 169.72 | 26.6998 | 574.29 | 16.7344 | 171.75 | 0.1278 |
| B73xM0208 | 0.2939 | 27.7785 | 172.52 | 31.6822 | 605.41 | 18.2061 | 183.21 | 0.09696 |
| B73xM0209 | 0.2904 | 28.1787 | 161.05 | 29.1701 | 561.28 | 17.7977 | 163.46 | 0.1104 |
| B73xM0210 | 0.3108 | 25.7738 | 202.59 | 31.896 | 559.35 | 14.6436 | 171.52 | 0.1257 |
| B73xM0212 | 0.3332 | 27.0246 | 182.56 | 29.2342 | 546.35 | 15.8409 | 179.92 | 0.1343 |
| B73xM0213 | 0.3208 | 28.6411 | 176.99 | 32.7619 | 573.55 | 16.3591 | 185.03 | 0.1407 |
| B73xM0214 | 0.3004 | 24.2184 | 181.96 | 30.0479 | 584.97 | 16.1755 | 174.72 | 0.09616 |
| B73xM0215 | 0.3265 | 27.2333 | 196.41 | 39.6021 | 590 | 16.2261 | 193.48 | 0.1203 |
| B73xM0216 | 0.354 | 27.1316 | 203.19 | 36.9773 | 688.21 | 15.9652 | 245.52 | 0.1039 |
| B73xM0217 | 0.2825 | 29.8416 | 165.31 | 31.5655 | 588.8 | 17.7785 | 171 | 0.09439 |
| B73xM0218 | 0.2967 | 25.9891 | 173.08 | 24.9739 | 561.93 | 16.5515 | 163.71 | 0.1132 |
| B73xM0219 | 0.305 | 27.7116 | 182.46 | 29.2788 | 552.09 | 16.9375 | 169.4 | 0.1325 |
| B73xM0220 | 0.2965 | 28.5531 | 176.29 | 33.8104 | 607.53 | 17.4716 | 177.85 | 0.09807 |
| B73xM0222 | 0.3034 | 26.8884 | 160.56 | 24.8886 | 531.79 | 17.37 | 160.74 | 0.1194 |
| B73xM0223 | 0.3322 | 28.5284 | 177.47 | 35.9272 | 664.34 | 16.9506 | 219.29 | 0.08632 |
| B73xM0225 | 0.2669 | 27.3046 | 185.89 | 34.241 | 579.71 | 16.3748 | 176.26 | 0.1073 |
| B73xM0228 | 0.2945 | 28.0168 | 173.44 | 32.9117 | 630.76 | 18.7321 | 185.43 | 0.1193 |
| B73xM0229 | 0.3228 | 30.4849 | 200.67 | 38.5825 | 764.85 | 18.4197 | 246.2 | 0.1388 |

Figure 6D

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| B73xM0230 | 0.3668 | 28.0962 | 188.16 | 33.4792 | 489.82 | 14.5989 | 176.45 | 0.1063 |
| B73xM0232 | 0.3141 | 26.0748 | 154.64 | 25.9453 | 494.11 | 17.0384 | 162.26 | 0.127 |
| B73xM0233 | 0.2636 | 28.4872 | 162.12 | 30.9101 | 562.54 | 17.2134 | 158.46 | 0.08534 |
| B73xM0234 | 0.3118 | 28.0183 | 185.65 | 32.0446 | 622.29 | 18.0969 | 190.97 | 0.08974 |
| B73xM0235 | 0.3043 | 25.9212 | 187.25 | 32.8105 | 656.68 | 16.7231 | 199.16 | 0.1247 |
| B73xM0236 | 0.3022 | 27.3661 | 174.58 | 29.4525 | 566.44 | 14.8905 | 168.87 | 0.1243 |
| B73xM0238 | 0.272 | 27.6211 | 166.6 | 29.339 | 610.45 | 16.795 | 162.3 | 0.1152 |
| B73xM0239 | 0.2929 | 30.0731 | 175.8 | 33.6907 | 669.51 | 18.8774 | 192.01 | NA |
| B73xM0240 | 0.2787 | 27.3529 | 169.25 | 27.2788 | 598.51 | 16.2298 | 169.3 | 0.1266 |
| B73xM0241 | 0.2921 | 24.5989 | 159.58 | 27.9388 | 548.98 | 16.6296 | 160.82 | 0.1038 |
| B73xM0244 | 0.3196 | 28.2959 | 179.92 | 31.8863 | 642.09 | 16.3704 | 204.24 | NA |
| B73xM0245 | 0.3053 | 30.2612 | 188.72 | 39.5222 | 627.43 | 17.4212 | 189.29 | 0.09293 |
| B73xM0248 | 0.3164 | 26.3011 | 195.27 | 29.291 | 647.83 | 15.6177 | 206.02 | 0.1314 |
| B73xM0249 | 0.2792 | 26.6816 | 160.69 | 28.2975 | 541.86 | 17.1102 | 163.1 | 0.09816 |
| B73xM0251 | 0.2874 | 26.9698 | 139.79 | 25.6891 | 513.82 | 16.1813 | 146.9 | 0.115 |
| B73xM0252 | 0.2968 | 30.481 | 199.48 | 41.0691 | 695.16 | 18.2836 | 206.71 | 0.1196 |
| B73xM0254 | 0.2531 | 26.1339 | 166.59 | 26.2152 | 569.91 | 16.613 | 142.01 | 0.1253 |
| B73xM0256 | 0.3091 | 31.0268 | 176.11 | 33.0721 | 415.27 | 17.2537 | 129.57 | 0.1206 |
| B73xM0257 | 0.303 | 27.4571 | 174.48 | 28.5497 | 603.66 | 15.9837 | 182.32 | 0.09769 |
| B73xM0258 | 0.2965 | 24.3528 | 166.15 | 25.7634 | 525.07 | 16.6647 | 156.24 | 0.1204 |
| B73xM0259 | 0.3485 | 28.6526 | 187.26 | 32.011 | 548.55 | 15.7289 | 190.45 | 0.1096 |
| B73xM0260 | 0.3114 | 27.6235 | 194.47 | 35.0733 | 659.01 | 15.9405 | 203.46 | 0.08964 |
| B73xM0262 | 0.314 | 27.4262 | 169.73 | 28.1044 | 522.46 | 15.9843 | 163.26 | 0.09149 |
| B73xM0263 | 0.289 | 28.3065 | 176.05 | 33.2936 | 676.93 | 17.6601 | 193.94 | 0.09037 |
| B73xM0264 | 0.2861 | 29.2003 | 177.13 | 32.146 | 636.64 | 17.6564 | 184.13 | 0.1247 |
| B73xM0265 | 0.2796 | 27.3228 | 166.25 | 28.0337 | 605.04 | 17.9386 | 172.96 | 0.1253 |
| B73xM0266 | 0.2905 | 27.8926 | 179.23 | 31.975 | 618.71 | 17.4505 | 178.95 | 0.1251 |
| B73xM0267 | 0.3015 | 29.2958 | 202.2 | 40.2081 | 727.95 | 16.9919 | 218.64 | 0.1115 |
| B73xM0269 | 0.2876 | 26.3881 | 176.71 | 27.1684 | 557.89 | 16.2276 | 157.94 | 0.1269 |
| B73xM0270 | 0.3255 | 29.0163 | 188.79 | 41.6554 | 601.44 | 16.3318 | 197.27 | 0.1256 |
| B73xM0271 | 0.3165 | 26.7932 | 175.57 | 27.5189 | 542.57 | 15.1669 | 173.63 | 0.1084 |
| B73xM0272 | 0.3237 | 28.2605 | 187.85 | 33.9213 | 664.94 | 18.7518 | 213.79 | 0.1175 |
| B73xM0273 | 0.2787 | 29.4772 | 173.91 | 36.9312 | 670.14 | 18.4207 | 183.73 | 0.1122 |
| B73xM0274 | 0.2798 | 27.5994 | 174.88 | 27.683 | 675.71 | 17.5946 | 189.52 | 0.09043 |
| B73xM0275 | 0.2874 | 30.9402 | 166.28 | 30.063 | 526.94 | 18.2897 | 147.02 | 0.1046 |
| B73xM0276 | 0.3236 | 27.6156 | 196.87 | 33.7596 | 668.55 | 16.2491 | 214.31 | 0.1023 |
| B73xM0279 | 0.2861 | 26.778 | 165.02 | 27.6829 | 583.08 | 17.4188 | 165.4 | 0.1411 |
| B73xM0280 | 0.3191 | 27.7502 | 181.72 | 30.3711 | 601.58 | 16.4054 | 191.74 | 0.1006 |
| B73xM0281 | 0.3379 | 27.0304 | 150.14 | 22.2799 | 323.55 | 17.1157 | 108.76 | 0.106 |
| B73xM0282 | 0.3071 | 26.8986 | 168.7 | 31.1155 | 521.61 | 15.8447 | 161.27 | 0.1282 |
| B73xM0283 | 0.3542 | 25.5225 | 188.49 | 30.2171 | 428.17 | 16.1189 | 151.66 | 0.125 |
| B73xM0284 | 0.3127 | 29.2253 | 204.36 | 35.1915 | 705.23 | 17.1835 | 220.57 | 0.1186 |
| B73xM0285 | 0.2916 | 25.0723 | 183.23 | 28.3587 | 509.45 | 14.2553 | 154.31 | 0.1092 |
| B73xM0286 | 0.3114 | 29.4138 | 183.93 | 38.4638 | 535.11 | 15.1666 | 166.54 | 0.1374 |

Figure 6E

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| B73xM0287 | 0.3156 | 28.4011 | 170.4 | 33.6796 | 586.69 | 17.8622 | 185.11 | 0.1096 |
| B73xM0288 | 0.3205 | 28.4301 | 167.56 | 34.1142 | 659.78 | 18.3706 | 211.57 | 0.1292 |
| B73xM0289 | 0.2927 | 25.4203 | 169.28 | 27.8567 | 604.27 | 15.6306 | 178.14 | 0.1449 |
| B73xM0290 | 0.3128 | 26.95 | 150.09 | 23.5011 | 450.39 | 17.1814 | 138.08 | 0.1181 |
| B73xM0291 | 0.2904 | 26.8935 | 174.32 | 26.5837 | 571.88 | 17.6587 | 164.89 | 0.1357 |
| B73xM0292 | 0.3541 | 25.4321 | 189.04 | 27.4875 | 545.89 | 14.3447 | 194.04 | 0.1343 |
| B73xM0293 | 0.332 | 27.8462 | 174.76 | 32.9004 | 580.58 | 14.9103 | 189.54 | 0.1198 |
| B73xM0294 | 0.2886 | 26.1008 | 161.07 | 29.3327 | 601.29 | 16.0655 | 172.58 | 0.07219 |
| B73xM0295 | 0.2958 | 25.7176 | 187.32 | 29.3254 | 627.99 | 16.3319 | 184.45 | 0.1497 |
| B73xM0296 | 0.3296 | 29.6499 | 197.73 | 41.5882 | 714.4 | 16.4873 | 235.34 | 0.1141 |
| B73xM0297 | 0.3115 | 29.6846 | 185.56 | 37.5406 | 678.79 | 18.0173 | 209.86 | 0.1246 |
| B73xM0298 | 0.2674 | 28.4756 | 144.28 | 26.2476 | 599.79 | 17.6553 | 159.7 | 0.1121 |
| B73xM0300 | 0.3277 | 28.5257 | 162.44 | 32.7923 | 472.58 | 16.0213 | 156.81 | 0.1163 |
| B73xM0303 | 0.3453 | 28.9924 | 210.22 | 38.6097 | 662.23 | 16.0191 | 228.29 | 0.09598 |
| B73xM0304 | 0.3393 | 28.4259 | 180.39 | 34.1712 | 564.36 | 16.6809 | 191.43 | 0.1016 |
| B73xM0305 | 0.3308 | 25.5716 | 180.22 | 29.7927 | 416.48 | 15.0709 | 139.39 | 0.1372 |
| B73xM0306 | 0.288 | 25.3048 | 120.48 | 31.6436 | 656.03 | 17.2622 | 190.64 | 0.1089 |
| B73xM0307 | 0.3044 | 28.3113 | 193.98 | 37.794 | 614.92 | 17.2148 | 186.35 | 0.1078 |
| B73xM0308 | 0.3464 | 26.5989 | 166.73 | 28.3454 | 573.97 | 16.2614 | 199.53 | 0.1139 |
| B73xM0309 | 0.316 | 25.9622 | 151.41 | 25.5766 | 476.56 | 17.2043 | 145.78 | 0.1097 |
| B73xM0310 | 0.2736 | 28.4564 | 175.71 | 32.4487 | 706.84 | 19.7402 | 195.29 | 0.1224 |
| B73xM0311 | 0.3359 | 22.938 | 145.64 | 23.9016 | 489.35 | 16.6497 | 154.2 | 0.1116 |
| B73xM0312 | 0.3039 | 26.3835 | 190.63 | 34.5391 | 609.14 | 15.7697 | 181.9 | 0.1047 |
| B73xM0313 | 0.3155 | 28.067 | 183.68 | 34.3448 | 675.12 | 15.9796 | 212.27 | 0.1475 |
| B73xM0317 | 0.297 | 26.3297 | 179.5 | 29.5773 | 578.46 | 15.3277 | 171.85 | 0.1177 |
| B73xM0318 | 0.264 | 26.5524 | 177.43 | 29.2277 | 661.98 | 16.5675 | 175.94 | 0.07965 |
| B73xM0320 | 0.3086 | 27.9755 | 181.56 | 31.979 | 602.49 | 16.7481 | 175.29 | 0.1123 |
| B73xM0321 | 0.303 | 28.0633 | 177.1 | 30.3868 | 588.67 | 18.203 | 177.95 | 0.1147 |
| B73xM0322 | 0.2641 | 26.8987 | 155.51 | 27.7175 | 624.02 | 18.186 | 169.18 | 0.1191 |
| B73xM0323 | 0.3226 | 28.8635 | 204.61 | 37.6709 | 750.13 | 16.1337 | 241.52 | 0.1686 |
| B73xM0324 | 0.3243 | 25.8175 | 167.44 | 24.6401 | 521.89 | 15.202 | 163.52 | 0.09345 |
| B73xM0325 | 0.303 | 28.4093 | 190.48 | 31.9898 | 548.66 | 16.9407 | 155.25 | 0.1031 |
| B73xM0326 | 0.2602 | 25.5118 | 172.47 | 28.2531 | 581.39 | 16.3532 | 157.32 | 0.1314 |
| B73xM0327 | 0.3232 | 26.5656 | 207.55 | 32.9789 | 647.05 | 16.2672 | 209.13 | 0.1341 |
| B73xM0328 | 0.2807 | 26.7385 | 178.87 | 31.5235 | 515.26 | 16.4145 | 161.04 | 0.1177 |
| B73xM0331 | 0.2931 | 26.5482 | 154.26 | 24.8157 | 531.58 | 16.897 | 155.89 | 0.08251 |
| B73xM0334 | 0.2312 | 27.3706 | 161 | 26.6431 | 635.38 | 17.2383 | 145.39 | 0.1012 |
| B73xM0335 | 0.3283 | 26.3083 | 179.7 | 29.3152 | 575.77 | 15.2975 | 179.46 | 0.1295 |
| B73xM0337 | 0.3308 | 28.6967 | 196.29 | 39.0613 | 615.87 | 15.9681 | 204.1 | 0.1327 |
| B73xM0338 | 0.2721 | 28.031 | 180.07 | 34.1153 | 663.25 | 15.7455 | 181.71 | 0.1191 |
| B73xM0339 | 0.2995 | 28.2237 | 176.54 | 28.2815 | 613.84 | 18.1075 | 180.64 | 0.08517 |
| B73xM0341 | 0.3036 | 30.6689 | 196.33 | 37.5288 | 659.5 | 18.5023 | 198.94 | 0.117 |
| B73xM0342 | 0.3096 | 24.6891 | 173.12 | 30.9744 | 616.93 | 17.538 | 190.4 | 0.1246 |
| B73xM0344 | 0.3172 | 26.3924 | 187.08 | 29.4612 | 552.66 | 14.83 | 172.13 | 0.09646 |

Figure 6F

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| B73xM0345 | 0.3171 | 26.5061 | 180.28 | 27.9696 | 509.05 | 15.1169 | 150.99 | 0.1221 |
| B73xM0348 | 0.2949 | 27.4685 | 182.04 | 34.795 | 620.2 | 16.2616 | 193.73 | 0.1025 |
| B73xM0350 | 0.3087 | 24.7334 | 174.95 | 25.0974 | 538.36 | 15.0196 | 165.16 | 0.1263 |
| B73xM0351 | 0.3344 | 25.7401 | 161.73 | 25.3787 | 511.76 | 15.4151 | 166.74 | 0.09494 |
| B73xM0352 | 0.2761 | 27.0146 | 183.03 | 27.4947 | 647.76 | 17.9662 | 178.02 | 0.1377 |
| B73xM0353 | 0.2759 | 25.7559 | 174.44 | 24.265 | 577.88 | 16.4364 | 159.06 | 0.1337 |
| B73xM0354 | 0.2996 | 23.7637 | 161.05 | 27.4284 | 551.4 | 15.6671 | 164.01 | 0.09784 |
| B73xM0355 | 0.3045 | 25.6376 | 156.57 | 23.3659 | 494.54 | 15.4797 | 149.72 | 0.1124 |
| B73xM0357 | 0.2847 | 26.6383 | 167.05 | 26.5775 | 546.6 | 16.3968 | 157.48 | 0.1305 |
| B73xM0358 | 0.2506 | 27.9086 | 179.9 | 31.9582 | 636.3 | 17.2415 | 159.21 | 0.08422 |
| B73xM0360 | 0.293 | 24.0473 | 185.76 | 29.2956 | 550.98 | 14.9053 | 158.23 | 0.09992 |
| B73xM0362 | 0.3005 | 26.1695 | 163.21 | 29.7265 | 537.07 | 16.6026 | 159.82 | 0.1495 |
| B73xM0364 | 0.2812 | 27.1628 | 154.68 | 24.2533 | 437.7 | 16.2855 | 124.95 | 0.1232 |
| B73xM0365 | 0.3077 | 28.8343 | 172.89 | 33.4321 | 614.01 | 17.8366 | 189.45 | 0.1183 |
| B73xM0366 | 0.2815 | 25.5312 | 159.38 | 24.765 | 540.27 | 15.7475 | 145.9 | 0.1349 |
| B73xM0368 | 0.2974 | 29.1424 | 189.46 | 36.5461 | 502.19 | 16.6059 | 146.7 | 0.1053 |
| B73xM0369 | 0.2982 | 26.9479 | 188.99 | 28.4609 | 561.94 | 15.8003 | 160.98 | 0.09845 |
| B73xM0370 | 0.2943 | 26.535 | 150.9 | 28.1706 | 468.55 | 18.1333 | 148.19 | 0.1441 |
| B73xM0375 | 0.3103 | 25.105 | 160.52 | 24.7678 | 480.94 | 15.6649 | 150.61 | 0.1376 |
| B73xM0376 | 0.3209 | 26.8237 | 196.17 | 31.8807 | 633.89 | 15.9095 | 204.26 | 0.1069 |
| B73xM0377 | 0.2961 | 28.782 | 173.5 | 33.2581 | 600.24 | 17.6525 | 175.97 | 0.09691 |
| B73xM0378 | 0.2748 | 24.8664 | 167.12 | 22.5344 | 580.63 | 16.1552 | 159.78 | 0.1111 |
| B73xM0379 | 0.2994 | 26.5627 | 183.48 | 27.9675 | 570.66 | 15.2963 | 166.89 | 0.1642 |
| B73xM0380 | 0.2986 | 27.2429 | 180.67 | 34.0894 | 530.04 | 16.3736 | 157.47 | 0.09916 |
| B73xM0381 | 0.3144 | 26.38 | 178.45 | 30.8369 | 635.15 | 16.2874 | 198.69 | 0.1139 |
| B73xM0382 | 0.2981 | 26.9467 | 169.29 | 29.7514 | 613.99 | 17.2047 | 182.3 | 0.1213 |
| B73xM0383 | 0.3071 | 27.6232 | 169.31 | 32.8994 | 514.14 | 16.9241 | 154.08 | 0.1424 |
| B73xM0384 | 0.3322 | 27.328 | 186.6 | 29.0853 | 570.97 | 15.8102 | 189.97 | 0.1282 |
| B73xMo17 | 0.3686 | 27.0825 | 218.9 | 37.6859 | 715.1 | 15.5183 | 263.34 | 0.1409 |
| M0001 | 0.2859 | 26.5275 | 163.4 | 29.3037 | 379.59 | 15.8634 | 107.61 | 0.1027 |
| M0002 | 0.2535 | 25.0224 | 174.59 | 21.9656 | 509.12 | 15.5334 | 128.28 | 0.08098 |
| M0004 | 0.2617 | 24.2016 | 142.61 | 16.7577 | 237.9 | 12.6328 | 57.7351 | 0.08767 |
| M0005 | 0.2973 | 22.524 | 156.19 | 11.7494 | 256.15 | 11.0841 | 75.1675 | 0.1015 |
| M0006 | 0.2344 | 22.167 | 169.66 | 13.4622 | 333.52 | 13.1674 | 80.1671 | 0.1104 |
| M0007 | 0.3274 | 21.8922 | 179.16 | 16.291 | 270.83 | 11.4289 | 92.3018 | 0.12 |
| M0008 | 0.2981 | 25.7724 | 158.15 | 20.9296 | 410.53 | 14.5868 | 128.81 | 0.1113 |
| M0010 | 0.248 | 21.8552 | 150.65 | 12.8625 | 401.88 | 16.3409 | 99.0361 | 0.1137 |
| M0011 | 0.2364 | 26.9029 | 132.66 | 25.7646 | 420.65 | 16.1073 | 99.5633 | 0.1061 |
| M0012 | 0.2504 | 26.5836 | 183.84 | 23.4692 | 447.7 | 14.2122 | 113.1 | 0.1027 |
| M0013 | 0.2308 | 24.4488 | 136.25 | 13.716 | 202.45 | 15.7473 | 44.6255 | 0.08065 |
| M0014 | 0.189 | 22.5688 | 125.25 | 13.1924 | 363.49 | 15.2973 | 64.5322 | 0.09663 |
| M0015 | 0.2778 | 23.3693 | 137.51 | 17.8851 | 221.44 | 13.8522 | 76.0938 | 0.07359 |
| M0016 | 0.287 | 26.3089 | 153.02 | 16.006 | 281.26 | 14.055 | 87.0992 | 0.1122 |
| M0017 | 0.2203 | 23.9912 | 151.12 | 21.4237 | 337.63 | 13.9718 | 72.343 | 0.1021 |

Figure 6G

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| M0021 | 0.2591 | 23.3531 | 161.65 | 18.3707 | 310.83 | 12.651 | 79.6367 | 0.08191 |
| M0022 | 0.2908 | 24.4618 | 131.67 | 20.8886 | 229.81 | 14.2061 | 73.2903 | 0.1173 |
| M0023 | 0.317 | 21.2198 | 129.33 | 10.2025 | 151.54 | 12.9122 | 49.0459 | 0.07695 |
| M0024 | 0.2994 | 22.6154 | 164.18 | 14.3621 | 212.98 | 11.7631 | 62.376 | 0.109 |
| M0025 | 0.2839 | 27.8531 | 158.63 | 27.7675 | 352.28 | 15.4104 | 101.68 | 0.1129 |
| M0026 | 0.3254 | 25.2948 | 166.7 | 29.612 | 247.25 | 12.2086 | 82.335 | 0.103 |
| M0027 | 0.201 | 23.6633 | 182.5 | 17.1417 | 301.5 | 11.4391 | 59.9703 | 0.09554 |
| M0028 | 0.2016 | 22.4483 | 175 | 15.0644 | 306.13 | 11.1023 | 58.9192 | 0.0707 |
| M0029 | 0.2561 | 24.3689 | 143.09 | 14.966 | 383 | 14.2288 | 97.4808 | 0.09568 |
| M0030 | 0.2463 | 27.1007 | 184.48 | 32.7004 | 378.52 | 15.0975 | 92.871 | 0.1085 |
| M0031 | 0.3142 | 24.6644 | 173.57 | 20.6894 | 403.92 | 13.3859 | 125.47 | 0.09347 |
| M0032 | 0.1884 | 19.7639 | 127.16 | 9.9865 | 177.43 | 12.6192 | 42.3785 | 0.08764 |
| M0033 | 0.263 | 24.9977 | 154.32 | 16.3065 | 402.51 | 14.065 | 99.1056 | 0.1011 |
| M0034 | 0.2501 | 26.3464 | 127.94 | 17.1388 | 429.21 | 17.6376 | 106.42 | 0.1171 |
| M0035 | 0.2013 | 23.2198 | 173.65 | 16.5518 | 354.56 | 11.8229 | 73.8062 | 0.09063 |
| M0039 | 0.2991 | 26.2617 | 149.39 | 18.6744 | 296.07 | 13.5751 | 88.2861 | 0.1062 |
| M0043 | 0.2678 | 22.9382 | 157.7 | 15.7541 | 210.29 | 13.4957 | 60.7891 | 0.1175 |
| M0044 | 0.2713 | 23.8873 | 148.08 | 15.2996 | 258.95 | 13.2594 | 72.6319 | 0.06983 |
| M0045 | 0.2998 | 24.4906 | 148.08 | 15.7007 | 256.98 | 16.0163 | 71.5428 | 0.08854 |
| M0046 | 0.2292 | 22.3172 | 159.87 | 18.6989 | 285.67 | 13.0815 | 62.2995 | 0.09217 |
| M0047 | 0.1725 | 17.6566 | 106.83 | 4.7874 | 180.41 | 11.8448 | 29.9731 | 0.113 |
| M0048 | 0.2751 | 21.9637 | 154.91 | 16.9762 | 250.68 | 12.7007 | 68.9864 | 0.09831 |
| M0051 | 0.2924 | 21.1691 | 150.77 | 14.6791 | 213.88 | 13.0475 | 64.495 | 0.1175 |
| M0052 | 0.2919 | 24.7592 | 131.2 | 16.4113 | 309.05 | 15.5298 | 90.0123 | 0.09701 |
| M0053 | 0.2234 | 24.5264 | 140.18 | 15.8915 | 293.79 | 14.0032 | 64.7039 | 0.1103 |
| M0054 | 0.2924 | 22.1781 | 114.74 | 12.8988 | 229.46 | 13.4909 | 69.6237 | 0.09956 |
| M0055 | 0.3094 | 22.6914 | 118.72 | 11.3372 | 87.883 | 12.0184 | 26.9349 | 0.07699 |
| M0056 | 0.2716 | 25.0242 | 151.81 | 23.6113 | 421.64 | 16.9971 | 104.04 | 0.07624 |
| M0057 | 0.2472 | 22.4621 | 148.09 | 11.635 | 131.18 | 12.5645 | 45.4588 | 0.1193 |
| M0058 | 0.1895 | 28.5992 | 157.97 | 23.6896 | 579.43 | 18.9307 | 107.7 | 0.06974 |
| M0059 | 0.2951 | 25.3905 | 124.03 | 18.5968 | 304.39 | 13.9891 | 84.486 | 0.09486 |
| M0060 | 0.2687 | 29.0303 | 139.37 | 25.0916 | 285.59 | 13.6876 | 77.2252 | 0.1335 |
| M0061 | 0.2931 | 23.3281 | 150.26 | 17.7468 | 270.05 | 13.3633 | 78.424 | 0.0718 |
| M0064 | 0.1964 | 18.934 | 90.8285 | 11.1326 | 84.7267 | 14.4195 | 23.74 | 0.09375 |
| M0065 | 0.2395 | 25.725 | 132.19 | 14.0144 | 407.73 | 16.8639 | 95.3189 | 0.1093 |
| M0066 | 0.274 | 28.3675 | 179.49 | 31.2097 | 645.37 | 18.0649 | 178.17 | 0.08598 |
| M0067 | 0.2827 | 24.4983 | 163.48 | 18.9464 | 248.02 | 13.5463 | 69.6642 | 0.1101 |
| M0069 | 0.2685 | 22.6097 | 169.03 | 17.0964 | 114.05 | 14.7572 | 27.4481 | 0.09321 |
| M0070 | 0.2418 | 23.0781 | 96.6753 | 6.0304 | 92.2261 | NA | 20.2684 | 0.08316 |
| M0071 | 0.2683 | 23.2672 | 123.56 | 12.71 | 215.34 | 13.8038 | 58.3381 | 0.1072 |
| M0075 | 0.2829 | 22.8851 | 134.98 | 16.2545 | 198.63 | 11.9685 | 55.2764 | 0.09211 |
| M0076 | 0.3214 | 28.0786 | 206.15 | 37.8131 | 321.8 | 15.756 | 102.75 | 0.09477 |
| M0077 | 0.3046 | 24.1432 | 173.32 | 23.7306 | 358.1 | 13.1668 | 106.73 | 0.09136 |
| M0078 | 0.3368 | 21.5595 | 98.2741 | 4.0161 | 32.9997 | NA | 8.4501 | 0.09814 |

Figure 6H

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| M0079 | 0.2593 | 21.3203 | 127.25 | 13.3125 | 198.24 | 11.8453 | 53.1082 | 0.08487 |
| M0080 | 0.2893 | 25.128 | 132.27 | 17.8868 | 224.63 | 13.8179 | 63.3734 | 0.07965 |
| M0081 | 0.225 | 22.9089 | 142.39 | 15.9411 | 206.13 | 13.3675 | 50.2079 | 0.1173 |
| M0084 | 0.3029 | 23.8157 | 174.44 | 18.9586 | 386.24 | 12.6672 | 116.57 | 0.08758 |
| M0085 | 0.2353 | 22.1271 | 140.91 | 16.8698 | 283.86 | 14.2126 | 63.076 | 0.09788 |
| M0086 | 0.2311 | 22.2386 | 133.06 | 12.4413 | 292.79 | 15.5366 | 68.6528 | 0.08611 |
| M0088 | 0.3651 | 26.7438 | 181.11 | 33.1899 | 295.46 | 13.5644 | 102.85 | 0.1012 |
| M0090 | 0.2182 | 24.2422 | 172.6 | 15.603 | 371.23 | 13.6735 | 78.8 | 0.08902 |
| M0091 | 0.248 | 24.2236 | 133.17 | 15.2619 | 345.19 | 13.35 | 84.3987 | 0.1248 |
| M0092 | 0.327 | 22.3842 | 131.36 | 9.6006 | 259.7 | 12.0058 | 84.4245 | 0.1048 |
| M0093 | 0.2489 | 19.5396 | 160.55 | 11.1804 | 98.6319 | 11.5858 | 28.1707 | 0.09603 |
| M0095 | 0.2661 | 25.3134 | 160.13 | 18.9746 | 313.39 | 14.9934 | 76.6449 | NA |
| M0096 | 0.2436 | 22.5936 | 156.69 | 16.3384 | 300.39 | 13.4669 | 73.9812 | 0.08309 |
| M0097 | 0.2924 | 24.5004 | 155.1 | 17.7738 | 287.4 | 15.1529 | 81.6988 | 0.1033 |
| M0098 | 0.265 | 23.914 | 166.49 | 17.7438 | 370.01 | 14.2842 | 96.179 | 0.09784 |
| M0099 | 0.2752 | 22.9851 | 141.52 | 13.451 | 75.3062 | 11.9508 | 15.0787 | 0.07973 |
| M0100 | 0.247 | 22.5553 | 126.4 | 13.0866 | 201.88 | 11.2424 | 47.8065 | 0.08921 |
| M0101 | 0.328 | 24.6646 | 168.52 | 13.8703 | 321.76 | 13.9883 | 93.0659 | 0.1018 |
| M0102 | 0.2439 | 25.8265 | 169.42 | 20.6363 | 397.93 | 15.7764 | 96.9806 | 0.1102 |
| M0103 | 0.3235 | 22.4454 | 157.61 | 16.4786 | 266.02 | 11.7772 | 84.7914 | 0.08916 |
| M0104 | 0.3953 | 23.4777 | 107.29 | 11.4332 | 105.62 | 12.5131 | 43.5235 | 0.1129 |
| M0105 | 0.2356 | 22.9109 | 123.63 | 14.6183 | 223.76 | 14.078 | 54.4597 | 0.08891 |
| M0106 | 0.2869 | 22.3824 | 140.36 | 14.0748 | 232.79 | 12.85 | 69.9457 | 0.08323 |
| M0107 | 0.286 | 23.8426 | 170.42 | 25.3622 | 362.95 | 12.2294 | 104.82 | 0.1095 |
| M0109 | 0.296 | 22.3234 | 154.36 | 14.3532 | 318.64 | 12.7715 | 93.7282 | 0.07047 |
| M0110 | 0.2557 | 24.0883 | 122.85 | 16.4222 | 211.39 | 14.1745 | 55.5573 | 0.09554 |
| M0113 | 0.2774 | 24.7637 | 126.93 | 14.3011 | 347.7 | 17.7239 | 91.4469 | 0.09517 |
| M0114 | 0.2202 | 23.4488 | 178.42 | 22.5342 | 430.37 | 16.1994 | 99.693 | 0.09644 |
| M0115 | 0.2643 | 24.3116 | 161.61 | 15.6634 | 276.1 | 14.0072 | 72.382 | 0.0569 |
| M0116 | 0.4229 | 24.1215 | 150.05 | 17.3071 | 221.26 | 12.2601 | 97.334 | 0.0927 |
| M0117 | 0.2548 | 23.6879 | 167.1 | 21.3718 | 315.08 | 13.9294 | 79.321 | 0.07776 |
| M0118 | 0.3094 | 23.4856 | 150.49 | 19.9839 | 298.45 | 13.4338 | 94.9023 | 0.1118 |
| M0120 | 0.3077 | 24.1701 | 142.91 | 14.9383 | 235.31 | 14.7471 | 68.2765 | 0.1238 |
| M0121 | 0.2947 | 23.2531 | 146.25 | 16.672 | 322.81 | 13.7735 | 92.5305 | 0.117 |
| M0122 | 0.344 | 24.6905 | 143.1 | 22.2401 | 354.16 | 14.5509 | 120.63 | 0.1179 |
| M0123 | 0.2666 | 20.3643 | 151.95 | 10.9315 | 307.01 | 12.5869 | 80.7945 | 0.0793 |
| M0124 | 0.272 | 23.278 | 143.76 | 12.9637 | 277.16 | 13.6973 | 76.8582 | 0.09104 |
| M0125 | 0.174 | 24.4815 | 192.44 | 20.4284 | -0.5694 | NA | 1.9865 | 0.1068 |
| M0126 | 0.2999 | 22.6849 | 174.64 | 16.1159 | 324.37 | 11.7972 | 95.3047 | 0.08604 |
| M0127 | 0.3236 | 22.9376 | 151.38 | 18.5907 | 184.64 | 11.3945 | 59.9061 | 0.08265 |
| M0129 | 0.2815 | 25.015 | 185.38 | 23.2868 | 348.99 | 12.3279 | 97.8501 | 0.07605 |
| M0130 | 0.2764 | 22.3304 | 154.67 | 15.0958 | 277.4 | 15.721 | 72.9826 | 0.08454 |
| M0131 | 0.2637 | 21.4115 | 137.38 | 9.3859 | 255.5 | 11.5356 | 68.1063 | 0.08768 |
| M0132 | 0.2973 | 22.8792 | 145.24 | 16.0097 | 293.05 | 12.5047 | 86.6732 | 0.1057 |

Figure 6I

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| M0133 | 0.2355 | 26.8214 | 139.03 | 21.1535 | 430.95 | 15.751 | 101.23 | 0.07656 |
| M0138 | 0.3069 | 21.8812 | 162.46 | 15.4647 | 341.85 | 11.6932 | 105.06 | 0.09558 |
| M0141 | 0.3351 | 24.6348 | 147.08 | 16.7322 | 377.46 | 13.1313 | 127.77 | 0.08619 |
| M0142 | 0.1914 | 22.6087 | 128.24 | 10.1443 | 221.6 | 15.1556 | 41.0717 | 0.07412 |
| M0143 | 0.2904 | 27.7878 | 155.39 | 25.1203 | 272.4 | 14.1642 | 73.5285 | 0.1077 |
| M0144 | 0.2534 | 26.4345 | 178.15 | 28.5502 | 439.72 | 14.9844 | 111.72 | 0.1035 |
| M0145 | 0.3008 | 27.0389 | 147.48 | 22.8189 | 293.23 | 17.4392 | 89.1915 | 0.09915 |
| M0147 | 0.2361 | 23.6199 | 142.72 | 13.7586 | 270.91 | 15.1489 | 54.9592 | 0.03079 |
| M0149 | 0.2805 | 24.5003 | 158.25 | 17.73 | 344.97 | 16.3996 | 95.2594 | 0.08291 |
| M0150 | 0.2624 | 20.7819 | 175.69 | 12.4784 | 326.96 | 11.9882 | 84.2676 | 0.08818 |
| M0151 | 0.2796 | 22.5235 | 122.55 | 11.0079 | 191.06 | 14.6918 | 49.7656 | 0.1077 |
| M0152 | 0.2856 | 23.6485 | 147.52 | 20.9886 | 218.67 | 13.7178 | 67.988 | 0.06919 |
| M0154 | 0.2781 | 23.0956 | 160.65 | 20.322 | 386.24 | 13.0572 | 106.68 | 0.1148 |
| M0155 | 0.3387 | 22.3971 | 162.54 | 16.1909 | 295.49 | 12.7174 | 100.48 | 0.09819 |
| M0156 | 0.2676 | 25.966 | 147.54 | 18.976 | 420.79 | 16.2135 | 112.57 | 0.1003 |
| M0157 | 0.221 | 25.4242 | 178 | 20.9785 | 501.17 | 15.0965 | 108.48 | 0.08377 |
| M0160 | 0.2578 | 24.4973 | 168.56 | 20.1651 | 349.07 | 14.9743 | 88.1645 | 0.1442 |
| M0160A | 0.234 | 22.7732 | 104.3 | 10.293 | 107.26 | 14.4948 | 28.3732 | 0.1049 |
| M0161 | 0.3 | 24.5162 | 177.06 | 25.364 | 394.93 | 13.2466 | 116.72 | 0.1051 |
| M0162 | 0.2824 | 23.7718 | 159.54 | 17.5691 | 360.68 | 13.7528 | 102.67 | 0.0855 |
| M0162A | 0.2741 | 23.1639 | 173.19 | 20.545 | 315.45 | 16.0423 | 82.891 | 0.1118 |
| M0163 | 0.3136 | 25.5557 | 167.88 | 21.327 | 295.52 | 15.2653 | 88.1606 | 0.1405 |
| M0165 | 0.353 | 26.479 | 146.28 | 21.6739 | 383.93 | 16.7001 | 134.71 | 0.1161 |
| M0166 | 0.3115 | 23.1835 | 135.16 | 13.3274 | 178.79 | 11.9103 | 52.0216 | 0.09636 |
| M0167 | 0.2133 | 23.7222 | 130.36 | 14.575 | 305.14 | 16.3598 | 61.2503 | 0.1117 |
| M0168 | 0.2528 | 24.7619 | 164.38 | 22.8153 | 366.44 | 14.4128 | 94.6361 | 0.0767 |
| M0169 | 0.2894 | 27.0406 | 148.28 | 25.951 | 410.3 | 15.8246 | 116.71 | 0.09872 |
| M0173 | 0.4405 | 24.4726 | 123.04 | 14.2713 | 71.2676 | 13.8858 | 29.2501 | 0.07875 |
| M0174 | 0.2909 | 25.1809 | 180.29 | 24.8375 | 331.95 | 13.6561 | 94.1663 | 0.09403 |
| M0176 | 0.292 | 23.9799 | 137.02 | 17.2898 | 320.46 | 15.294 | 94.2035 | 0.08712 |
| M0177 | 0.2657 | 25.4704 | 176.04 | 23.0073 | 349.43 | 15.077 | 101.88 | 0.09434 |
| M0178 | 0.2492 | 25.2263 | 137.95 | 18.3988 | 396.13 | 16.0093 | 97.3767 | 0.09635 |
| M0179 | 0.2902 | 24.0576 | 170.56 | 16.8995 | 327.82 | 11.9587 | 94.6252 | 0.092 |
| M0180 | 0.2919 | 22.8705 | 162.28 | 16.442 | 374.74 | 13.5485 | 108.21 | 0.1347 |
| M0181 | 0.311 | 24.5617 | 163.63 | 20.7001 | 256.84 | 14.876 | 80.6009 | 0.0804 |
| M0185 | 0.2911 | 24.0986 | 141.05 | 17.0724 | 317.47 | 14.5066 | 91.5705 | 0.1214 |
| M0187 | 0.2653 | 27.1713 | 128.56 | 17.6086 | 334.19 | 15.808 | 84.7787 | 0.0639 |
| M0188 | 0.2841 | 27.8481 | 163.77 | 23.3796 | 303.07 | 14.8145 | 86.8909 | 0.1142 |
| M0189 | 0.2773 | 25.3578 | 152.47 | 25.9437 | 423.74 | 16.3155 | 130.98 | 0.07599 |
| M0191 | 0.3113 | 23.7849 | 133.85 | 16.2401 | 251.39 | 12.544 | 77.3162 | 0.1054 |
| M0192 | 0.1874 | 28.6134 | 148.54 | 19.1835 | 305.84 | 19.6274 | 65.5879 | 0.0724 |
| M0194 | 0.2666 | 27.0868 | 161.53 | 20.5639 | 270.29 | 16.8239 | 79.1942 | 0.08731 |
| M0195 | 0.2366 | 25.2539 | 116.37 | 16.1128 | 46.4946 | NA | 13.6894 | 0.0936 |
| M0196 | 0.291 | 25.3522 | 140.1 | 13.0056 | 128.08 | 14.6225 | 32.4887 | 0.1167 |

Figure 6J

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| M0197 | 0.2796 | 25.8741 | 137.86 | 20.9658 | 246.14 | 15.6678 | 67.1649 | 0.08431 |
| M0198 | 0.3059 | 24.2436 | 177.27 | 22.0155 | 423.88 | 13.3227 | 130.08 | 0.09647 |
| M0199 | 0.1695 | 18.596 | 107.12 | 7.0855 | 118.15 | 12.0171 | 29.6543 | 0.1065 |
| M0200 | 0.2613 | 25.316 | 188.94 | 26.2854 | 415.29 | 14.0445 | 103.7 | 0.09531 |
| M0201 | 0.2761 | 21.596 | 149.72 | 17.824 | 357.73 | 19.6372 | 111.92 | 0.1141 |
| M0203 | 0.2956 | 25.8442 | 170.02 | 23.088 | 305.36 | 15.4349 | 89.6992 | 0.1084 |
| M0204 | 0.2429 | 22.7629 | 132.92 | 14.9541 | 332.76 | 13.105 | 84.5998 | 0.1118 |
| M0205 | 0.2452 | 27.0949 | 184.74 | 26.1236 | 493.62 | 16.0734 | 118.1 | 0.09942 |
| M0206 | 0.2907 | 23.4411 | 163.68 | 17.5708 | 194.02 | 13.4001 | 54.393 | 0.1442 |
| M0208 | 0.3218 | 23.5785 | 129.17 | 14.9614 | 208.28 | 16.3418 | 62.3054 | 0.07286 |
| M0209 | 0.2823 | 23.6946 | 137.6 | 16.2824 | 216.93 | 14.2696 | 61.3386 | 0.09693 |
| M0210 | 0.2527 | 22.7121 | 185.74 | 19.7967 | 324.14 | 11.9709 | 79.7276 | 0.1344 |
| M0212 | 0.2914 | 23.6281 | 179.39 | 19.0141 | 378.81 | 12.5711 | 113.24 | 0.07946 |
| M0213 | 0.306 | 24.9787 | 159.31 | 21.1388 | 313.9 | 13.0931 | 96.6459 | 0.08223 |
| M0214 | 0.1958 | 22.5043 | 163.49 | 16.506 | 369.61 | 15.1405 | 73.9868 | 0.09511 |
| M0215 | 0.3184 | 26.5356 | 182.38 | 31.2732 | 419.18 | 14.3057 | 132.71 | 0.09726 |
| M0216 | 0.2807 | 24.0593 | 153.22 | 17.8502 | 343.01 | 12.4833 | 95.7728 | 0.1173 |
| M0217 | 0.2214 | 25.9141 | 136.37 | 18.1588 | 364.88 | 15.7945 | 76.6421 | 0.07422 |
| M0218 | 0.2549 | 22.8324 | 123.44 | 10.0161 | 226.22 | 14.3533 | 55.9293 | 0.09818 |
| M0219 | 0.2867 | 23.073 | 163.88 | 15.7817 | 280.13 | 13.7511 | 79.4692 | 0.1074 |
| M0220 | 0.2687 | 25.7242 | 150.15 | 21.6532 | 379.39 | 17.8043 | 100.58 | 0.118 |
| M0222 | 0.2906 | 24.6608 | 137.38 | 14.8736 | 370.83 | 15.4975 | 106.3 | 0.09854 |
| M0223 | 0.2999 | 24.7085 | 145.35 | 24.1285 | 334.38 | 15.3013 | 106.41 | 0.08922 |
| M0225 | 0.2185 | 24.2067 | 130.1 | 15.3847 | 91.3228 | 14.1201 | 20.8435 | 0.1178 |
| M0228 | 0.2902 | 21.6925 | 122.99 | 11.1139 | 163.15 | 14.9936 | 44.3065 | 0.1037 |
| M0229 | 0.2451 | 25.1746 | 154.08 | 18.518 | 407.31 | 16.1138 | 98.8235 | 0.0844 |
| M0230 | 0.3046 | 25.3017 | 172.92 | 20.3339 | 277.55 | 11.0514 | 81.2427 | 0.09568 |
| M0232 | 0.3434 | 23.7381 | 151.18 | 16.8803 | 291.07 | 14.3209 | 100.57 | 0.1227 |
| M0233 | 0.2041 | 24.935 | 134.74 | 19.5714 | 402.38 | 16.266 | 81.7721 | 0.08616 |
| M0234 | 0.2651 | 24.322 | 147.17 | 15.5038 | 340.03 | 15.5862 | 89.6195 | 0.07116 |
| M0235 | 0.2489 | 22.2236 | 160.42 | 18.8799 | 341.04 | 14.7294 | 84.7369 | 0.1107 |
| M0236 | 0.2864 | 24.004 | 147.09 | 18.4507 | 317.24 | 12.9094 | 90.5313 | 0.06173 |
| M0238 | 0.1827 | 19.4856 | 137.9 | 12.7126 | 33.3034 | 15.8872 | 11.3099 | 0.09811 |
| M0239 | 0.2529 | 29.0872 | 150.33 | 22.1421 | 464.59 | 16.3794 | 108.5 | NA |
| M0240 | 0.1866 | 24.1024 | 134.25 | 15.4556 | 486.94 | 15.5183 | 90.311 | 0.068 |
| M0241 | 0.2842 | 21.4682 | 119.44 | 18.0323 | 336.16 | 14.733 | 95.072 | 0.1116 |
| M0244 | 0.2478 | 23.135 | 113.51 | 11.5728 | 221.43 | 13.3861 | 53.8798 | NA |
| M0245 | 0.2692 | 29.8548 | 182.37 | 33.0054 | 452.54 | 14.7033 | 121.13 | 0.0883 |
| M0248 | 0.2554 | 21.334 | 162.26 | 14.6516 | 174.71 | 13.5687 | 54.9607 | 0.09039 |
| M0249 | 0.2919 | 24.3405 | 145.54 | 19.1235 | 323.42 | 14.8754 | 86.199 | 0.1339 |
| M0251 | 0.276 | 22.9278 | 116.18 | 12.7908 | 201.06 | 14.4239 | 50.179 | 0.09623 |
| M0252 | 0.2449 | 26.7228 | 152.17 | 20.6855 | 360.89 | 15.9236 | 91.3011 | 0.09373 |
| M0254 | 0.2304 | 24.011 | 149.1 | 17.0301 | 401.72 | 14.5892 | 82.1079 | 0.1149 |
| M0256 | 0.3086 | 29.5521 | 151.37 | 24.894 | 269.09 | 16.9634 | 77.1051 | 0.1009 |

Figure 6K

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| M0257 | 0.2999 | 24.1846 | 170.37 | 17.1247 | 359.34 | 13.8396 | 109.45 | 0.07295 |
| M0258 | 0.1866 | 21.1554 | 146.52 | 18.1995 | 500.13 | 16.6051 | 96.127 | 0.1102 |
| M0259 | 0.3563 | 26.2594 | 155.51 | 22.8052 | 344.77 | 15.0984 | 121.2 | 0.08977 |
| M0260 | 0.2976 | 25.2391 | 160.1 | 20.5632 | 308.89 | 12.358 | 91.4414 | 0.06664 |
| M0262 | 0.28 | 23.3619 | 133.93 | 14.2789 | 229.79 | 13.4658 | 62.3412 | 0.1131 |
| M0263 | 0.2423 | 24.1342 | 139.09 | 16.9829 | 382.41 | 17.4087 | 81.2054 | 0.09423 |
| M0264 | 0.2215 | 25.7326 | 146.36 | 20.1822 | 419.44 | 15.855 | 93.5209 | 0.08673 |
| M0265 | 0.2673 | 24.9552 | 122.65 | 16.4177 | 331.47 | 15.4946 | 87.1081 | 0.07195 |
| M0266 | 0.244 | 25.699 | 152.52 | 21.6261 | 482.04 | 16.9069 | 117.78 | 0.1162 |
| M0267 | 0.2334 | 25.3185 | 158.34 | 20.6625 | 424.93 | 16.2458 | 98.4339 | 0.1119 |
| M0269 | 0.2262 | 22.6754 | 128.97 | 11.7433 | 169.56 | 13.4445 | 36.7842 | 0.0792 |
| M0270 | 0.2415 | 26.6402 | 179.84 | 27.9354 | 123.61 | 14.0928 | 45.4136 | 0.07657 |
| M0271 | 0.3039 | 23.6061 | 147.13 | 15.9189 | 298.72 | 14.2944 | 92.7942 | 0.09701 |
| M0272 | 0.2607 | 23.0575 | 146.55 | 17.8069 | 326.2 | 17.0172 | 82.5903 | 0.09348 |
| M0273 | 0.2724 | 28.319 | 139.81 | 28.3417 | 445.59 | 16.5044 | 120.12 | 0.08418 |
| M0274 | 0.2223 | 24.3487 | 156.72 | 17.2633 | 460.25 | 15.9013 | 104.32 | 0.0726 |
| M0275 | 0.2607 | 30.7555 | 154.12 | 21.912 | 422.68 | 19.7781 | 104.83 | 0.08412 |
| M0276 | 0.2911 | 23.0438 | 176.83 | 19.8375 | 378.6 | 14.1165 | 109.14 | 0.1083 |
| M0279 | 0.2417 | 22.2687 | 110.1 | 9.4424 | 19.4112 | 12.3061 | 3.7686 | 0.09919 |
| M0280 | 0.2795 | 23.8347 | 164.39 | 18.251 | 349.37 | 12.983 | 95.5819 | 0.1001 |
| M0281 | 0.2751 | 22.753 | 133.04 | 7.3662 | 29.8277 | NA | 10.9731 | 0.05963 |
| M0282 | 0.2954 | 21.7818 | 134.37 | 16.2371 | 158.55 | 13.2619 | 46.6278 | 0.1161 |
| M0283 | 0.1828 | 18.9353 | 109.98 | 8.3272 | 0.5002 | NA | 2.5462 | 0.09509 |
| M0284 | 0.246 | 27.2197 | 181.48 | 21.5533 | 452.76 | 16.6071 | 104.7 | 0.1054 |
| M0285 | 0.2798 | 23.0453 | 191.64 | 21.419 | 283.23 | 12.2523 | 84.4461 | 0.08449 |
| M0286 | 0.2445 | 21.9973 | 135.04 | 13.5616 | 37.5775 | 12.8111 | 9.6769 | 0.1158 |
| M0287 | 0.3297 | 25.47 | 136.84 | 22.6845 | 295.87 | 15.5608 | 88.223 | 0.08502 |
| M0288 | 0.3349 | 25.445 | 143.13 | 19.1967 | 393.11 | 16.4407 | 130.82 | 0.09806 |
| M0289 | 0.2583 | 21.864 | 146.81 | 15.1897 | 366.86 | 12.6921 | 93.6425 | 0.0759 |
| M0290 | 0.2908 | 24.1468 | 148.51 | 18.2635 | 337.09 | 14.5896 | 96.4849 | 0.1101 |
| M0291 | 0.2655 | 24.8609 | 172.08 | 20.9066 | 438.29 | 15.2894 | 114.91 | 0.08267 |
| M0292 | 0.3396 | 22.3407 | 149.56 | 14.6731 | 225.42 | 10.5492 | 78.5753 | 0.1011 |
| M0293 | 0.3267 | 25.6775 | 146.92 | 20.5833 | 354.77 | 13.3144 | 116.01 | 0.1117 |
| M0294 | 0.2229 | 20.7723 | 115.8 | 12.8441 | 305.68 | 14.4636 | 70.6006 | 0.08844 |
| M0295 | 0.2442 | 22.7898 | 151.19 | 15.6862 | 364.97 | 13.4814 | 85.424 | 0.09211 |
| M0296 | 0.2958 | 25.2823 | 154.71 | 21.0685 | 262.85 | 13.1573 | 75.9461 | 0.06002 |
| M0297 | 0.2728 | 25.4376 | 146.77 | 19.9809 | 416.55 | 16.1897 | 113.08 | 0.1213 |
| M0298 | 0.2201 | 25.6057 | 148.09 | 17.1711 | 418.62 | 16.5921 | 89.9993 | 0.1069 |
| M0300 | 0.3349 | 24.4955 | 129.32 | 21.7224 | 255.19 | 14.0276 | 85.7386 | 0.07172 |
| M0303 | 0.2716 | 23.3641 | 145.01 | 15.3916 | 247.49 | 13.6487 | 73.5629 | 0.09915 |
| M0304 | 0.2711 | 21.6892 | 105.17 | 17.2965 | 188.73 | 12.0782 | 53.108 | 0.08716 |
| M0305 | 0.1539 | 19.7708 | 132.8 | 8.9658 | 120.5 | 13.0736 | 21.7325 | 0.05864 |
| M0306 | 0.247 | NA | NA | 15.7372 | 286.49 | 14.0441 | 71.8338 | 0.1064 |
| M0307 | 0.2318 | 26.297 | 152.05 | 21.9639 | 304.04 | 15.294 | 66.4026 | 0.06978 |

Figure 6L

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| M0308 | 0.2148 | 18.0556 | 98.3949 | 4.0783 | -3.2975 | NA | -2.1399 | 0.08526 |
| M0309 | 0.336 | 23.8272 | 155.51 | 19.8353 | 317.58 | 15.2499 | 103.93 | 0.09775 |
| M0310 | 0.2033 | 24.7179 | 145.11 | 18.6061 | 388.39 | 15.948 | 80.1751 | 0.07343 |
| M0311 | 0.2527 | 21.9354 | 116.89 | 11.8732 | 322.32 | 14.7487 | 80.5793 | 0.0909 |
| M0312 | 0.2514 | 24.5045 | 178.5 | 30.3517 | 446.71 | 13.9341 | 111.51 | 0.1287 |
| M0313 | 0.3161 | 23.5864 | 134.3 | 16.9848 | 301.22 | 12.2671 | 95.5243 | 0.09755 |
| M0317 | 0.2713 | 23.4783 | 173.91 | 19.1884 | 379.63 | 12.3361 | 101.24 | 0.09572 |
| M0318 | 0.2233 | 22.941 | 153.43 | 15.748 | 344.55 | 14.4618 | 72.5104 | 0.09028 |
| M0320 | 0.2645 | 25.4018 | 173.43 | 23.4696 | 422.93 | 14.4893 | 110.51 | 0.09993 |
| M0321 | 0.3049 | 25.4205 | 152.58 | 20.0155 | 428.4 | 16.7179 | 129.33 | 0.1137 |
| M0322 | 0.2397 | 22.5943 | 115.75 | 14.3837 | 279.21 | 15.1023 | 64.0657 | 0.06259 |
| M0323 | 0.2573 | 23.4904 | 165.54 | 17.0118 | 379.32 | 13.4905 | 97.8744 | 0.1034 |
| M0324 | 0.3378 | 23.729 | 137.31 | 14.7897 | 146.97 | 13.633 | 49.5278 | 0.08131 |
| M0325 | 0.2513 | 24.3216 | 175.01 | 22.1197 | 404.39 | 15.2 | 106.63 | 0.09303 |
| M0326 | 0.1215 | 21.0013 | 129.23 | 12.2605 | 204.7 | 13.7591 | 33.541 | 0.1023 |
| M0327 | 0.2771 | 22.8367 | 179.48 | 17.1804 | 366.12 | 14.5507 | 102.42 | 0.1122 |
| M0328 | 0.2956 | 24.6435 | 147.45 | 19.5209 | 316.44 | 13.8742 | 93.456 | 0.09241 |
| M0331 | 0.2929 | 24.2381 | 143.08 | 16.7121 | 293.41 | 14.6447 | 81.5889 | 0.1039 |
| M0334 | 0.2231 | 24.8902 | 144.62 | 16.5623 | 366.16 | 15.1734 | 78.4779 | 0.09752 |
| M0335 | 0.2946 | 22.7087 | 156.31 | 17.075 | 312.34 | 12.6934 | 91.311 | 0.108 |
| M0337 | 0.2677 | 23.6878 | 134.48 | 22.174 | 228.6 | 12.3852 | 76.5458 | 0.1089 |
| M0338 | 0.2468 | 25.4218 | 182.96 | 26.2111 | 447.01 | 13.9813 | 109.64 | 0.1277 |
| M0339 | 0.2306 | 24.9967 | 119.47 | 14.8356 | 417.92 | 17.1087 | 96.3156 | 0.1056 |
| M0341 | 0.2095 | 25.2423 | 134.7 | 17.2159 | 246.13 | 14.3852 | 63.7765 | 0.0946 |
| M0342 | 0.2872 | 21.0225 | 117.71 | 12.1551 | 197.33 | 13.3427 | 55.6466 | 0.0865 |
| M0344 | 0.2833 | 22.8881 | 169.36 | 16.7086 | 185.76 | 12.4144 | 55.9101 | 0.07709 |
| M0345 | 0.3281 | 23.3266 | 176.84 | 18.5327 | 242.13 | 12.651 | 81.166 | 0.1058 |
| M0348 | 0.3028 | 23.4779 | 151.55 | 17.9803 | 255.41 | 12.0374 | 69.4963 | 0.07294 |
| M0350 | 0.3151 | 20.747 | 150.72 | 11.5342 | 126.07 | 11.6767 | 39.0418 | 0.1128 |
| M0351 | 0.2721 | 22.2649 | 116.47 | 11.6929 | 186.38 | 12.8964 | 54.5875 | 0.08234 |
| M0352 | 0.2209 | 24.9655 | 170.84 | 18.8996 | 451.94 | 16.6239 | 102.53 | 0.1062 |
| M0353 | 0.2472 | 23.5305 | 167.47 | 18.9834 | 427.11 | 16.0773 | 105.08 | 0.06816 |
| M0354 | 0.2534 | 20.8977 | 125.89 | 13.7156 | 263.13 | 14.1823 | 68.2192 | 0.0964 |
| M0355 | 0.2648 | 21.331 | 130.23 | 9.4724 | 117.19 | 12.3511 | 30.8181 | 0.09217 |
| M0357 | 0.2072 | 23.5229 | 140.98 | 12.5535 | 294.61 | 13.6932 | 61.2388 | 0.08476 |
| M0358 | 0.2416 | 25.6616 | 160.84 | 22.9718 | 363.8 | 15.9111 | 80.15 | 0.06746 |
| M0360 | 0.2663 | 20.1478 | 168.61 | 19.1287 | 273.3 | 11.9379 | 68.7346 | 0.07339 |
| M0362 | 0.3369 | 22.9738 | 107.89 | 12.7632 | 123.9 | 14.0382 | 49.0688 | 0.07848 |
| M0364 | 0.2373 | 23.0419 | 126.64 | 13.4366 | 292.42 | 15.1136 | 68.0475 | 0.1186 |
| M0365 | 0.2302 | 25.4783 | 116.4 | 16.4065 | 242.19 | 16.8469 | 69.2058 | 0.1116 |
| M0366 | 0.2445 | 22.963 | 151.16 | 15.3707 | 255.77 | 12.4324 | 60.2635 | 0.11 |
| M0368 | 0.2954 | 27.5083 | 176.59 | 26.7901 | 412.2 | 13.8774 | 120.2 | 0.108 |
| M0369 | 0.257 | 23.6922 | 178.92 | 19.8305 | 414.55 | 14.3088 | 105.02 | 0.1009 |
| M0370 | 0.3107 | 25.1501 | 122.61 | 19.4652 | 316.89 | 16.1093 | 100.02 | 0.1381 |

Figure 6M

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| M0375 | 0.2471 | 23.4912 | 130.3 | 13.049 | 216.51 | 13.2534 | 54.389 | 0.08939 |
| M0376 | 0.2503 | 21.6615 | 175.62 | 18.8457 | 368.66 | 12.2868 | 106.93 | 0.08762 |
| M0377 | 0.2186 | 25.2985 | 126.09 | 14.5483 | 320.82 | 15.2463 | 67.0258 | 0.08628 |
| M0378 | 0.2396 | 20.8781 | 137.05 | 11.5684 | 257.17 | 13.8212 | 63.7104 | 0.1103 |
| M0379 | 0.2393 | 22.5358 | 168.45 | 13.5531 | 204.11 | 12.0108 | 45.5712 | 0.09987 |
| M0380 | 0.2577 | 22.4476 | 142.49 | 15.0271 | 180.48 | 12.2394 | 48.7967 | 0.1023 |
| M0381 | 0.3089 | 22.9861 | 126.77 | 12.883 | 257.87 | 12.5015 | 79.5759 | 0.1336 |
| M0382 | 0.2581 | 23.352 | 161.71 | 18.4483 | 365.83 | 14.7327 | 92.6613 | 0.08547 |
| M0383 | 0.282 | 24.8245 | 135.05 | 22.6208 | 267.83 | 13.2136 | 74.1625 | 0.08242 |
| M0384 | 0.2434 | 21.1185 | 150.64 | 12.6687 | 77.7311 | 12.1523 | 27.1647 | 0.1165 |
| Mo17 | 0.326 | 21.3603 | 176.58 | 16.1485 | 221.03 | 10.8271 | 75.1197 | 0.101 |
| Mo17xB73 | 0.3717 | 27.3749 | 221.64 | 39.126 | 733.22 | 15.5605 | 273.35 | 0.1494 |
| Mo17xM0001 | 0.3292 | 25.589 | 199 | 32.7715 | 519.97 | 13.5329 | 172.96 | 0.124 |
| Mo17xM0002 | 0.3343 | 24.2291 | 213.17 | 29.2144 | 579.9 | 13.6167 | 195.26 | 0.1263 |
| Mo17xM0004 | 0.3369 | 23.1065 | 185.82 | 20.6828 | 444.37 | 11.5294 | 150.73 | 0.1097 |
| Mo17xM0005 | 0.3288 | 23.6078 | 198.31 | 21.4266 | 515.37 | 12.1683 | 179.02 | 0.1347 |
| Mo17xM0006 | 0.3118 | 22.9798 | 204.33 | 19.91 | 483.94 | 11.7846 | 152.31 | 0.1296 |
| Mo17xM0007 | 0.3923 | 25.9142 | 214.16 | 27.8323 | 448.03 | 12.1219 | 175.86 | 0.108 |
| Mo17xM0008 | 0.3672 | 25.732 | 218.74 | 27.7176 | 581.4 | 13.0197 | 213.07 | 0.1158 |
| Mo17xM0010 | 0.3108 | 22.6415 | 193.66 | 18.3836 | 503.88 | 13.7138 | 154.14 | 0.1094 |
| Mo17xM0011 | 0.3576 | 25.2476 | 209.69 | 35.1643 | 519.93 | 12.1703 | 184.78 | 0.1246 |
| Mo17xM0012 | 0.3473 | 25.74 | 226.03 | 29.8849 | 587.2 | 13.5967 | 200.69 | 0.145 |
| Mo17xM0013 | 0.3061 | 24.3326 | 204.21 | 25.9327 | 583.8 | 13.4829 | 178.87 | 0.1237 |
| Mo17xM0014 | 0.3304 | 23.3643 | 178.57 | 22.8779 | 406.62 | 12.7537 | 128.66 | 0.1051 |
| Mo17xM0015 | 0.3696 | 24.6068 | 205.54 | 26.9565 | 539 | 12.8157 | 197.71 | 0.1223 |
| Mo17xM0016 | 0.3412 | 25.2775 | 217.76 | 34.8172 | 574.72 | 12.3185 | 196.42 | 0.1365 |
| Mo17xM0017 | 0.3311 | 23.6853 | 208.88 | 29.5142 | 525.57 | 12.8115 | 174.38 | 0.1159 |
| Mo17xM0021 | 0.3212 | 24.0545 | 191.36 | 23.1916 | 528.93 | 13.0968 | 171.96 | 0.1435 |
| Mo17xM0022 | 0.3632 | 25.5703 | 185.19 | 26.5524 | 416.01 | 13.4936 | 159.91 | 0.1323 |
| Mo17xM0023 | 0.3483 | 23.7251 | 212.7 | 23.4047 | 496.82 | 12.5753 | 170.22 | 0.1132 |
| Mo17xM0024 | 0.3168 | 22.1523 | 184.82 | 18.5635 | 347.74 | 11.1383 | 104.14 | 0.131 |
| Mo17xM0025 | 0.3406 | 26.3005 | 210.13 | 32.8748 | 594.03 | 13.6484 | 202.73 | 0.143 |
| Mo17xM0026 | 0.3606 | 25.5119 | 201.67 | 31.068 | 491.98 | 13.0436 | 176.53 | 0.127 |
| Mo17xM0027 | 0.3668 | 23.8429 | 211.26 | 24.4733 | 472.84 | 11.7812 | 175.03 | 0.1447 |
| Mo17xM0028 | 0.3122 | 22.1078 | 186.21 | 21.5075 | 449.72 | 12.5868 | 144.8 | 0.1256 |
| Mo17xM0029 | 0.3621 | 24.4093 | 212.2 | 25.4608 | 543.55 | 13.21 | 196.08 | 0.1172 |
| Mo17xM0030 | 0.3172 | 24.044 | 189.07 | 28.8641 | 424.81 | 13.6589 | 153.17 | 0.1395 |
| Mo17xM0031 | 0.3755 | 24.7297 | 210.79 | 28.1814 | 539.62 | 13.3295 | 202.79 | 0.1222 |
| Mo17xM0032 | 0.3766 | 24.4955 | 214.09 | 26.9437 | 457.1 | 12.0422 | 170.9 | 0.1068 |
| Mo17xM0033 | 0.3623 | 24.4479 | 211.2 | 25.2707 | 517.79 | 12.3109 | 184.8 | 0.1279 |
| Mo17xM0034 | 0.3373 | 27.3267 | 212.64 | 32.8029 | 714.93 | 15.6426 | 240.91 | 0.1427 |
| Mo17xM0035 | 0.3613 | 24.2225 | 227.57 | 26.1711 | 562.15 | 11.9854 | 201.61 | 0.1301 |
| Mo17xM0039 | 0.3857 | 25.9037 | 204.6 | 29.632 | 495.67 | 12.503 | 193.37 | 0.1125 |
| Mo17xM0043 | 0.3575 | 25.0735 | 206.35 | 28.0295 | 578.71 | 13.9351 | 204.83 | 0.2042 |

Figure 6N

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| Mo17xM0044 | 0.3112 | 24.0249 | 196.42 | 22.2211 | 473.24 | 12.5285 | 150.9 | 0.08299 |
| Mo17xM0045 | 0.3475 | 24.6216 | 209.83 | 24.2972 | 576.46 | 13.1947 | 199.34 | 0.09709 |
| Mo17xM0046 | 0.2982 | 20.769 | 175.13 | 20.3448 | 298.51 | 12.4337 | 90.8952 | 0.08974 |
| Mo17xM0047 | 0.3538 | 23.3071 | 203.88 | 19.8693 | 524.29 | 13.0451 | 185.93 | 0.1267 |
| Mo17xM0048 | 0.3472 | 22.7637 | 178.25 | 21.2321 | 352.04 | 12.1082 | 122.93 | 0.1209 |
| Mo17xM0051 | 0.3719 | 23.4592 | 205.5 | 26.2278 | 501.55 | 13.8278 | 186.03 | 0.1336 |
| Mo17xM0052 | 0.3341 | 21.8504 | 166.77 | 18.5544 | 332.24 | 12.5264 | 116.54 | 0.1483 |
| Mo17xM0053 | 0.3142 | 22.818 | 160.68 | 18.3705 | 339.75 | 13.1865 | 113.24 | 0.1251 |
| Mo17xM0054 | 0.3544 | 25.447 | 206.79 | 22.9819 | 540.94 | 13.9056 | 193.69 | 0.1554 |
| Mo17xM0055 | 0.3634 | 26.1258 | 202.25 | 28.7379 | 592.02 | 12.9075 | 214.6 | 0.1192 |
| Mo17xM0056 | 0.3186 | 24.3639 | 210.47 | 29.3755 | 614.21 | 14.2249 | 197.72 | 0.1178 |
| Mo17xM0057 | 0.3497 | 25.9589 | 228.08 | 28.6389 | 518.03 | 12.9247 | 193.68 | 0.1204 |
| Mo17xM0058 | 0.331 | 26.4322 | 210 | 31.2761 | 623.97 | 14.9586 | 204.12 | 0.1255 |
| Mo17xM0059 | 0.3415 | 25.0164 | 182.83 | 26.1268 | 474.54 | 13.0205 | 174 | 0.1386 |
| Mo17xM0060 | 0.3574 | 25.4476 | 197.51 | 31.5136 | 462.82 | 13.0901 | 172.11 | 0.1489 |
| Mo17xM0061 | 0.3756 | 25.1141 | 219.38 | 32.3235 | 579 | 12.3185 | 218.02 | 0.1302 |
| Mo17xM0064 | 0.3652 | 24.4338 | 203.87 | 28.5139 | 483.3 | 13.0335 | 180.5 | 0.1322 |
| Mo17xM0065 | 0.3133 | 23.1754 | 173.42 | 20.89 | 449.62 | 14.3665 | 154.95 | 0.1554 |
| Mo17xM0066 | 0.3292 | 25.91 | 200.72 | 27.4343 | 587.06 | 14.5587 | 195.82 | 0.1344 |
| Mo17xM0067 | 0.3635 | 24.2395 | 212.89 | 26.2109 | 477.99 | 12.0348 | 172.84 | 0.08265 |
| Mo17xM0069 | 0.306 | 24.5269 | 212.5 | 29.0517 | 542.61 | 13.7911 | 161.3 | 0.1677 |
| Mo17xM0070 | 0.3206 | 22.7369 | 192.53 | 19.7383 | 474.11 | 12.5235 | 150.56 | 0.1192 |
| Mo17xM0071 | 0.3439 | 23.1505 | 186.22 | 22.6144 | 485.93 | 13.4434 | 169.57 | 0.1347 |
| Mo17xM0075 | 0.3406 | 24.1307 | 213.05 | 29.6919 | 521.6 | 12.5851 | 178.06 | 0.1254 |
| Mo17xM0076 | 0.351 | 24.9538 | 205.13 | 28.4091 | 495.38 | 14.4214 | 178.41 | 0.1421 |
| Mo17xM0077 | 0.3579 | 23.6924 | 217.94 | 25.1234 | 528.46 | 12.3159 | 187.34 | 0.1298 |
| Mo17xM0078 | 0.3675 | 25.7433 | 213.85 | 34.3091 | 581.98 | 13.963 | 214.97 | 0.1388 |
| Mo17xM0079 | 0.3522 | 23.0973 | 186.36 | 22.2283 | 390.63 | 12.2572 | 141.62 | 0.09293 |
| Mo17xM0080 | 0.331 | 24.3271 | 192.57 | 28.1078 | 541.2 | 13.2271 | 180.47 | 0.1294 |
| Mo17xM0081 | 0.3314 | 24.0764 | 196.17 | 27.1971 | 513.21 | 12.5526 | 168.81 | 0.1336 |
| Mo17xM0083 | 0.3345 | 25.3749 | 193.44 | 26.0137 | 526.07 | 12.2935 | 176.49 | 0.1435 |
| Mo17xM0084 | 0.3594 | 23.1825 | 183.2 | 20.5753 | 423.51 | 11.8219 | 151.94 | 0.1081 |
| Mo17xM0085 | 0.3441 | 23.8008 | 208.77 | 28.9787 | 568.85 | 13.5612 | 193.57 | 0.1477 |
| Mo17xM0086 | 0.2762 | 20.4987 | 148.52 | 15.7812 | 352.07 | 12.8711 | 108.72 | 0.1374 |
| Mo17xM0088 | 0.388 | 24.9941 | 188.75 | 28.0482 | 344.74 | 12.2684 | 127.64 | 0.1294 |
| Mo17xM0090 | 0.3385 | 22.912 | 196.9 | 21.6951 | 465.88 | 12.6685 | 164.01 | 0.1416 |
| Mo17xM0091 | 0.3459 | 23.8121 | 193.93 | 22.669 | 486.93 | 12.8497 | 173.13 | 0.1321 |
| Mo17xM0092 | 0.3409 | 23.0974 | 181.05 | 17.1792 | 437.09 | 11.9936 | 147.93 | 0.1383 |
| Mo17xM0093 | 0.3576 | 23.114 | 214.55 | 24.395 | 425.63 | 12.636 | 153.64 | 0.1303 |
| Mo17xM0095 | 0.3207 | 24.8166 | 218.33 | 26.9185 | 623.86 | 13.8804 | 199.83 | NA |
| Mo17xM0096 | 0.2985 | 20.0712 | 149.11 | 15.8652 | 370.02 | 13.8433 | 120.36 | 0.1198 |
| Mo17xM0097 | 0.343 | 24.47 | 211.17 | 27.1119 | 625.65 | 14.0363 | 213.81 | 0.1133 |
| Mo17xM0098 | 0.3265 | 24.0971 | 208.06 | 24.1624 | 562.96 | 13.3876 | 183.53 | 0.1173 |
| Mo17xM0099 | 0.3455 | 24.0314 | 199.25 | 26.4859 | 392.6 | 12.5319 | 135.01 | 0.1457 |

Figure 6O

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| Mo17xM0100 | 0.3196 | 22.6019 | 178.1 | 19.9671 | 394.68 | 11.4085 | 127.81 | 0.1192 |
| Mo17xM0101 | 0.3652 | 24.1397 | 200.39 | 22.9826 | 529.5 | 13.0352 | 194.59 | 0.113 |
| Mo17xM0102 | 0.2968 | 24.6207 | 214.47 | 27.0091 | 653.63 | 14.4635 | 193.32 | 0.143 |
| Mo17xM0103 | 0.3467 | 23.6136 | 209.49 | 25.0628 | 474.86 | 12.8985 | 175.47 | 0.1407 |
| Mo17xM0104 | 0.3806 | 23.9378 | 207.58 | 25.2913 | 531.26 | 12.2903 | 200.94 | 0.1057 |
| Mo17xM0105 | 0.3593 | 24.4321 | 177.9 | 27.129 | 455.52 | 13.1482 | 166.72 | 0.1043 |
| Mo17xM0106 | 0.3569 | 22.5023 | 187.9 | 20.0262 | 439.2 | 11.9459 | 158.47 | 0.1372 |
| Mo17xM0107 | 0.3161 | 25.0951 | 216.94 | 29.7193 | 628.64 | 13.8215 | 198.56 | 0.1332 |
| Mo17xM0109 | 0.3178 | 21.9753 | 197.2 | 20.1503 | 470.73 | 12.3856 | 161.81 | 0.1247 |
| Mo17xM0110 | 0.3516 | 24.5437 | 190.14 | 26.9694 | 397.87 | 12.6189 | 140.79 | 0.1198 |
| Mo17xM0113 | 0.3421 | 25.5772 | 184.72 | 25.3269 | 577.56 | 14.626 | 198.22 | 0.1221 |
| Mo17xM0114 | 0.3398 | 25.2711 | 242.26 | 31.4305 | 709.02 | 14.6744 | 241.23 | 0.1219 |
| Mo17xM0115 | 0.333 | 24.947 | 223.74 | 24.2984 | 526.83 | 12.2273 | 174.91 | 0.1312 |
| Mo17xM0116 | 0.3751 | 22.5513 | 187.22 | 20.1254 | 388.99 | 11.4322 | 153.85 | 0.1285 |
| Mo17xM0117 | 0.3382 | 24.0146 | 215.5 | 27.7405 | 490.3 | 13.2666 | 165.31 | 0.0981 |
| Mo17xM0118 | 0.3296 | 24.3752 | 191.92 | 27.0487 | 505.57 | 13.6816 | 177.41 | 0.09582 |
| Mo17xM0120 | 0.3402 | 23.6661 | 189.06 | 23.0984 | 488.42 | 13.3757 | 167.07 | 0.1272 |
| Mo17xM0121 | 0.3585 | 25.1087 | 217.6 | 29.5899 | 572.52 | 13.4964 | 201.16 | 0.1379 |
| Mo17xM0122 | 0.3605 | 23.9661 | 180.08 | 24.0079 | 437.15 | 13.4262 | 159.53 | 0.1406 |
| Mo17xM0123 | 0.3383 | 22.7834 | 193.67 | 21.0316 | 402.25 | 12.5635 | 142.09 | 0.1059 |
| Mo17xM0124 | 0.3628 | 24.0603 | 187.2 | 23.7019 | 439.79 | 13.2077 | 161.49 | 0.1115 |
| Mo17xM0125 | 0.3349 | 25.8483 | 222.44 | 34.7503 | 645.24 | 14.6928 | 208.64 | 0.1203 |
| Mo17xM0126 | 0.3591 | 23.3696 | 214.38 | 23.8099 | 519.21 | 12.116 | 185.28 | 0.1145 |
| Mo17xM0127 | 0.3391 | 24.1681 | 210.11 | 26.2231 | 499.69 | 13.0002 | 171.32 | 0.1002 |
| Mo17xM0129 | 0.3618 | 25.5502 | 222.71 | 28.0793 | 457.34 | 12.5851 | 164.36 | 0.1296 |
| Mo17xM0130 | 0.3208 | 23.3755 | 206.68 | 23.7616 | 566.85 | 14.1638 | 182.02 | 0.1649 |
| Mo17xM0131 | 0.3446 | 23.3595 | 200.01 | 19.6122 | 464.37 | 12.2311 | 159 | 0.1134 |
| Mo17xM0132 | 0.3372 | 24.2619 | 179.69 | 21.3052 | 440.73 | 12.4775 | 152.16 | 0.1451 |
| Mo17xM0133 | 0.3163 | 24.3286 | 192.71 | 27.5149 | 487.09 | 13.0308 | 159.65 | 0.1404 |
| Mo17xM0138 | 0.3587 | 23.8927 | 194.47 | 24.1852 | 476.71 | 12.6324 | 171.19 | 0.1272 |
| Mo17xM0141 | 0.3655 | 25.1098 | 188.74 | 24.518 | 511.39 | 13.2403 | 185.56 | 0.1028 |
| Mo17xM0142 | 0.3108 | 24.1896 | 206.58 | 23.3243 | 612.53 | 13.9869 | 189.41 | 0.1209 |
| Mo17xM0143 | 0.3495 | 25.2318 | 202.32 | 28.6721 | 499.8 | 13.6148 | 173.25 | 0.1444 |
| Mo17xM0144 | 0.3251 | 24.9116 | 203.99 | 29.2227 | 584.13 | 13.5414 | 189.13 | 0.1455 |
| Mo17xM0145 | 0.3479 | 25.7757 | 187.7 | 25.615 | 478.89 | 13.6354 | 168.65 | 0.1553 |
| Mo17xM0147 | 0.3127 | 23.084 | 192.5 | 21.9672 | 466.78 | 12.9292 | 152.9 | 0.1207 |
| Mo17xM0149 | 0.3153 | 24.9901 | 209.26 | 26.1957 | 552.37 | 14.1954 | 171.29 | 0.1081 |
| Mo17xM0150 | 0.3554 | 22.8447 | 215.13 | 21.7425 | 458.91 | 11.8625 | 162.87 | 0.08831 |
| Mo17xM0151 | 0.3344 | 24.4134 | 191.15 | 21.3736 | 465.72 | 12.2654 | 152.3 | 0.1082 |
| Mo17xM0152 | 0.3877 | 24.8362 | 204.58 | 26.251 | 375.05 | 12.7945 | 146.15 | 0.1109 |
| Mo17xM0154 | 0.3355 | 23.6465 | 207.35 | 24.7405 | 486.1 | 12.7343 | 165.45 | 0.1137 |
| Mo17xM0155 | 0.3597 | 23.463 | 202.04 | 23.5254 | 505.79 | 12.2849 | 182.39 | 0.1239 |
| Mo17xM0156 | 0.3577 | 25.1249 | 192.48 | 25.3355 | 529.1 | 13.7207 | 186.61 | 0.1394 |
| Mo17xM0157 | 0.3484 | 24.3933 | 207.39 | 24.1341 | 556.94 | 13.7473 | 194.18 | 0.1368 |

Figure 6P

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| Mo17xM0160 | 0.3586 | 25.4465 | 216.87 | 27.0609 | 595.33 | 13.72 | 214.11 | 0.1288 |
| Mo17xM0160A | 0.3573 | 25.3038 | 195.66 | 31.4181 | 540.04 | 14.5503 | 210.31 | 0.1185 |
| Mo17xM0161 | 0.3496 | 23.3755 | 215.1 | 27.4266 | 493.91 | 12.8375 | 175.86 | 0.1318 |
| Mo17xM0162 | 0.3557 | 24.6492 | 190.27 | 22.4739 | 446.98 | 13.1806 | 156.38 | 0.1198 |
| Mo17xM0162A | 0.3299 | 25.0361 | 218.27 | 29.4889 | 607.56 | 15.4187 | 200.75 | 0.1329 |
| Mo17xM0163 | 0.3507 | 24.481 | 213.58 | 27.5261 | 545.43 | 13.0577 | 191.61 | 0.1142 |
| Mo17xM0165 | 0.3535 | 25.5016 | 194.75 | 27.7416 | 634.11 | 14.4773 | 221 | 0.112 |
| Mo17xM0166 | 0.3528 | 24.021 | 194.73 | 24.0391 | 478.95 | 12.7931 | 168.71 | 0.1214 |
| Mo17xM0167 | 0.3071 | 23.3873 | 178.18 | 21.5124 | 483.06 | 13.6352 | 148.38 | 0.1048 |
| Mo17xM0168 | 0.358 | 24.6389 | 215.2 | 30.1138 | 519.3 | 12.3972 | 186.36 | 0.1194 |
| Mo17xM0169 | 0.3402 | 24.2545 | 190.99 | 25.939 | 494.19 | 12.5193 | 175.05 | 0.1132 |
| Mo17xM0173 | 0.3413 | 24.4096 | 193.93 | 30.8415 | 559.61 | 14.4075 | 217.82 | 0.1101 |
| Mo17xM0174 | 0.365 | 24.5771 | 216.9 | 28.4842 | 520.09 | 12.0197 | 190.58 | 0.1307 |
| Mo17xM0176 | 0.3953 | 23.8671 | 213.01 | 28.5486 | 560.55 | 13.4395 | 225.1 | 0.144 |
| Mo17xM0177 | 0.3909 | 24.7124 | 209.84 | 27.7181 | 486.58 | 13.0288 | 192.77 | 0.1313 |
| Mo17xM0178 | 0.3183 | 24.445 | 196.48 | 26.1697 | 596.26 | 14.129 | 189.46 | 0.1358 |
| Mo17xM0179 | 0.356 | 24.6701 | 216.84 | 27.3977 | 541.72 | 11.962 | 193.21 | 0.1578 |
| Mo17xM0180 | 0.3563 | 23.6754 | 207.94 | 22.2613 | 542.19 | 12.2639 | 191.96 | 0.1446 |
| Mo17xM0181 | 0.3613 | 25.5033 | 218.87 | 27.6201 | 470.22 | 13.0819 | 172.52 | 0.1235 |
| Mo17xM0185 | 0.2323 | 23.5898 | 155.62 | 19.1004 | 349.45 | 15.1689 | 125.28 | 0.1352 |
| Mo17xM0187 | 0.334 | 24.961 | 179.27 | 22.9248 | 488.9 | 13.457 | 169.48 | 0.1354 |
| Mo17xM0188 | 0.3641 | 25.9041 | 214.4 | 30.9386 | 603.57 | 13.7244 | 219.04 | 0.1264 |
| Mo17xM0189 | 0.3536 | 24.7291 | 216.74 | 29.2261 | 594.39 | 13.6478 | 210.83 | 0.1201 |
| Mo17xM0191 | 0.3324 | 23.9394 | 181.83 | 23.0021 | 456.41 | 13.0866 | 151.74 | 0.1127 |
| Mo17xM0192 | 0.3074 | 25 | 181.41 | 21.043 | 451.21 | 15.1135 | 153.79 | 0.1366 |
| Mo17xM0194 | 0.3617 | 25.107 | 192.26 | 26.1453 | 411.25 | 14.1657 | 148.93 | 0.1205 |
| Mo17xM0195 | 0.3411 | 24.1048 | 190.43 | 25.9727 | 383.81 | 12.0036 | 136.73 | 0.1324 |
| Mo17xM0196 | 0.3089 | 24.6279 | 202.83 | 27.7867 | 540.84 | 13.5482 | 174.85 | 0.1395 |
| Mo17xM0197 | 0.3509 | 25.478 | 203.19 | 29.7462 | 548.29 | 14.1887 | 191.79 | 0.1177 |
| Mo17xM0198 | 0.3675 | 24.1063 | 219.72 | 26.885 | 556.74 | 12.9745 | 205.67 | 0.1457 |
| Mo17xM0199 | 0.3102 | 21.7314 | 203.42 | 21.5263 | 524.95 | 12.0598 | 163.37 | 0.1507 |
| Mo17xM0200 | 0.3524 | 24.942 | 216.89 | 27.0349 | 519.37 | 12.8094 | 183.95 | 0.141 |
| Mo17xM0201 | 0.3401 | 25.488 | 222.42 | 28.5652 | 689.12 | 14.414 | 236.07 | 0.1298 |
| Mo17xM0203 | 0.34 | 25.2699 | 201.09 | 26.6001 | 554.19 | 14.1766 | 192.29 | 0.1275 |
| Mo17xM0204 | 0.3348 | 23.8233 | 193.06 | 25.3176 | 581.37 | 13.0381 | 195.1 | 0.139 |
| Mo17xM0205 | 0.3286 | 25.3252 | 207.41 | 26.8855 | 580.67 | 14.0323 | 195.17 | 0.1224 |
| Mo17xM0206 | 0.3056 | 22.5379 | 185.87 | 21.1658 | 454.3 | 13.0276 | 145.49 | 0.1388 |
| Mo17xM0208 | 0.3396 | 23.8516 | 190.92 | 25.1743 | 473.64 | 13.2513 | 159.9 | 0.1346 |
| Mo17xM0209 | 0.3502 | 25.856 | 211.01 | 29.4304 | 500.47 | 13.973 | 178.58 | 0.1161 |
| Mo17xM0210 | 0.3126 | 23.7585 | 219.45 | 24.5247 | 518.44 | 12.1195 | 161.47 | 0.1406 |
| Mo17xM0212 | 0.3735 | 24.2657 | 208.53 | 24.6627 | 476.96 | 11.6382 | 179.19 | 0.09949 |
| Mo17xM0213 | 0.3534 | 24.4513 | 213.27 | 28.3455 | 533.13 | 12.9171 | 187.58 | 0.1191 |
| Mo17xM0214 | 0.3434 | 22.0892 | 194.1 | 23.8169 | 496.01 | 13.8695 | 171.35 | 0.1098 |
| Mo17xM0215 | 0.3499 | 24.9518 | 187.82 | 26.5696 | 438.77 | 12.7085 | 153.71 | 0.1146 |

Figure 6Q

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| Mo17xM0216 | 0.3698 | 23.8989 | 199.79 | 24.7593 | 485.09 | 12.8699 | 182.52 | 0.1287 |
| Mo17xM0217 | 0.3106 | 26.1435 | 203.79 | 27.6627 | 602.63 | 14.2027 | 185.73 | 0.1307 |
| Mo17xM0218 | 0.3361 | 24.0773 | 194.57 | 22.3426 | 548.71 | 13.4969 | 183.65 | 0.1295 |
| Mo17xM0219 | 0.3407 | 23.9112 | 207.31 | 22.5634 | 522.77 | 12.9064 | 179.04 | 0.1326 |
| Mo17xM0220 | 0.3399 | 25.8341 | 213.95 | 31.838 | 670.77 | 15.1168 | 227.14 | 0.1182 |
| Mo17xM0222 | 0.3519 | 24.4208 | 193.48 | 23.3425 | 534.57 | 13.4081 | 187.68 | 0.136 |
| Mo17xM0223 | 0.3576 | 23.6806 | 171.51 | 25.8985 | 477.27 | 12.9272 | 176.36 | 0.1256 |
| Mo17xM0225 | 0.3391 | 24.8512 | 205.15 | 27.9149 | 510.02 | 13.2007 | 173.82 | 0.1272 |
| Mo17xM0228 | 0.3225 | 24.0363 | 202.51 | 23.8185 | 600.72 | 14.1954 | 191.71 | 0.1232 |
| Mo17xM0229 | 0.3102 | 23.4172 | 173.89 | 21.1197 | 442.42 | 13.0299 | 150.79 | 0.1276 |
| Mo17xM0230 | 0.37 | 25.0676 | 214.55 | 26.7255 | 470.09 | 12.1924 | 174.54 | 0.129 |
| Mo17xM0232 | 0.3497 | 24.6405 | 205.47 | 24.3964 | 522.1 | 13.6058 | 180.47 | 0.1015 |
| Mo17xM0233 | 0.3351 | 25.3123 | 219.52 | 32.3151 | 639.5 | 13.6364 | 213.02 | 0.1373 |
| Mo17xM0234 | 0.3382 | 24.9572 | 190.18 | 22.9249 | 494.79 | 13.7109 | 169.37 | 0.1161 |
| Mo17xM0235 | 0.3523 | 23.8072 | 213.05 | 26.6166 | 545.65 | 13.6485 | 191.23 | 0.1204 |
| Mo17xM0236 | 0.3436 | 25.3021 | 214.13 | 30.9313 | 605.79 | 12.7095 | 204.85 | 0.1423 |
| Mo17xM0238 | 0.3158 | 23.2412 | 219.85 | 31.8936 | 639.52 | 14.7356 | 201.76 | 0.1406 |
| Mo17xM0239 | 0.3178 | 25.4036 | 196.2 | 27.9979 | 578.84 | 14.302 | 202.47 | NA |
| Mo17xM0240 | 0.3329 | 24.8775 | 208.26 | 29.1184 | 644.74 | 13.3038 | 213.18 | 0.1505 |
| Mo17xM0241 | 0.3423 | 20.488 | 181.75 | 24.0237 | 461.87 | 12.9244 | 166.51 | 0.09144 |
| Mo17xM0244 | 0.3514 | 25.0426 | 205.81 | 24.5584 | 537.75 | 12.936 | 188.67 | NA |
| Mo17xM0245 | 0.3739 | 28.4757 | 230.48 | 38.3334 | 624.55 | 14.4262 | 234.83 | 0.1233 |
| Mo17xM0248 | 0.3541 | 23.8465 | 224.32 | 25.4385 | 577.6 | 12.6952 | 203.84 | 0.1095 |
| Mo17xM0249 | 0.2978 | 24.7566 | 158.82 | 21.2663 | 386.48 | 15.3511 | 110.85 | 0.1361 |
| Mo17xM0251 | 0.3367 | 24.304 | 207.77 | 26.4176 | 503.63 | 12.76 | 169.06 | 0.1163 |
| Mo17xM0252 | 0.345 | 26.0211 | 223.02 | 30.0027 | 621.19 | 13.7326 | 214.07 | 0.1348 |
| Mo17xM0254 | 0.3324 | 24.7447 | 210.81 | 28.1119 | 593.63 | 13.2622 | 197.56 | 0.1479 |
| Mo17xM0256 | 0.3322 | 27.8607 | 213.78 | 31.192 | 636.09 | 15.4099 | 210.97 | 0.1343 |
| Mo17xM0257 | 0.3513 | 22.8228 | 187.96 | 22.0933 | 509.89 | 12.6595 | 179.2 | 0.1367 |
| Mo17xM0258 | 0.3624 | 22.5338 | 206.65 | 26.0646 | 563.52 | 13.4076 | 204.1 | 0.1514 |
| Mo17xM0259 | 0.3694 | 24.5732 | 195.5 | 24.1968 | 467.73 | 12.5013 | 175.78 | 0.1341 |
| Mo17xM0260 | 0.3534 | 24.5113 | 193.19 | 23.4607 | 462.43 | 12.3603 | 161.99 | 0.119 |
| Mo17xM0262 | 0.3395 | 23.9304 | 192.66 | 24.4279 | 449.69 | 13.5986 | 156.83 | 0.1441 |
| Mo17xM0263 | 0.3325 | 24.8385 | 198.41 | 27.5668 | 588.03 | 13.6579 | 201.04 | 0.117 |
| Mo17xM0264 | 0.3365 | 25.5482 | 193.37 | 24.9097 | 494.2 | 13.6317 | 164.02 | 0.1442 |
| Mo17xM0265 | 0.3324 | 23.6188 | 172.28 | 23.3886 | 516.57 | 13.8985 | 171.04 | 0.1586 |
| Mo17xM0266 | 0.3444 | 25.5833 | 195.6 | 26.6872 | 578.05 | 14.7822 | 200.56 | 0.1172 |
| Mo17xM0267 | 0.3331 | 24.8103 | 211.21 | 27.7476 | 611.04 | 13.8332 | 204.91 | 0.1133 |
| Mo17xM0269 | 0.3134 | 23.7898 | 192.37 | 24.0074 | 515.54 | 13.4181 | 162.75 | 0.106 |
| Mo17xM0270 | 0.3592 | 25.4573 | 216.23 | 36.3001 | 530.37 | 13.1274 | 195.15 | 0.1324 |
| Mo17xM0271 | 0.3544 | 22.9865 | 207.44 | 24.2569 | 505.34 | 13.3127 | 195.23 | 0.1567 |
| Mo17xM0272 | 0.305 | 25.0142 | 206.89 | 30.0684 | 637.79 | 14.5514 | 196.03 | 0.1506 |
| Mo17xM0273 | 0.3323 | 25.589 | 178.62 | 27.1193 | 525.34 | 14.2219 | 176.49 | 0.1274 |
| Mo17xM0274 | 0.278 | 23.2078 | 196.98 | 21.2569 | 571.2 | 14.0684 | 169.94 | 0.1109 |

Figure 6R

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| Mo17xM0275 | 0.3471 | 28.2458 | 209.6 | 30.8284 | 748.44 | 16.2424 | 259.51 | 0.1184 |
| Mo17xM0276 | 0.3412 | 24.0947 | 208.01 | 24.0693 | 557.62 | 13.6476 | 190.17 | 0.1234 |
| Mo17xM0279 | 0.3653 | 23.8926 | 190.86 | 24.0718 | 456.67 | 13.7303 | 167.66 | 0.115 |
| Mo17xM0280 | 0.3566 | 24.6674 | 210.84 | 24.1763 | 487.22 | 12.8492 | 175.66 | 0.1172 |
| Mo17xM0281 | 0.4255 | 25.6704 | 219.92 | 32.0255 | 450.47 | 12.0555 | 189.44 | 0.1439 |
| Mo17xM0282 | 0.3129 | 23.8223 | 192.61 | 25.9526 | 477.02 | 13.0503 | 157.46 | 0.1363 |
| Mo17xM0283 | 0.3558 | 25.0516 | 209.98 | 29.4892 | 454.43 | 13.7783 | 163.03 | 0.1776 |
| Mo17xM0284 | 0.3151 | 25.2282 | 210.39 | 24.7957 | 538.08 | 13.2369 | 170.62 | 0.1182 |
| Mo17xM0285 | 0.3201 | 23.9798 | 229.11 | 26.2022 | 547.73 | 12.2808 | 173.35 | 0.1318 |
| Mo17xM0286 | 0.3622 | 25.5915 | 205.92 | 32.8042 | 565.03 | 12.8913 | 207.47 | 0.1346 |
| Mo17xM0287 | 0.3393 | 22.7063 | 177.24 | 23.3433 | 483.22 | 14.3107 | 176.29 | 0.1329 |
| Mo17xM0288 | 0.3583 | 25.6958 | 197.39 | 25.5928 | 563.59 | 13.9471 | 202.18 | 0.1568 |
| Mo17xM0289 | 0.3681 | 23.451 | 207.9 | 25.838 | 513.31 | 12.3036 | 189.44 | 0.1439 |
| Mo17xM0290 | 0.3448 | 23.5917 | 178.3 | 19.7915 | 369.61 | 12.104 | 125.37 | 0.1267 |
| Mo17xM0291 | 0.3315 | 24.3385 | 202.69 | 24.9778 | 548.79 | 14.4668 | 184.25 | 0.1246 |
| Mo17xM0292 | 0.3593 | 23.4324 | 200.64 | 22.7367 | 471.81 | 11.8516 | 170.6 | 0.1204 |
| Mo17xM0293 | 0.3536 | 23.4289 | 186.07 | 23.158 | 461.34 | 11.9839 | 169.62 | 0.1497 |
| Mo17xM0294 | 0.3484 | 23.8402 | 197.31 | 27.6488 | 609.94 | 13.2119 | 212.69 | 0.1385 |
| Mo17xM0295 | 0.3386 | 24.3694 | 220.85 | 28.7786 | 639.8 | 13.7065 | 217.49 | 0.1457 |
| Mo17xM0296 | 0.3439 | 24.5072 | 187.26 | 23.6528 | 472.79 | 12.4487 | 161.85 | 0.1086 |
| Mo17xM0297 | 0.3654 | 25.2707 | 197.22 | 27.5482 | 577.83 | 13.8716 | 210.29 | 0.1328 |
| Mo17xM0298 | 0.3108 | 24.6457 | 193.86 | 24.2538 | 598.17 | 14.4051 | 186.61 | 0.1644 |
| Mo17xM0300 | 0.3791 | 25.0186 | 212.4 | 31.6036 | 566.67 | 12.9787 | 213.9 | 0.1358 |
| Mo17xM0303 | 0.3699 | 24.8288 | 215.1 | 29.5958 | 557.74 | 13.5309 | 204.45 | 0.107 |
| Mo17xM0304 | 0.3797 | 23.4934 | 171.54 | 25.2406 | 389.98 | 12.4112 | 152.2 | 0.1368 |
| Mo17xM0305 | 0.3676 | 22.5532 | 206.8 | 24.6156 | 266.47 | 13.162 | 98.6651 | 0.09489 |
| Mo17xM0306 | 0.3641 | 24.7121 | 210.21 | 30.7755 | 585.47 | 13.0342 | 213.87 | 0.1044 |
| Mo17xM0307 | 0.3591 | 25.6283 | 214.15 | 30.4453 | 532.59 | 13.5468 | 190.29 | 0.09582 |
| Mo17xM0308 | 0.3806 | 24.9481 | 210.52 | 26.562 | 570.42 | 13.5002 | 214.18 | 0.1087 |
| Mo17xM0309 | 0.3119 | 21.7152 | 167.35 | 19.7561 | 405.4 | 13.4675 | 142.17 | 0.1733 |
| Mo17xM0310 | 0.3004 | 22.8893 | 176.03 | 20.6774 | 471.97 | 14.0245 | 146.44 | 0.1465 |
| Mo17xM0311 | 0.344 | 23.1614 | 196.15 | 24.3297 | 539.19 | 13.7849 | 187.54 | 0.1376 |
| Mo17xM0312 | 0.385 | 24.9864 | 211.36 | 34.6792 | 533.43 | 13.9398 | 203.5 | 0.1449 |
| Mo17xM0313 | 0.3415 | 23.998 | 193.79 | 24.4978 | 475.17 | 12.071 | 160.47 | 0.1109 |
| Mo17xM0317 | 0.3422 | 24.2597 | 211.04 | 25.245 | 504.81 | 12.1899 | 172.46 | 0.1371 |
| Mo17xM0318 | 0.3196 | 24.1078 | 226.82 | 28.3102 | 613.4 | 13.1807 | 201.56 | 0.1405 |
| Mo17xM0320 | 0.3386 | 25.1017 | 200.66 | 27.499 | 562.81 | 13.3526 | 191.24 | 0.1324 |
| Mo17xM0321 | 0.3365 | 23.7427 | 184.14 | 22.4564 | 466.26 | 14.0385 | 165.76 | 0.1508 |
| Mo17xM0322 | 0.2745 | 21.9468 | 184.22 | 22.4501 | 444.24 | 13.2676 | 145.56 | 0.1432 |
| Mo17xM0323 | 0.2831 | 23.1006 | 193.52 | 20.552 | 497.6 | 12.7137 | 141.34 | 0.158 |
| Mo17xM0324 | 0.3801 | 25.0391 | 204.35 | 26.7586 | 465.95 | 13.1675 | 177 | 0.1286 |
| Mo17xM0325 | 0.3374 | 25.4245 | 216.29 | 29.9611 | 562.15 | 13.3857 | 193.15 | 0.1368 |
| Mo17xM0326 | 0.2843 | 21.2186 | 154.91 | 16.3768 | 345.44 | 12.3541 | 102.9 | 0.1322 |
| Mo17xM0327 | 0.3207 | 23.1472 | 208.03 | 20.6241 | 476.96 | 12.7731 | 154.47 | 0.1439 |

Figure 6S

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| Mo17xM0328 | 0.3446 | 22.805 | 177.03 | 21.9583 | 467.5 | 13.1784 | 158.9 | 0.1477 |
| Mo17xM0331 | 0.3086 | 21.838 | 187.85 | 21.0543 | 453.29 | 13.883 | 158.72 | 0.1351 |
| Mo17xM0334 | 0.3248 | 24.6775 | 203.97 | 26.2267 | 579.11 | 13.8672 | 185.92 | 0.1409 |
| Mo17xM0335 | 0.336 | 22.497 | 206.48 | 23.7756 | 499.74 | 11.2078 | 168.25 | 0.1343 |
| Mo17xM0337 | 0.3441 | 24.338 | 213.01 | 28.541 | 495.51 | 11.9915 | 175.75 | 0.1208 |
| Mo17xM0338 | 0.3305 | 24.384 | 228.83 | 30.5782 | 598.69 | 12.1731 | 197.84 | 0.1625 |
| Mo17xM0339 | 0.3821 | 26.9619 | 201.01 | 29.6669 | 615.26 | 14.642 | 235.9 | 0.1199 |
| Mo17xM0341 | 0.3272 | 24.8741 | 168.88 | 22.3592 | 371.23 | 13.4186 | 122.3 | 0.1402 |
| Mo17xM0342 | 0.3342 | 21.574 | 182.84 | 24.2378 | 454.11 | 14.0703 | 172.25 | 0.1561 |
| Mo17xM0344 | 0.3592 | 24.624 | 218.52 | 28.4784 | 539.16 | 12.9433 | 196.03 | 0.1233 |
| Mo17xM0345 | 0.3868 | 24.3021 | 227.58 | 28.8985 | 537.61 | 12.2641 | 207.71 | 0.1608 |
| Mo17xM0348 | 0.3289 | 24.4905 | 214.56 | 25.4584 | 545.89 | 12.0301 | 180.14 | 0.1321 |
| Mo17xM0350 | 0.3939 | 22.1549 | 206.24 | 24.0468 | 460.33 | 12.4214 | 181.42 | 0.1343 |
| Mo17xM0351 | 0.3274 | 22.1026 | 162.03 | 17.9793 | 404.89 | 11.6408 | 136.17 | 0.1191 |
| Mo17xM0352 | 0.3083 | 24.2631 | 207.97 | 24.9534 | 638.07 | 14.1846 | 198.83 | 0.1608 |
| Mo17xM0353 | 0.3551 | 24.6846 | 216.24 | 27.2927 | 639.62 | 14.4101 | 226.97 | 0.1591 |
| Mo17xM0354 | 0.355 | 21.5026 | 188.99 | 20.8015 | 409.67 | 12.1914 | 144.65 | 0.1235 |
| Mo17xM0355 | 0.3494 | 23.5044 | 196.48 | 24.6689 | 536.63 | 13.2821 | 186.68 | 0.1186 |
| Mo17xM0357 | 0.3264 | 23.2739 | 177.73 | 19.3384 | 384.34 | 12.688 | 127.12 | 0.1317 |
| Mo17xM0358 | 0.329 | 25.4102 | 212.22 | 27.2323 | 575.86 | 14.5994 | 190.2 | 0.1272 |
| Mo17xM0360 | 0.3028 | 22.7308 | 205.46 | 25.6925 | 490.32 | 12.0589 | 148.1 | 0.1382 |
| Mo17xM0362 | 0.3843 | 25.7369 | 226.62 | 36.0326 | 595.87 | 13.7399 | 228.35 | 0.1465 |
| Mo17xM0364 | 0.3343 | 23.7988 | 198.65 | 26.1046 | 556.53 | 13.7362 | 185.17 | 0.1537 |
| Mo17xM0365 | 0.3485 | 25.1816 | 195.2 | 28.1743 | 538.92 | 14.0282 | 191.92 | 0.1362 |
| Mo17xM0366 | 0.3338 | 23.0821 | 180.1 | 18.9818 | 472.59 | 12.7966 | 157.3 | 0.1476 |
| Mo17xM0368 | 0.3831 | 25.9019 | 211.04 | 29.7047 | 547.24 | 13.147 | 208.26 | 0.1322 |
| Mo17xM0369 | 0.3344 | 23.7374 | 220.27 | 26.2248 | 576.93 | 13.2868 | 193.09 | 0.1296 |
| Mo17xM0370 | 0.3574 | 24.6293 | 184.96 | 25.7613 | 508.25 | 13.9135 | 187.37 | 0.1574 |
| Mo17xM0375 | 0.371 | 23.6652 | 203.79 | 25.4794 | 512.89 | 12.6912 | 190.53 | 0.14 |
| Mo17xM0376 | 0.3555 | 24.3997 | 226.46 | 30.1231 | 557.91 | 12.9427 | 203.62 | 0.1301 |
| Mo17xM0377 | 0.3621 | 24.0699 | 194.84 | 24.4799 | 484.74 | 13.5269 | 177.86 | 0.1142 |
| Mo17xM0378 | 0.3365 | 22.8859 | 190.13 | 21.3718 | 466.72 | 12.9485 | 155.69 | 0.1125 |
| Mo17xM0379 | 0.3105 | 24.0738 | 200.18 | 23.2308 | 526.62 | 12.6729 | 163.86 | 0.1359 |
| Mo17xM0380 | 0.3425 | 21.6762 | 168.44 | 21.1976 | 395.65 | 13.064 | 149.88 | 0.1398 |
| Mo17xM0381 | 0.3474 | 24.4715 | 181.76 | 21.4922 | 496.9 | 12.9028 | 170.03 | 0.1301 |
| Mo17xM0382 | 0.3159 | 22.583 | 183.84 | 21.0293 | 445.33 | 14.6411 | 145.98 | 0.1037 |
| Mo17xM0383 | 0.3313 | 24.1445 | 191.45 | 29.2095 | 496.32 | 13.0567 | 164.1 | 0.1387 |
| Mo17xM0384 | 0.3879 | 24.6045 | 212.83 | 27.0167 | 576.25 | 12.7924 | 220.24 | 0.1268 |
| B73xM0040 | NA | NA | NA | 29.4686 | NA | NA | NA | NA |
| M0040 | NA | NA | NA | 15.6327 | NA | NA | NA | NA |
| Mo17xM0040 | NA | NA | NA | 29.0133 | NA | NA | NA | NA |
| B73xM0042 | NA | NA | NA | NA | NA | NA | NA | 0.1277 |
| B73xM0159 | NA | NA | NA | NA | NA | NA | NA | 0.1123 |
| B73xM0221 | NA | NA | NA | NA | NA | NA | NA | 0.1057 |

Figure 6T

| Genotype | lsmean_akw | lsmean_cd | lsmean_cl | lsmean_cw | lsmean_kc | lsmean_krn | lsmean_kw | lsmean_sdw |
|---|---|---|---|---|---|---|---|---|
| B73xM0237 | NA | NA | NA | NA | NA | NA | NA | 0.09759 |
| B73xM0315 | NA | NA | NA | NA | NA | NA | NA | 0.08251 |
| M0042 | NA | NA | NA | NA | NA | NA | NA | 0.05823 |
| M0083 | NA | NA | NA | NA | NA | NA | NA | 0.1044 |
| M0159 | NA | NA | NA | NA | NA | NA | NA | 0.1227 |
| M0221 | NA | NA | NA | NA | NA | NA | NA | 0.09534 |
| M0237 | NA | NA | NA | NA | NA | NA | NA | 0.08319 |
| M0315 | NA | NA | NA | NA | NA | NA | NA | 0.06955 |
| Mo17xM0042 | NA | NA | NA | NA | NA | NA | NA | 0.1388 |
| Mo17xM0159 | NA | NA | NA | NA | NA | NA | NA | 0.1414 |
| Mo17xM0221 | NA | NA | NA | NA | NA | NA | NA | 0.1267 |
| Mo17xM0237 | NA | NA | NA | NA | NA | NA | NA | 0.1261 |
| Mo17xM0315 | NA | NA | NA | NA | NA | NA | NA | 0.1559 |

Figure 6U

```
                             SEQUENCE LISTING

<160> NUMBER OF SEQ ID NOS: 143

<210> SEQ ID NO 1
<211> LENGTH: 121
<212> TYPE: DNA
<213> ORGANISM: artificial
<220> FEATURE:
<223> OTHER INFORMATION: SNP_35511

<400> SEQUENCE: 1
cggctggctc aacgagtgac ttttttttgc gtctgtatac ctatgtatgt atctgtcatg      60
stacaagttg gctatatgct gatttaataa taagagagaa cttactagta gactattgta     120
t                                                                     121

<210> SEQ ID NO 2
<211> LENGTH: 121
<212> TYPE: DNA
<213> ORGANISM: artificial
<220> FEATURE:
<223> OTHER INFORMATION: SNP_98111

<400> SEQUENCE: 2
aggctacaaa cacaagaacc acaacatctg cgtgcgtagg cagagactca aaaggccagc      60
yctgtatgaa aattctaatg atacaatcct tcaaggtgat cgacgaaggt atattccgtt     120
t                                                                     121

<210> SEQ ID NO 3
<211> LENGTH: 121
<212> TYPE: DNA
<213> ORGANISM: artificial
<220> FEATURE:
<223> OTHER INFORMATION: SNP_23951

<400> SEQUENCE: 3
ggatagctgc tgcttcgcag gcagtgcgtc cacatgaagc ctacattcag agccatcaca      60
kgcctatgga agcttctgcc cacaacaatc tcctgttgtg aatctgatag ttttgagcag     120
g                                                                     121

<210> SEQ ID NO 4
<211> LENGTH: 117
<212> TYPE: DNA
<213> ORGANISM: artificial
<220> FEATURE:
<223> OTHER INFORMATION: SNP_79262

<400> SEQUENCE: 4
ggtttgtgtg tttttatgtc aagacctcac gcatatcgcg cggagtagct aagctcgacc      60
rtatattggt tgcgacgtat gatccttgtt ttatttaagt gtgttggcgg ttttatc        117

<210> SEQ ID NO 5
<211> LENGTH: 121
<212> TYPE: DNA
<213> ORGANISM: artificial
<220> FEATURE:
<223> OTHER INFORMATION: SNP_19249

<400> SEQUENCE: 5
```

```
tgccttgata cattgttaca gagaaacaaa atcaaaaact taagaatgtc cgatacatct    60
kctgtgaatg cacaatacag tcacacggcc acttttataa aaggaaaacg gacctatcgc   120
c                                                                   121
```

<210> SEQ ID NO 6
<211> LENGTH: 121
<212> TYPE: DNA
<213> ORGANISM: artificial
<220> FEATURE:
<223> OTHER INFORMATION: SNP_0984

<400> SEQUENCE: 6

```
ttgatgatgg taatatgtat tctcagactc gacacatgtg tgcaactcat ttaacacacc    60
rccacaggaa ggtaagcttc gcaatccgat agagggatgc ttacaaatag gcctaaatca   120
t                                                                   121
```

<210> SEQ ID NO 7
<211> LENGTH: 121
<212> TYPE: DNA
<213> ORGANISM: artificial
<220> FEATURE:
<223> OTHER INFORMATION: SNP_99055

<400> SEQUENCE: 7

```
tttgtgcgtc cttgtttctt ttcttttttc cagtgagaga gagagagagc tggctaaaga    60
ygagggagaa gctggcacgt aatagggtcg atagttaagc atgatcatcc tgtgtatttg   120
c                                                                   121
```

<210> SEQ ID NO 8
<211> LENGTH: 121
<212> TYPE: DNA
<213> ORGANISM: artificial
<220> FEATURE:
<223> OTHER INFORMATION: SNP_77055

<400> SEQUENCE: 8

```
ttgtatcggt ttgttcagag ttttacggtg tgggaacatt agtagaaatg tcatttcact    60
kccttctttt ccccgctgga tcgcatttca caaaatattt ccaccattct tgcagagaag   120
c                                                                   121
```

<210> SEQ ID NO 9
<211> LENGTH: 103
<212> TYPE: DNA
<213> ORGANISM: artificial
<220> FEATURE:
<223> OTHER INFORMATION: SNP_45551

<400> SEQUENCE: 9

```
tttatcttac agaaatacat acctcaatca tcggtctctc cakgcaaaaa gataacgaaa    60
caaacctaga ctaatgagct gaagaccagt ataaaatagg tcg                     103
```

<210> SEQ ID NO 10
<211> LENGTH: 121
<212> TYPE: DNA
<213> ORGANISM: artificial
<220> FEATURE:
<223> OTHER INFORMATION: SNP_30953

<400> SEQUENCE: 10

```
cccatcatca gatatctaga tcgaagcggg ggtccgaagg caattcatga atggagtgac    60
```

```
racgatagga agctagtaca aactttttgat ccatcagcca tgcacggcat ggaacggaac    120
a                                                                    121

<210> SEQ ID NO 11
<211> LENGTH: 121
<212> TYPE: DNA
<213> ORGANISM: artificial
<220> FEATURE:
<223> OTHER INFORMATION: SNP_84678

<400> SEQUENCE: 11
tggtgattct gtctggttga tatttgctac tgatattggt cccatttgag atatgcgttg    60
mtgctagtct cgtctttctc tgcgcttgat ttatcgttat acatcgctcc atcgctcgct   120
g                                                                    121

<210> SEQ ID NO 12
<211> LENGTH: 121
<212> TYPE: DNA
<213> ORGANISM: artificial
<220> FEATURE:
<223> OTHER INFORMATION: SNP_89298_2

<400> SEQUENCE: 12
gggatgtctt actgcagggt acggctgttg aaaggatgcc acaggttatg tacagaagac    60
mgcacaccag gttgacgcca ggaacccatg tgcgcaaaat gtcatgcctt gcaccgcacc   120
a                                                                    121

<210> SEQ ID NO 13
<211> LENGTH: 121
<212> TYPE: DNA
<213> ORGANISM: artificial
<220> FEATURE:
<223> OTHER INFORMATION: SNP_32823

<400> SEQUENCE: 13
accaattaat ttctgcaaag tgagtaattc gtctacagct tcatgtgagg aagagctgtt    60
saacagcgcc ctgaaggacg aatatggcat aaccagagta ttcgcctaca gcttcaagta   120
a                                                                    121

<210> SEQ ID NO 14
<211> LENGTH: 121
<212> TYPE: DNA
<213> ORGANISM: artificial
<220> FEATURE:
<223> OTHER INFORMATION: SNP_4623

<400> SEQUENCE: 14
atttatgttc atttcttctt ttcttaaaga agcatgcact aagaacatga aggatgcatg    60
ycatggaaag ttttttgaaag tcattgaaac gtatgagctc ctcatgcaat gcattattct   120
c                                                                    121

<210> SEQ ID NO 15
<211> LENGTH: 121
<212> TYPE: DNA
<213> ORGANISM: artificial
<220> FEATURE:
<223> OTHER INFORMATION: SNP_90941

<400> SEQUENCE: 15
```

```
gttttcctgt actaagtata ttgtatatta ttccagcagc gatgtgatct tcaaattcat    60
ygtgatgtat tcgacaccac gctaaaggat ggtctgagca aactttcttc agctcctcaa   120
t                                                                   121
```

<210> SEQ ID NO 16
<211> LENGTH: 121
<212> TYPE: DNA
<213> ORGANISM: artificial
<220> FEATURE:
<223> OTHER INFORMATION: SNP_81248

<400> SEQUENCE: 16

```
gaagggatgt gatgtgtatc tcttaggcta gactgcttca gctagttttc tgtgactgct    60
wcatgaatcc atggattact gatttactgg gcttgtgctt tgtgtatgat gctgccatct   120
g                                                                   121
```

<210> SEQ ID NO 17
<211> LENGTH: 121
<212> TYPE: DNA
<213> ORGANISM: artificial
<220> FEATURE:
<223> OTHER INFORMATION: SNP_82913

<400> SEQUENCE: 17

```
gctgtgagca ttcgtttgta ggaaaagtga gaacggatgt gtatcaatcc gtgttgggtg    60
mcgatgactc acggatgaat caaatatttg cgtatattgg ggccaaaaca gttctatctg   120
a                                                                   121
```

<210> SEQ ID NO 18
<211> LENGTH: 121
<212> TYPE: DNA
<213> ORGANISM: artificial
<220> FEATURE:
<223> OTHER INFORMATION: SNP_93907

<400> SEQUENCE: 18

```
tattcatcct gcttcatgtg tagctttcat ggaaattgtg tatgtaaccc aaatcatggg    60
ygcattacag acctaacgga aaaaagtcag tgctgcgcct ttagaatgca gcttgctctc   120
t                                                                   121
```

<210> SEQ ID NO 19
<211> LENGTH: 121
<212> TYPE: DNA
<213> ORGANISM: artificial
<220> FEATURE:
<223> OTHER INFORMATION: SNP_90380

<400> SEQUENCE: 19

```
aacctggtca gtactacttt agcacaaact tttagccgcg tggaacactc tccacagcac    60
yaccaccgcc acatcgcaaa cactaattta cgatccgcga atctacccc aaggtggcac   120 a                                                                   121
```

<210> SEQ ID NO 20
<211> LENGTH: 112
<212> TYPE: DNA
<213> ORGANISM: artificial
<220> FEATURE:
<223> OTHER INFORMATION: SNP_49724

<400> SEQUENCE: 20

```
tgagttattc tcaggctgcg ccacagaacc atcgatggaa gtacccagca tygttacgcg    60
ctcaaaacga agcacccaca cacaaatgct accggtaaac ggccaatgcg ct           112

<210> SEQ ID NO 21
<211> LENGTH: 121
<212> TYPE: DNA
<213> ORGANISM: artificial
<220> FEATURE:
<223> OTHER INFORMATION: SNP_51496

<400> SEQUENCE: 21 gatttttgt tccagaattg ttatctgtaa caagaacatc tacatctgtg atgactgacc    60
rttaataaat gtgtcccggt gtaccatttg ttttttttct ttgagcactg gcagtagcag   120
g                                                                  121

<210> SEQ ID NO 22
<211> LENGTH: 121
<212> TYPE: DNA
<213> ORGANISM: artificial
<220> FEATURE:
<223> OTHER INFORMATION: SNP_11948

<400> SEQUENCE: 22
ctctgtgtat ctaccatctt gggatgtact gaattgagtt tgggacgtgt atctacctac    60
satcttgtat tgtcagctca aggatgtagc aaactagtag caacttcaaa aaatgagatg   120
t                                                                  121

<210> SEQ ID NO 23
<211> LENGTH: 121
<212> TYPE: DNA
<213> ORGANISM: artificial
<220> FEATURE:
<223> OTHER INFORMATION: SNP_18689

<400> SEQUENCE: 23
ccccatagca aagaccgcct ttccagcacg tgatatttca acagcgcaac gatttcttac    60
wgagtaatta agcatattcc agtgaaaatc caaagcgaca tttgtgttaa ccaagcgaat   120
g                                                                  121

<210> SEQ ID NO 24
<211> LENGTH: 121
<212> TYPE: DNA
<213> ORGANISM: artificial
<220> FEATURE:
<223> OTHER INFORMATION: SNP_61221

<400> SEQUENCE: 24
attacatcaa cgagggcatt aacaaatcaa tcgacttaaa tttcgtttcc ccaatgatgc    60
racttccaaa gttcagctgt cacatttcat ttagatggac taagctactg cagataatct   120
a                                                                  121

<210> SEQ ID NO 25
<211> LENGTH: 121
<212> TYPE: DNA
<213> ORGANISM: artificial
<220> FEATURE:
<223> OTHER INFORMATION: SNP_105143

<400> SEQUENCE: 25
```

```
aaactgagtg ctaaattttg tttcttgtta ctaaccgtta agaatcacga gatggttaat    60
ratggttgag cttgtccaga aaacatggat aagtgaggtc tcaaaaaatg tagcatcttt   120
t                                                                  121

<210> SEQ ID NO 26
<211> LENGTH: 121
<212> TYPE: DNA
<213> ORGANISM: artificial
<220> FEATURE:
<223> OTHER INFORMATION: SNP_84372

<400> SEQUENCE: 26
aagttgactt ggctaaggtc tattgattag atggattaag agaagtgttt gggctgccga    60
rgtcgtaata ttatgattca acatataagt actaataatc agtgggcaaa gcttcgttac   120
t                                                                  121

<210> SEQ ID NO 27
<211> LENGTH: 121
<212> TYPE: DNA
<213> ORGANISM: artificial
<220> FEATURE:
<223> OTHER INFORMATION: SNP_27764

<400> SEQUENCE: 27
aaaccacata gtagtagtag aagtacatgg taaaggacga tggaacatat atatgacact    60
sttgatagat ctaacagatg ttcaacttgt tctccatggt aaaaacatgt tgttgagcag   120
a                                                                  121

<210> SEQ ID NO 28
<211> LENGTH: 121
<212> TYPE: DNA
<213> ORGANISM: artificial
<220> FEATURE:
<223> OTHER INFORMATION: SNP_95039

<400> SEQUENCE: 28
aatttcgaag ttctaaacat ctattgccgg gataaaaatt ctccatatga atctcctccc    60
kaattcgagc ttcagaacac ctagataaaa gagggattag acctatgcca gacaaagctc   120
t                                                                  121

<210> SEQ ID NO 29
<211> LENGTH: 121
<212> TYPE: DNA
<213> ORGANISM: artificial
<220> FEATURE:
<223> OTHER INFORMATION: SNP_75795

<400> SEQUENCE: 29
gcttgttgaa gagaacgctg gtaacatgtt tgctatatat ctggggagtc gatttcgtag    60
ygaggaatga ttcacggca ccattcttat cgtcttatcg aaccacgggc tcatgtatat   120
t                                                                  121

<210> SEQ ID NO 30
<211> LENGTH: 121
<212> TYPE: DNA
<213> ORGANISM: artificial
<220> FEATURE:
<223> OTHER INFORMATION: SNP_70805

<400> SEQUENCE: 30
```

```
aataatccaa acagtatacg gcccaaccga gtaacctcat acaagaacct aaagagagag    60
raaaaaaccg cggatccaac aaccaattac accgtcccta ctaaggtaat gttaaaaaga   120
a                                                                  121

<210> SEQ ID NO 31
<211> LENGTH: 121
<212> TYPE: DNA
<213> ORGANISM: artificial
<220> FEATURE:
<223> OTHER INFORMATION: SNP_43846

<400> SEQUENCE: 31
agtactagta taagcacatc ataataatat atagtatata taggaggagt gcatacataa    60
ytatggcata tatatgcagt acgcacacta cagtccagca ggccggcggt acgacggtag   120
g                                                                  121

<210> SEQ ID NO 32
<211> LENGTH: 121
<212> TYPE: DNA
<213> ORGANISM: artificial
<220> FEATURE:
<223> OTHER INFORMATION: SNP_98032

<400> SEQUENCE: 32
ttggcttcgt tcgtgctttt gctatatggt gtagcgtcct tgcctgtaaa gaaatcccat    60
rtcaccagaa gaatttgaga cgtcaacagt catcaagtac tataaaattt agatgccttt   120
t                                                                  121

<210> SEQ ID NO 33
<211> LENGTH: 121
<212> TYPE: DNA
<213> ORGANISM: artificial
<220> FEATURE:
<223> OTHER INFORMATION: SNP_63437

<400> SEQUENCE: 33
acgcttgttg taccatgcag cctcttgttg atgtatgttg gcactcgttt gtttctccaa    60
kgcacgtgtt cggtaacagt atatagatgg ctacctgtgc gtatgttggc gcacttcatg   120
c                                                                  121

<210> SEQ ID NO 34
<211> LENGTH: 121
<212> TYPE: DNA
<213> ORGANISM: artificial
<220> FEATURE:
<223> OTHER INFORMATION: SNP_94161

<400> SEQUENCE: 34
cgcgattcgg tcaccgaaca aacaaacaaa caaacaacaa acccctccgc ggcactcatc    60
wtcagtccaa aacgacactt ccaccccggc aacagtcaag ctcactttcc gcgagcagga   120
g                                                                  121

<210> SEQ ID NO 35
<211> LENGTH: 121
<212> TYPE: DNA
<213> ORGANISM: artificial
<220> FEATURE:
<223> OTHER INFORMATION: SNP_34738
```

```
<400> SEQUENCE: 35
attgtttttt cattgcgaac actctagtag gccatttatc tacggttttt tcactatatt        60
yattaagata ttatgagatt tcacattgcc ttgtaaagac aaatctctag ccatgtttgg       120
t                                                                      121

<210> SEQ ID NO 36
<211> LENGTH: 121
<212> TYPE: DNA
<213> ORGANISM: artificial
<220> FEATURE:
<223> OTHER INFORMATION: SNP_88270

<400> SEQUENCE: 36
attcacgacc catttaatca ggaaccacgc acaatgtgta tatcataaat agaaatcccc        60
rattgcagat aacaattgtg gaatagaaac gtaatacaaa aggtagattt tagaaaggac       120
a                                                                      121

<210> SEQ ID NO 37
<211> LENGTH: 121
<212> TYPE: DNA
<213> ORGANISM: artificial
<220> FEATURE:
<223> OTHER INFORMATION: SNP_2880

<400> SEQUENCE: 37
cgttcaagtg agatattcaa ttgttcagat attcaaattc tttgaaaaac tcagcacaaa        60
yattcaaatg ttcagatatt caaattcttc gaaaatgttc agactttaga caaaaagtaa       120
c                                                                      121

<210> SEQ ID NO 38
<211> LENGTH: 121
<212> TYPE: DNA
<213> ORGANISM: artificial
<220> FEATURE:
<223> OTHER INFORMATION: SNP_36300

<400> SEQUENCE: 38
ccacctccga agatactgta gattcctatg atcatttggc tgcattgttc cggccacctg        60
wcgccgtctc gccggttgga gcagcaggac caaattccct tgcgtggctc ctgctctttg       120
c                                                                      121

<210> SEQ ID NO 39
<211> LENGTH: 121
<212> TYPE: DNA
<213> ORGANISM: artificial
<220> FEATURE:
<223> OTHER INFORMATION: SNP_77712

<400> SEQUENCE: 39
agaaatgttc attgtcatat tgggcatcca tccacaggca cagttcagcg ggattttaag        60
kctgagttca tcgcttttc aacccgtccg aagctaccaa catcagagcg gtaggggagg        120
c                                                                      121

<210> SEQ ID NO 40
<211> LENGTH: 30
<212> TYPE: DNA
<213> ORGANISM: artificial
<220> FEATURE:
<223> OTHER INFORMATION: SNP_35511 forward primer
```

```
<400> SEQUENCE: 40
acgttggatg gtctactagt aagttctctc                                              30

<210> SEQ ID NO 41
<211> LENGTH: 30
<212> TYPE: DNA
<213> ORGANISM: artificial
<220> FEATURE:
<223> OTHER INFORMATION: SNP_98111 forward primer

<400> SEQUENCE: 41
acgttggatg cgtaggcaga gactcaaaag                                              30

<210> SEQ ID NO 42
<211> LENGTH: 30
<212> TYPE: DNA
<213> ORGANISM: artificial
<220> FEATURE:
<223> OTHER INFORMATION: SNP_23951 forward primer

<400> SEQUENCE: 42
acgttggatg caacaggaga ttgttgtggg                                              30

<210> SEQ ID NO 43
<211> LENGTH: 30
<212> TYPE: DNA
<213> ORGANISM: artificial
<220> FEATURE:
<223> OTHER INFORMATION: SNP_79262 forward primer

<400> SEQUENCE: 43
acgttggatg caaggatcat acgtcgcaac                                              30

<210> SEQ ID NO 44
<211> LENGTH: 30
<212> TYPE: DNA
<213> ORGANISM: artificial
<220> FEATURE:
<223> OTHER INFORMATION: SNP_19249 forward primer

<400> SEQUENCE: 44
acgttggatg gccttgatac attgttacag                                              30

<210> SEQ ID NO 45
<211> LENGTH: 30
<212> TYPE: DNA
<213> ORGANISM: artificial
<220> FEATURE:
<223> OTHER INFORMATION: SNP_0984 forward primer

<400> SEQUENCE: 45
acgttggatg actcgacaca tgtgtgcaac                                              30

<210> SEQ ID NO 46
<211> LENGTH: 30
<212> TYPE: DNA
<213> ORGANISM: artificial
<220> FEATURE:
<223> OTHER INFORMATION: SNP_99055 forward primer

<400> SEQUENCE: 46
acgttggatg tatcgaccct attacgtgcc                                              30

<210> SEQ ID NO 47
```

-continued

```
<211> LENGTH: 30
<212> TYPE: DNA
<213> ORGANISM: artificial
<220> FEATURE:
<223> OTHER INFORMATION: SNP_77055 forward primer

<400> SEQUENCE: 47
acgttggatg ttgtgaaatg cgatccagcg                               30

<210> SEQ ID NO 48
<211> LENGTH: 30
<212> TYPE: DNA
<213> ORGANISM: artificial
<220> FEATURE:
<223> OTHER INFORMATION: SNP_45551 forward primer

<400> SEQUENCE: 48
acgttggatg acatacctca atcatcggtc                               30

<210> SEQ ID NO 49
<211> LENGTH: 30
<212> TYPE: DNA
<213> ORGANISM: artificial
<220> FEATURE:
<223> OTHER INFORMATION: SNP_30953 forward primer

<400> SEQUENCE: 49
acgttggatg catggctgat ggatcaaaag                               30

<210> SEQ ID NO 50
<211> LENGTH: 30
<212> TYPE: DNA
<213> ORGANISM: artificial
<220> FEATURE:
<223> OTHER INFORMATION: SNP_84678 forward primer

<400> SEQUENCE: 50
acgttggatg gcgatggagc gatgtataac                               30

<210> SEQ ID NO 51
<211> LENGTH: 30
<212> TYPE: DNA
<213> ORGANISM: artificial
<220> FEATURE:
<223> OTHER INFORMATION: SNP_89298_2 forward primer

<400> SEQUENCE: 51
acgttggatg tgttgaaagg atgccacagg                               30

<210> SEQ ID NO 52
<211> LENGTH: 30
<212> TYPE: DNA
<213> ORGANISM: artificial
<220> FEATURE:
<223> OTHER INFORMATION: SNP_32823 forward primer

<400> SEQUENCE: 52
acgttggatg tctgcaaagt gagtaattcg                               30

<210> SEQ ID NO 53
<211> LENGTH: 30
<212> TYPE: DNA
<213> ORGANISM: artificial
<220> FEATURE:
<223> OTHER INFORMATION: SNP_4623 forward primer

<400> SEQUENCE: 53
```

```
acgttggatg ttgcatgagg agctcatacg                                              30

<210> SEQ ID NO 54
<211> LENGTH: 30
<212> TYPE: DNA
<213> ORGANISM: artificial
<220> FEATURE:
<223> OTHER INFORMATION: SNP_90941 forward primer

<400> SEQUENCE: 54
acgttggatg attattccag cagcgatgtg                                              30

<210> SEQ ID NO 55
<211> LENGTH: 30
<212> TYPE: DNA
<213> ORGANISM: artificial
<220> FEATURE:
<223> OTHER INFORMATION: SNP_81248 forward primer

<400> SEQUENCE: 55
acgttggatg gtgatgtgta tctcttaggc                                              30

<210> SEQ ID NO 56
<211> LENGTH: 30
<212> TYPE: DNA
<213> ORGANISM: artificial
<220> FEATURE:
<223> OTHER INFORMATION: SNP_82913 forward primer

<400> SEQUENCE: 56
acgttggatg gttttggccc caatatacgc                                              30

<210> SEQ ID NO 57
<211> LENGTH: 30
<212> TYPE: DNA
<213> ORGANISM: artificial
<220> FEATURE:
<223> OTHER INFORMATION: SNP_93907 forward primer

<400> SEQUENCE: 57
acgttggatg gcagcactga cttttttccg                                              30

<210> SEQ ID NO 58
<211> LENGTH: 30
<212> TYPE: DNA
<213> ORGANISM: artificial
<220> FEATURE:
<223> OTHER INFORMATION: SNP_90380 forward primer

<400> SEQUENCE: 58
acgttggatg cacaaacttt tagccgcgtg                                              30

<210> SEQ ID NO 59
<211> LENGTH: 30
<212> TYPE: DNA
<213> ORGANISM: artificial
<220> FEATURE:
<223> OTHER INFORMATION: SNP_49724 forward primer

<400> SEQUENCE: 59
acgttggatg tgagttattc tcaggctgcg                                              30

<210> SEQ ID NO 60
<211> LENGTH: 30
<212> TYPE: DNA
```

```
<213> ORGANISM: artificial
<220> FEATURE:
<223> OTHER INFORMATION: SNP_51496 forward primer

<400> SEQUENCE: 60
acgttggatg aacaaatggt acaccgggac                                    30

<210> SEQ ID NO 61
<211> LENGTH: 30
<212> TYPE: DNA
<213> ORGANISM: artificial
<220> FEATURE:
<223> OTHER INFORMATION: SNP_11948 forward primer

<400> SEQUENCE: 61
acgttggatg tgctacatcc ttgagctgac                                    30

<210> SEQ ID NO 62
<211> LENGTH: 30
<212> TYPE: DNA
<213> ORGANISM: artificial
<220> FEATURE:
<223> OTHER INFORMATION: SNP_18689 forward primer

<400> SEQUENCE: 62
acgttggatg atagcaaaga ccgcctttcc                                    30

<210> SEQ ID NO 63
<211> LENGTH: 31
<212> TYPE: DNA
<213> ORGANISM: artificial
<220> FEATURE:
<223> OTHER INFORMATION: SNP_61221 forward primer

<400> SEQUENCE: 63
acgttggatg cgacttaaat ttcgtttccc c                                  31

<210> SEQ ID NO 64
<211> LENGTH: 30
<212> TYPE: DNA
<213> ORGANISM: artificial
<220> FEATURE:
<223> OTHER INFORMATION: SNP_105143 forward primer

<400> SEQUENCE: 64
acgttggatg ccgttaagaa tcacgagatg                                    30

<210> SEQ ID NO 65
<211> LENGTH: 31
<212> TYPE: DNA
<213> ORGANISM: artificial
<220> FEATURE:
<223> OTHER INFORMATION: SNP_84372 forward primer

<400> SEQUENCE: 65
acgttggatg gattaagaga agtgtttggg c                                  31

<210> SEQ ID NO 66
<211> LENGTH: 31
<212> TYPE: DNA
<213> ORGANISM: artificial
<220> FEATURE:
<223> OTHER INFORMATION: SNP_27764 forward primer

<400> SEQUENCE: 66
acgttggatg ggagaacaag ttgaacatct g                                  31
```

<210> SEQ ID NO 67
<211> LENGTH: 30
<212> TYPE: DNA
<213> ORGANISM: artificial
<220> FEATURE:
<223> OTHER INFORMATION: SNP_95039 forward primer

<400> SEQUENCE: 67
acgttggatg gccgggataa aaattctcca                     30

<210> SEQ ID NO 68
<211> LENGTH: 30
<212> TYPE: DNA
<213> ORGANISM: artificial
<220> FEATURE:
<223> OTHER INFORMATION: SNP_75795 forward primer

<400> SEQUENCE: 68
acgttggatg cttgttgaag agaacgctgg                     30

<210> SEQ ID NO 69
<211> LENGTH: 30
<212> TYPE: DNA
<213> ORGANISM: artificial
<220> FEATURE:
<223> OTHER INFORMATION: SNP_70805 forward primer

<400> SEQUENCE: 69
acgttggatg ccaaccgagt aacctcatac                     30

<210> SEQ ID NO 70
<211> LENGTH: 30
<212> TYPE: DNA
<213> ORGANISM: artificial
<220> FEATURE:
<223> OTHER INFORMATION: SNP_43846 forward primer

<400> SEQUENCE: 70
acgttggatg agtatatata ggaggagtgc                     30

<210> SEQ ID NO 71
<211> LENGTH: 30
<212> TYPE: DNA
<213> ORGANISM: artificial
<220> FEATURE:
<223> OTHER INFORMATION: SNP_98032 forward primer

<400> SEQUENCE: 71
acgttggatg tgctatatgg tgtagcgtcc                     30

<210> SEQ ID NO 72
<211> LENGTH: 30
<212> TYPE: DNA
<213> ORGANISM: artificial
<220> FEATURE:
<223> OTHER INFORMATION: SNP_63437 forward primer

<400> SEQUENCE: 72
acgttggatg taccatgcag cctcttgttg                     30

<210> SEQ ID NO 73
<211> LENGTH: 29
<212> TYPE: DNA
<213> ORGANISM: artificial
<220> FEATURE:

```
<223> OTHER INFORMATION: SNP_94161 forward primer

<400> SEQUENCE: 73
acgttggatg aaacaacaaa cccctccgc                                    29

<210> SEQ ID NO 74
<211> LENGTH: 30
<212> TYPE: DNA
<213> ORGANISM: artificial
<220> FEATURE:
<223> OTHER INFORMATION: SNP_34738 forward primer

<400> SEQUENCE: 74
acgttggatg agtaggccat ttatctacgg                                   30

<210> SEQ ID NO 75
<211> LENGTH: 30
<212> TYPE: DNA
<213> ORGANISM: artificial
<220> FEATURE:
<223> OTHER INFORMATION: SNP_88270 forward primer

<400> SEQUENCE: 75
acgttggatg atcaggaacc acgcacaatg                                   30

<210> SEQ ID NO 76
<211> LENGTH: 31
<212> TYPE: DNA
<213> ORGANISM: artificial
<220> FEATURE:
<223> OTHER INFORMATION: SNP_2880 forward primer

<400> SEQUENCE: 76
acgttggatg caaattcttt gaaaaactca g                                 31

<210> SEQ ID NO 77
<211> LENGTH: 30
<212> TYPE: DNA
<213> ORGANISM: artificial
<220> FEATURE:
<223> OTHER INFORMATION: SNP_36300 forward primer

<400> SEQUENCE: 77
acgttggatg catttggctg cattgttccg                                   30

<210> SEQ ID NO 78
<211> LENGTH: 30
<212> TYPE: DNA
<213> ORGANISM: artificial
<220> FEATURE:
<223> OTHER INFORMATION: SNP_77712 forward primer

<400> SEQUENCE: 78
acgttggatg cttcggacgg gttgaaaaag                                   30

<210> SEQ ID NO 79
<211> LENGTH: 31
<212> TYPE: DNA
<213> ORGANISM: artificial
<220> FEATURE:
<223> OTHER INFORMATION: SNP_35511 reverse primer

<400> SEQUENCE: 79
acgttggatg gcgtctgtat acctatgtat g                                 31
```

```
<210> SEQ ID NO 80
<211> LENGTH: 30
<212> TYPE: DNA
<213> ORGANISM: artificial
<220> FEATURE:
<223> OTHER INFORMATION: SNP_98111 reverse primer

<400> SEQUENCE: 80
acgttggatg taccttcgtc gatcaccttg                                 30

<210> SEQ ID NO 81
<211> LENGTH: 30
<212> TYPE: DNA
<213> ORGANISM: artificial
<220> FEATURE:
<223> OTHER INFORMATION: SNP_23951 reverse primer

<400> SEQUENCE: 81
acgttggatg tgaagcctac attcagagcc                                 30

<210> SEQ ID NO 82
<211> LENGTH: 30
<212> TYPE: DNA
<213> ORGANISM: artificial
<220> FEATURE:
<223> OTHER INFORMATION: SNP_79262 reverse primer

<400> SEQUENCE: 82
acgttggatg gtcaagacct cacgcatatc                                 30

<210> SEQ ID NO 83
<211> LENGTH: 30
<212> TYPE: DNA
<213> ORGANISM: artificial
<220> FEATURE:
<223> OTHER INFORMATION: SNP_19249 reverse primer

<400> SEQUENCE: 83
acgttggatg taaaagtggc cgtgtgactg                                 30

<210> SEQ ID NO 84
<211> LENGTH: 30
<212> TYPE: DNA
<213> ORGANISM: artificial
<220> FEATURE:
<223> OTHER INFORMATION: SNP_0984 reverse primer

<400> SEQUENCE: 84
acgttggatg tgtaagcatc cctctatcgg                                 30

<210> SEQ ID NO 85
<211> LENGTH: 30
<212> TYPE: DNA
<213> ORGANISM: artificial
<220> FEATURE:
<223> OTHER INFORMATION: SNP_99055 reverse primer

<400> SEQUENCE: 85
acgttggatg gtgcgtcctt gtttctttc                                  30

<210> SEQ ID NO 86
<211> LENGTH: 30
<212> TYPE: DNA
<213> ORGANISM: artificial
<220> FEATURE:
<223> OTHER INFORMATION: SNP_77055 reverse primer
```

<400> SEQUENCE: 86
acgttggatg tcagagtttt acggtgtggg                30

<210> SEQ ID NO 87
<211> LENGTH: 30
<212> TYPE: DNA
<213> ORGANISM: artificial
<220> FEATURE:
<223> OTHER INFORMATION: SNP_45551 reverse primer

<400> SEQUENCE: 87
acgttggatg actggtcttc agctcattag                30

<210> SEQ ID NO 88
<211> LENGTH: 30
<212> TYPE: DNA
<213> ORGANISM: artificial
<220> FEATURE:
<223> OTHER INFORMATION: SNP_30953 reverse primer

<400> SEQUENCE: 88
acgttggatg gatatctaga tcgaagcggg                30

<210> SEQ ID NO 89
<211> LENGTH: 30
<212> TYPE: DNA
<213> ORGANISM: artificial
<220> FEATURE:
<223> OTHER INFORMATION: SNP_84678 reverse primer

<400> SEQUENCE: 89
acgttggatg ttgctactga tattggtccc                30

<210> SEQ ID NO 90
<211> LENGTH: 30
<212> TYPE: DNA
<213> ORGANISM: artificial
<220> FEATURE:
<223> OTHER INFORMATION: SNP_89298_2 reverse primer

<400> SEQUENCE: 90
acgttggatg tgacattttg cgcacatggg                30

<210> SEQ ID NO 91
<211> LENGTH: 30
<212> TYPE: DNA
<213> ORGANISM: artificial
<220> FEATURE:
<223> OTHER INFORMATION: SNP_32823 reverse primer

<400> SEQUENCE: 91
acgttggatg gcgaatactc tggttatgcc                30

<210> SEQ ID NO 92
<211> LENGTH: 31
<212> TYPE: DNA
<213> ORGANISM: artificial
<220> FEATURE:
<223> OTHER INFORMATION: SNP_4623 reverse primer

<400> SEQUENCE: 92
acgttggatg gcatgcacta agaacatgaa g               31

<210> SEQ ID NO 93
<211> LENGTH: 30

```
<212> TYPE: DNA
<213> ORGANISM: artificial
<220> FEATURE:
<223> OTHER INFORMATION: SNP_90941 reverse primer

<400> SEQUENCE: 93
acgttggatg tcagaccatc ctttagcgtg                              30

<210> SEQ ID NO 94
<211> LENGTH: 30
<212> TYPE: DNA
<213> ORGANISM: artificial
<220> FEATURE:
<223> OTHER INFORMATION: SNP_81248 reverse primer

<400> SEQUENCE: 94
acgttggatg gcacaagccc agtaaatcag                              30

<210> SEQ ID NO 95
<211> LENGTH: 30
<212> TYPE: DNA
<213> ORGANISM: artificial
<220> FEATURE:
<223> OTHER INFORMATION: SNP_82913 reverse primer

<400> SEQUENCE: 95
acgttggatg cggatgtgta tcaatccgtg                              30

<210> SEQ ID NO 96
<211> LENGTH: 30
<212> TYPE: DNA
<213> ORGANISM: artificial
<220> FEATURE:
<223> OTHER INFORMATION: SNP_93907 reverse primer

<400> SEQUENCE: 96
acgttggatg ctgcttcatg tgtagctttc                              30

<210> SEQ ID NO 97
<211> LENGTH: 30
<212> TYPE: DNA
<213> ORGANISM: artificial
<220> FEATURE:
<223> OTHER INFORMATION: SNP_90380 reverse primer

<400> SEQUENCE: 97
acgttggatg tcgcggatcg taaattagtg                              30

<210> SEQ ID NO 98
<211> LENGTH: 30
<212> TYPE: DNA
<213> ORGANISM: artificial
<220> FEATURE:
<223> OTHER INFORMATION: SNP_49724 reverse primer

<400> SEQUENCE: 98
acgttggatg tgtgggtgct tcgttttgag                              30

<210> SEQ ID NO 99
<211> LENGTH: 30
<212> TYPE: DNA
<213> ORGANISM: artificial
<220> FEATURE:
<223> OTHER INFORMATION: SNP_51496 reverse primer

<400> SEQUENCE: 99
```
acgttggatg caagaacatc tacatctgtg					30

<210> SEQ ID NO 100
<211> LENGTH: 30
<212> TYPE: DNA
<213> ORGANISM: artificial
<220> FEATURE:
<223> OTHER INFORMATION: SNP_11948 reverse primer

<400> SEQUENCE: 100
acgttggatg actgaattga gtttgggacg					30

<210> SEQ ID NO 101
<211> LENGTH: 30
<212> TYPE: DNA
<213> ORGANISM: artificial
<220> FEATURE:
<223> OTHER INFORMATION: SNP_18689 reverse primer

<400> SEQUENCE: 101
acgttggatg tcgctttgga ttttcactgg					30

<210> SEQ ID NO 102
<211> LENGTH: 30
<212> TYPE: DNA
<213> ORGANISM: artificial
<220> FEATURE:
<223> OTHER INFORMATION: SNP_61221 reverse primer

<400> SEQUENCE: 102
acgttggatg ctgcagtagc ttagtccatc					30

<210> SEQ ID NO 103
<211> LENGTH: 30
<212> TYPE: DNA
<213> ORGANISM: artificial
<220> FEATURE:
<223> OTHER INFORMATION: SNP_105143 reverse primer

<400> SEQUENCE: 103
acgttggatg gagacctcac ttatccatgt					30

<210> SEQ ID NO 104
<211> LENGTH: 30
<212> TYPE: DNA
<213> ORGANISM: artificial
<220> FEATURE:
<223> OTHER INFORMATION: SNP_84372 reverse primer

<400> SEQUENCE: 104
acgttggatg taacgaagct ttgcccactg					30

<210> SEQ ID NO 105
<211> LENGTH: 30
<212> TYPE: DNA
<213> ORGANISM: artificial
<220> FEATURE:
<223> OTHER INFORMATION: SNP_27764 reverse primer

<400> SEQUENCE: 105
acgttggatg gaagtacatg gtaaaggacg					30

<210> SEQ ID NO 106
<211> LENGTH: 30
<212> TYPE: DNA
<213> ORGANISM: artificial

<220> FEATURE:
<223> OTHER INFORMATION: SNP_95039 reverse primer

<400> SEQUENCE: 106
acgttggatg tggcataggt ctaatccctc                                              30

<210> SEQ ID NO 107
<211> LENGTH: 30
<212> TYPE: DNA
<213> ORGANISM: artificial
<220> FEATURE:
<223> OTHER INFORMATION: SNP_75795 reverse primer

<400> SEQUENCE: 107
acgttggatg acgataagaa tggtgccgtg                                              30

<210> SEQ ID NO 108
<211> LENGTH: 30
<212> TYPE: DNA
<213> ORGANISM: artificial
<220> FEATURE:
<223> OTHER INFORMATION: SNP_70805 reverse primer

<400> SEQUENCE: 108
acgttggatg agtagggacg gtgtaattgg                                              30

<210> SEQ ID NO 109
<211> LENGTH: 30
<212> TYPE: DNA
<213> ORGANISM: artificial
<220> FEATURE:
<223> OTHER INFORMATION: SNP_43846 reverse primer

<400> SEQUENCE: 109
acgttggatg ggactgtagt gtgcgtactg                                              30

<210> SEQ ID NO 110
<211> LENGTH: 30
<212> TYPE: DNA
<213> ORGANISM: artificial
<220> FEATURE:
<223> OTHER INFORMATION: SNP_98032 reverse primer

<400> SEQUENCE: 110
acgttggatg gtacttgatg actgttgacg                                              30

<210> SEQ ID NO 111
<211> LENGTH: 30
<212> TYPE: DNA
<213> ORGANISM: artificial
<220> FEATURE:
<223> OTHER INFORMATION: SNP_63437 reverse primer

<400> SEQUENCE: 111
acgttggatg cgcacaggta gccatctata                                              30

<210> SEQ ID NO 112
<211> LENGTH: 30
<212> TYPE: DNA
<213> ORGANISM: artificial
<220> FEATURE:
<223> OTHER INFORMATION: SNP_94161 reverse primer

<400> SEQUENCE: 112
acgttggatg aagtgagctt gactgttgcc                                              30

<210> SEQ ID NO 113
<211> LENGTH: 30
<212> TYPE: DNA
<213> ORGANISM: artificial
<220> FEATURE:
<223> OTHER INFORMATION: SNP_34738 reverse primer

<400> SEQUENCE: 113
acgttggatg gagatttgtc tttacaaggc                30

<210> SEQ ID NO 114
<211> LENGTH: 30
<212> TYPE: DNA
<213> ORGANISM: artificial
<220> FEATURE:
<223> OTHER INFORMATION: SNP_88270 reverse primer

<400> SEQUENCE: 114
acgttggatg gtattacgtt tctattccac                30

<210> SEQ ID NO 115
<211> LENGTH: 30
<212> TYPE: DNA
<213> ORGANISM: artificial
<220> FEATURE:
<223> OTHER INFORMATION: SNP_2880 reverse primer

<400> SEQUENCE: 115
acgttggatg gttacttttt gtctaaagtc                30

<210> SEQ ID NO 116
<211> LENGTH: 30
<212> TYPE: DNA
<213> ORGANISM: artificial
<220> FEATURE:
<223> OTHER INFORMATION: SNP_36300 reverse primer

<400> SEQUENCE: 116
acgttggatg aagggaattt ggtcctgctg                30

<210> SEQ ID NO 117
<211> LENGTH: 30
<212> TYPE: DNA
<213> ORGANISM: artificial
<220> FEATURE:
<223> OTHER INFORMATION: SNP_77712 reverse primer

<400> SEQUENCE: 117
acgttggatg gtcatattgg gcatccatcc                30

<210> SEQ ID NO 118
<211> LENGTH: 160
<212> TYPE: DNA
<213> ORGANISM: artificial
<220> FEATURE:
<223> OTHER INFORMATION: PZA01216.1

<400> SEQUENCE: 118
ggtatgttca ttttgctata tttatggtga accgttgaat gtgactggga taatgatgty    60
agaaaaggca ttgaaacttg tcatcggtgc ccatccagtt aatttctacg accgtaaaaa   120
aataagccac tgcaactgtt ttacaagaag tattcatgtg                         160

<210> SEQ ID NO 119
<211> LENGTH: 225

-continued

```
<212> TYPE: DNA
<213> ORGANISM: artificial
<220> FEATURE:
<223> OTHER INFORMATION: PZA01497.1

<400> SEQUENCE: 119
atacgtatac cggagatgaa aggagacgga ggcagtgaag aaatatcctt ttttttcttc      60 tcrttttca cgaggatgcs gtgcactgct cccagaatgc tgtgtccaat ttacaaacgc     120
acaggtggca catgaactag cagagtagct ytmtcttgaa aggaaactgt atttggggtc    180
gatgaaccct ctggtgttat tcttcagack ggtaaacgat ktaac                    225

<210> SEQ ID NO 120
<211> LENGTH: 385
<212> TYPE: DNA
<213> ORGANISM: artificial
<220> FEATURE:
<223> OTHER INFORMATION: PZB00183.4

<400> SEQUENCE: 120
gctccagttc atcagscggt gsgactgcgg atgcctaccc aratagctcc tactagagac     60
gtcagcttcg tcggcrgcga aggcgtccga atggcccgac gccgcaggag gcgaccagac    120
cgggaccacg gcgccctctc tgccggtcca gctgctcgaa gcctccgacg cygacggagc    180
aagcagagcw tctcgcctgt ggttccgasg ctgctggaag rgtcgtgct ggcgagcgcc     240 rttgttggtt ctacgcgcag ctggcggggc ttcggctckk gggtggagat ggagatgcgc    300
gtggaacgga acctgcgccc tggtgtcctc ctcctcgctg ttcgctactr ctagatcggc    360
ggagacctct gttccagctc tgttc                                          385

<210> SEQ ID NO 121
<211> LENGTH: 247
<212> TYPE: DNA
<213> ORGANISM: artificial
<220> FEATURE:
<223> OTHER INFORMATION: PZA02450.1

<400> SEQUENCE: 121
gacctactca tcatttcct gaacattttc cagaacggta acttgtacat tatgtctact      60
gctgccattt tttaatgagc ccaggtatct gagaaaagtg aaatgtcaaa tatcaggtca    120
aggcaaggag aaagaaaagg tggagaaact gcatatkttt caaaccataa aggtgagaga    180
gctaacgama ggttcattac tgacctcrac accrttaggc cctattttgt tgcgggatat    240
gaacttc                                                              247

<210> SEQ ID NO 122
<211> LENGTH: 151
<212> TYPE: DNA
<213> ORGANISM: artificial
<220> FEATURE:
<223> OTHER INFORMATION: PZA01993.7

<400> SEQUENCE: 122
ttgcaatctc atatcttgaa tctcacacca agcataataa ttcacattga aagygtctga     60
cctatcctct agcagttgtc gacaaatttts tccagttcat gtacagtaga aaccgatgcg   120
ttgcagtytc agaacatctt cacttcagat a                                   151

<210> SEQ ID NO 123
<211> LENGTH: 349
<212> TYPE: DNA
```

-continued

```
<213> ORGANISM: artificial
<220> FEATURE:
<223> OTHER INFORMATION: PZA03142.5

<400> SEQUENCE: 123
agtgcccgcg cttgatgtcc gggcgcaggt agttggtcca ccgcagccgg cagctcttrc      60
cgcaccggtt cagccctgca tgcatgcccr crrgtcgcty aagaaatgac gagcacgagg     120
craacaacta ggtcacgcat gcagcaccag gmrgccgggc ygggctcgac cgaggaacag    180
agcacacgta cgtacccgcg agcttgggga gcatgcgcca atttccggcr ccgttggcct    240
ggacgtagtc gacgagcagc ttgtcctcct ccagcgccca ctgtcccttc ttgatcccmt    300
tgctgtsgca gcacggastt ctycccatgg cgrtcggtcg ctctccgtc               349

<210> SEQ ID NO 124
<211> LENGTH: 189
<212> TYPE: DNA
<213> ORGANISM: artificial
<220> FEATURE:
<223> OTHER INFORMATION: zb21.1
<220> FEATURE:
<221> NAME/KEY: misc_feature
<222> LOCATION: (169)..(172)
<223> OTHER INFORMATION: n is a, c, g, or t

<400> SEQUENCE: 124
ctacaaagtg accaaccatt tcatggaatt gcttcaaacc cgagagcggc aagataatag     60
acgaacgatc agctccagcc acctgtaagt acaatcacaa ayrgtaagag caatggatca    120
ctygtggagg cttgtgttta caaataatrg ccaacaacak gttacctcnn nnatcctcaa    180
ataatggcc                                                             189

<210> SEQ ID NO 125
<211> LENGTH: 303
<212> TYPE: DNA
<213> ORGANISM: artificial
<220> FEATURE:
<223> OTHER INFORMATION: PZA00210.1

<400> SEQUENCE: 125
tcccttagga agtatctaca tcagcaggag cctcactcag ttcccctcaa cmtagtgctg     60
aaattagctc tagatatygc tcgyggaatg agctacctac actcccaggg tatactccat    120
agrgacctga aatcagagaa crtacttctg ggagaagata tgtcagtcaa agtygcagat    180
ttcgggattt catgcttgga atcacagtgt ggaagtggca aggggtttac aggaacctac    240
aggtggatgg ctccrgagat gatcaaagag gaacatcata ctaggaaagt ggacgtgtac    300
agc                                                                   303

<210> SEQ ID NO 126
<211> LENGTH: 250
<212> TYPE: DNA
<213> ORGANISM: artificial
<220> FEATURE:
<223> OTHER INFORMATION: PZA02427.1

<400> SEQUENCE: 126
cmatggtaca cgtaacccgg accmgtggtg acgtcgaagg ggamgcggst ctcctccggc     60
gacgcggcgt ctgtgagcgg cttgaagcgc acgaggatcc kggttaccgc gctgggccgc    120
accttgaaga cgttcttcca gccgcgctcc tgccgcggca cgacgtgcct ccgcsmgccg    180
gccaggtggc ggtcgacccc gcacgcgcgc gcgtcgttcc ggcgcttcat gcagtccctg    240
```

```
aastcgtcca                                                          250

<210> SEQ ID NO 127
<211> LENGTH: 246
<212> TYPE: DNA
<213> ORGANISM: artificial
<220> FEATURE:
<223> OTHER INFORMATION: PZA02585.2

<400> SEQUENCE: 127
cttcctgatc ttcttggcrg tcgtgcaatt ccccatgctg ttctggctcg gcaacatatg    60
tggctgacct tgatcctat tggtcgggcc acagacctgt ttcttcttct tcttcagaat    120
aggcatgtgc tacttctggc ttgstgatga awcttaggtt tatcgtggag atggtacaga   180
actattagct atagatatct gggcaatcga aaactgtttt tgtttctgtt agctatakag   240
gcgaaa                                                              246

<210> SEQ ID NO 128
<211> LENGTH: 770
<212> TYPE: DNA
<213> ORGANISM: artificial
<220> FEATURE:
<223> OTHER INFORMATION: PHM2100.21
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (95)..(100)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature
<222> LOCATION: (308)..(308)
<223> OTHER INFORMATION: n is a, c, g, or t

<400> SEQUENCE: 128 gaagggggg gcccggagna aattwctyyc cssssgggwa wwwawcwwwa wararadhhh     60
hmmmvrnvsg rrrrrdrrmh mhnvbsndrd dnnbnnnnnn hwwaddnbss ccttttgbb    120 tkgscywwty ymccyhaawc agawwtwmcy skhhbgryyy dwyyhwamaw wttttwaaa    180
```

-continued

```
atkagktacg awarrggyyy waadawkgcd twaccmgtyt waaaaasgtc mgaaycmytc      240
cmggccyttb ggaammmckr ggtaaaaggt tyraaycgrk gcbnadatwa attcahgatc      300
rnawvaanrk rwttactttk tmrrksmrbg ctahtygtym agtcmgrgra tgacagbths      360
hwhccaatyg cawmatctkg ttytrkggdg aygtygykct gawrtrtctg ccckcttctc      420
gacagatagt agaggaagct ggtggggtgg taactcgcat ggayggtgga gagtttacgg      480
tcttcgatcg ctctgttcyt gkttccaacg gacttgktca tggacaggtt tgtttgttgt      540
saacaatttg gcatattgtt tgtggykttc atggacaggt tttgttctta gtgttgtctg      600
tgtggacagc ttttggaycg gatcggccct cctactgaag accttaagaa gaaagggatc      660
gacttctcgt tgtggttcaa gcctgacaat accckacyga cttttgagcg caycaaggca      720
ccaccaccag ccatkgccac cataataaag cagccatcat ttkkdrrrvm                770

<210> SEQ ID NO 129
<211> LENGTH: 242
<212> TYPE: DNA
<213> ORGANISM: artificial
<220> FEATURE:
<223> OTHER INFORMATION: PZA00521.3

<400> SEQUENCE: 129
arttcccatg aaaaaggaga ccrgkatgct tttgtatcaa tgcttgaggc actatgcaat       60
gcagaaaaga caacagaggc tattgatcta ctgcatatga tgcctgaaaa ggggattact      120
acagatgttg gaatgtataa tatgatmttt tctgctcttg ggaagctgaa gcaggtgtct      180
ttcatgagca gcctctatga tacgatgaga gccaatggtg ttgttcctga tgttttcacg      240
ta                                                                    242

<210> SEQ ID NO 130
<211> LENGTH: 637
<212> TYPE: DNA
<213> ORGANISM: artificial
<220> FEATURE:
<223> OTHER INFORMATION: PHM5599.20
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(65)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
```

```
<220> FEATURE:
<221> NAME/KEY: misc_feature
<222> LOCATION: (196)..(196)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t

<400> SEQUENCE: 130
aaaaaaagyg sagdvvkrrk rmbdwgbymn nkmrramrvr raavvnnddn nrrrrddndn      60
ddnnndrvnr hdvrrrarad nccvartymd rrmkarvrrv ggatccvgtg ccgssgvmra    120
ccggttyrav gcyatcsgva ccstbgtccc gsgsatggtc aagctggtgg mggamacmrc    180
cgamcavgty cwhsrnttyg argkkccgga gatgatagag agtaagctag ctagsamrcr    240
mtbrwytyag gamtgswtgt watctwaatc ttaaaaaaat satttgcttt gcyaggggac    300
cggttckcgt ggttcaarga cgargagttc gcgaggcaga cgatcgcggg gctmaacccg    360
ctgtgcatcc agctgctgac ygagttcccc atcaagagca agctggaccc ggaggtgtac    420
gggccagcrg agtccgccat caccaaggag atcctggaga agcagatgaa cggcscgytg    480
accstggagc aggcgctggc ggcgaagcgg ctgttcatcc tggactacca cgacgtgttc    540
ctgccctacg tgcacaaggt gcggagctgc aggackcgac gctctacgcc tsssgcaccr    600
tctcttcstg acgrmcbkya ckdbshhdnb sgkkdwa                             637

<210> SEQ ID NO 131
<211> LENGTH: 307
<212> TYPE: DNA
<213> ORGANISM: artificial
<220> FEATURE:
<223> OTHER INFORMATION: PZA00193.2

<400> SEQUENCE: 131
actttmcrgg ccacaccaat tctgcttggt tcttgaagat acattcttcc tatggtgccm     60
cctatataaa agccatttct ggttatgttt atccttgaca tgtcaacaga tyagtgttgg    120
gttgcagtca tgcggtcctt aagtcymgga gaaggcgaga agtcattgct kctagcattg    180
tgatcgtcgg ccacaagtaa tcwaaaagtg agagctactt gttcctagca aatggagaag    240
ggcgatatat aggttkatga tcaaattcag tgtatgcaag cagcatattt tgtttagagw    300
tagcttt                                                              307

<210> SEQ ID NO 132
<211> LENGTH: 189
<212> TYPE: DNA
<213> ORGANISM: artificial
<220> FEATURE:
<223> OTHER INFORMATION: PZA00445.22

<400> SEQUENCE: 132
acaacctact agcgtcatgt tctttttty ttcttctttc ccttacaatc ccttagttct      60
tgcaagcaga ggtgtacata taastaawtt ctggtgattg actgatcttc tttkttctgg    120
caaacaaytg caggccgcac aagcttcagg ccgtgtgcaa aagtggggcg gcaaaggcac    180
cgatgaagt                                                            189

<210> SEQ ID NO 133
<211> LENGTH: 202
<212> TYPE: DNA
<213> ORGANISM: artificial
<220> FEATURE:
```

<223> OTHER INFORMATION: PZA02151.3

<400> SEQUENCE: 133

| | | |
|---|---|---|
| gtccacagrg gaaggagagg tgggtacaac aagagtcctg tacggagccg ttcaccccc | 60 |
| gccaggaaaa ggtcacmtag cgatcgtgca cggtcagttt cyaggagcca cctttctagg | 120 |
| tcagtatcaa agtctccacc agtgcatcat ccctcsccac ttgattctcc atctctggag | 180 |
| cgtgcaagtg atggaaatct cg | 202 |

<210> SEQ ID NO 134
<211> LENGTH: 671
<212> TYPE: DNA
<213> ORGANISM: artificial
<220> FEATURE:
<223> OTHER INFORMATION: PHM15427.11
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (656)..(657)
<223> OTHER INFORMATION: n is a, c, g, or t
<220> FEATURE:
<221> NAME/KEY: misc_feature
<222> LOCATION: (659)..(659)
<223> OTHER INFORMATION: n is a, c, g, or t

<400> SEQUENCE: 134

| | |
|---|---|
| anannnnnan tanggaraar aatmwkggrr agytttkrad rabsgwwrgt twrgggnah | 60 |
| amaayyaamg gtwggatcaa agamrahwgg gktaccmggr acggggrgkt tyttggsatt | 120 |
| tttgtytgsa ahhamttytg maagcytgcc caggggttam tttytcctgk tatsgvaccg | 180 |
| aaagcscgkc amgacgacgg cagcctggac ctgattctcg tccatggaag cggcaggytg | 240 |
| agactgtttt gsttcyttgt tgcctatcag ytctgctggc atcttctrct cccctacgtg | 300 |
| gaatatgtca aggtatgtat cgtgactttc tttgtatctg tttacagcgc ttgttgcggc | 360 |
| ggttcatgta cctataggc ttagtagata tccttgagct tagtagcatg ctctttccta | 420 |
| gaacayagga ctccatcagt ttgtcwtggc ttcttagatg mccgtgcact gatgtggyat | 480 |
| tttgttgttg cgrcaatgat tgctcgcaga taaaagaagt gaaggttagg ccagttggca | 540 |
| gtacccacag tggttgtggy gtcgacggtg agcttctkga tggagagsgc ggtgctgaat | 600 |
| ggcagtgctc gctgcttcca gmacaaggca ggctgcttgc mrgatccbgk syrvbnnrnk | 660 |
| kkgaaaraaa a | 671 |

<210> SEQ ID NO 135
<211> LENGTH: 242
<212> TYPE: DNA
<213> ORGANISM: artificial

```
<220> FEATURE:
<223> OTHER INFORMATION: PZA00521.3

<400> SEQUENCE: 135
arttcccatg aaaaaggaga ccrgkatgct tttgtatcaa tgcttgaggc actatgcaat    60
gcagaaaaga caacagaggc tattgatcta ctgcatatga tgcctgaaaa ggggattact   120
acagatgttg gaatgtataa tatgatmttt tctgctcttg ggaagctgaa gcaggtgtct   180
ttcatgagca gcctctatga tacgatgaga gccaatggtg ttgttcctga tgttttcacg   240
ta                                                                 242

<210> SEQ ID NO 136
<211> LENGTH: 244
<212> TYPE: DNA
<213> ORGANISM: artificial
<220> FEATURE:
<223> OTHER INFORMATION: PZA02207.1

<400> SEQUENCE: 136
tbssssytca ctaagtgtga ttgtaacagt ggtacctctt gtgttctgtg ttccgcgatg    60
ttgcagttgg ttgcttgatc gaaagatgtt tcarcctccc atctgctagc tatgatacag   120
atggtycctg ataataatga tgacatattc tgtgatggat gccacrrcat tttttkkttt   180 tgttttttgca ttcagatatt tcrgcttcct krtagtttta catgtcccaa ctaggaatga   240
gaag                                                               244

<210> SEQ ID NO 137
<211> LENGTH: 581
<212> TYPE: DNA
<213> ORGANISM: artificial
<220> FEATURE:
<223> OTHER INFORMATION: PHM565.31
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (514)..(514)
<223> OTHER INFORMATION: n is a, c, g, or t
<220> FEATURE:
<221> NAME/KEY: misc_feature
<222> LOCATION: (519)..(521)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (535)..(536)
<223> OTHER INFORMATION: n is a, c, g, or t
<220> FEATURE:
<221> NAME/KEY: misc_feature
<222> LOCATION: (538)..(539)
<223> OTHER INFORMATION: n is a, c, g, or t
<220> FEATURE:
<221> NAME/KEY: misc_feature
<222> LOCATION: (541)..(543)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t
<220> FEATURE:
```

<221> NAME/KEY: misc_feature
<222> LOCATION: (547)..(548)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (552)..(556)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (562)..(562)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t
<220> FEATURE:
<221> NAME/KEY: misc_feature
<222> LOCATION: (575)..(576)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t

<400> SEQUENCE: 137
ttkvnnbnwh mavrctgaag attgctgaag gagtgggagt ctagcaaayy wttccgtgtc 60
ccaaacgtcc tgctcacagg gtaccgccag aaggccttgc tggacarggc cgagatgctg 120
ctcgacggct tcttgaagaa gggaaagacg cctccttcga ccagctgggg gatygtggca 180
atcggctatg cggagaaagg tgatgtggcg aaagcttatg agatgaccaa gaacgccctc 240
tctgtgcacg cccccaatac tggctggatc cctaggcctt ccatgcttga gatgatactt 300
aagtacytcg gagacgaggg ggaggtcaak gatgkhkaag cttkcgttag tcwgctgaaa 360
gctgctgtgc castggactc tgatatgacc gaggctttgt ckagggctck tkcsagggaa 420
daaakgawkg ctraaraggc arcggaakct cctcgcgggg atbwtattgc ctrarctbgy 480
wktcsgtktt tcascgctkc kycyvaawkg tcwnytbwnn nhyhcradhb dnbbnnhnnb 540
nnnynhnnhn vnnnnnynbh hnkbryyync tnttnncgcn a 581

<210> SEQ ID NO 138
<211> LENGTH: 215
<212> TYPE: DNA
<213> ORGANISM: artificial
<220> FEATURE:
<223> OTHER INFORMATION: PZA03578.1
<220> FEATURE:
<221> NAME/KEY: misc_feature
<222> LOCATION: (56)..(56)
<223> OTHER INFORMATION: n is a, c, g, or t

<400> SEQUENCE: 138
atgcagcaga gaatactgtg gaagktgayg ataagaaaga ggaagccccw gctgtngatg 60
cagcagagaa gaaygaggaa ggtgatgata agaaagagga ggagccccct gcagagaara 120
ctgttgagaa agaggtggtc cctgctgtag atgcagcaga gaatactgaa caaagcaccg 180
gtgggcaagc acagcctaay gatgttgstg cccca 215

<210> SEQ ID NO 139
<211> LENGTH: 999
<212> TYPE: DNA
<213> ORGANISM: artificial
<220> FEATURE:
<223> OTHER INFORMATION: PZA00300.14
<220> FEATURE:
<221> NAME/KEY: misc_feature
<222> LOCATION: (225)..(529)
<223> OTHER INFORMATION: n is a, c, g, or t

<400> SEQUENCE: 139

```
aaaaaatcct cttgtctatc cgacrccmaa acataggtct aaggtcyrst ttygrtygyg    60
ktcgttctma crtgrgctac rrtrccrytg tgtatkgaca tatgtctcaa rcytagtttt   120
ggtyrtggtc katctctcat gkgttacrst tttacgctay gtatgggtga cagtskaasm   180
stctaasggt tttrttgwga agwttttttc ttaatacaat acwynnnnnn nnnnnnnnnn   240
nnnnnnnnnn nnnnnnnnnn nnnnnnnnnn nnnnnnnnnn nnnnnnnnnn nnnnnnnnnn   300
nnnnnnnnnn nnnnnnnnnn nnnnnnnnnn nnnnnnnnnn nnnnnnnnnn nnnnnnnnnn   360
nnnnnnnnnn nnnnnnnnnn nnnnnnnnnn nnnnnnnnnn nnnnnnnnnn nnnnnnnnnn   420
nnnnnnnnnn nnnnnnnnnn nnnnnnnnnn nnnnnnnnnn nnnnnnnnnn nnnnnnnnnn   480
nnnnnnnnnn nnnnnnnnnn nnnnnnnnnn nnnnnnnnnn nnnnnnnnna ggrgttrtct   540
tagccywcag gtcattttkt tacmgtctga atttcttaya ctttytaggt cagtagtaac   600
ttgtagattt ygacttgatt ttcacaggcc tgattaatgc attgaarytt atccarcmka   660
tcaargacaa atacmcaggt aycacttatg cagatttgtt ccagttagca agtgctacgg   720
cgattgaggt cactgtcctt tctctgatta agtatctgac ttggtcactt katcactcaa   780
gtctatgyag tcatatgttt tgtcaatcac atgatacagg aagctggtgg tccaaaamtt   840
ccaatgaaat atgacgkgt tgatgtcaca gcakctgarc agtgtccrcc cgaggggagg   900
cttccyggtc agtgtttcya atgggttctt cattccatat caatgtttca ttrttgtttt   960
gttcaatgct tggaatgtga yttatgagag gtgcctatc                         999
```

<210> SEQ ID NO 140
<211> LENGTH: 400
<212> TYPE: DNA
<213> ORGANISM: artificial
<220> FEATURE:
<223> OTHER INFORMATION: PZA00067.10

<400> SEQUENCE: 140

```
gggaactgta gttgcaattg gtaattccag catgcattcc acaatrtcac aaaacagcta    60
aacrtaaatg tctgtmtata agtgagatac caacattttt gcctattaat ttgcagctag   120
caaatgcctc cccggagctc atcaacaggc tgatcccaga ccatgctagg cggcatcttg   180
ggctcacttt attgcccacc rctggaccat aggcgaaggc tctatggtgt ttaaaccttg   240
ctctttctga ttcttcgttg tgccataggc aattcaaggt gtagaatctg accattattg   300
gaaagccaaa cacgagctgg cgccaatgtg ttgcataagg agaggcggta tgttsgtgya   360
gccagccttt tgycgcctgt tttaatgcaa aatctgattt                         400
```

<210> SEQ ID NO 141
<211> LENGTH: 158
<212> TYPE: DNA
<213> ORGANISM: artificial
<220> FEATURE:

```
<223> OTHER INFORMATION: PZA01563.1

<400> SEQUENCE: 141
aaagacagct aatgtcctga cgcgaagtga tctgcgagct cgcagaagag gtcgcaggca        60
tcatcggcat gctgatgact agtttcctat tgtgaatgtt gkgtagaagt gctgtggaat       120
acccwagaca ttaccatttt atttgggcct catgcccc                               158

<210> SEQ ID NO 142
<211> LENGTH: 196
<212> TYPE: DNA
<213> ORGANISM: artificial
<220> FEATURE:
<223> OTHER INFORMATION: PZA00647.9

<400> SEQUENCE: 142
cgttygaggy ggatcgtatc tgyckgyacg cagtgtttgg smaaatactt gggagtcgca        60
agaaattgtg taaattatag argaggatgg cgacgaagca cgcatgtgtt acgtagttgg       120
ggtttgtgtg cacatggtgg tgggcagggk ctagagggtt tathtttrgg ttattttcsy      180
agtggaatgw atctta                                                       196

<210> SEQ ID NO 143
<211> LENGTH: 134
<212> TYPE: DNA
<213> ORGANISM: artificial
<220> FEATURE:
<223> OTHER INFORMATION: PZA01005.1

<400> SEQUENCE: 143
ttgtggtctt gggagtygga gtttgatttc aaggcgragc aaaatcttrc agagatggct        60
gaggaactgc ctcatctgta gcctgtttct taaaataatg tycagtttct ttacttgcct      120
gtagcctcta taag                                                         134
```

QTL REGULATING EAR PRODUCTIVITY TRAITS IN MAIZE

This application claims the benefit of U.S. Provisional Patent Application Ser. No. 61/364,104, filed Jul. 14, 2010, which is hereby incorporated by reference in its entirety.

FIELD OF THE INVENTION

This invention relates to quantitative trait loci regulating ear productivity traits in maize.

BACKGROUND OF THE INVENTION

Most plant traits of agronomic importance are polygenic, otherwise known as quantitative, traits. A quantitative trait is controlled by several genes located at various locations, or loci, in the plant's genome. The multiple genes have a cumulative effect which contributes to the continuous range of phenotypes observed in many plant traits. These genes are referred to as quantitative trait loci ("QTL").

Multiple experimental paradigms have been developed to identify and analyze QTL. In general, these paradigms involve crossing one or more parental pairs, which can be, for example, a single pair derived from two inbred strains, or multiple related or unrelated parents of different inbred strains or lines, which each exhibit different characteristics relative to the phenotypic trait of interest. The parents and a population of progeny are genotyped, typically for multiple marker loci, and evaluated for the trait of interest. QTL associated with traits of interest are identified based on the significant statistical correlations between the marker genotype(s) and the traits of interest phenotype of the evaluated progeny plants. Numerous methods for determining whether markers are genetically linked to a QTL (or to another marker) are known to those of skill in the art and include, e.g., interval mapping (Lander and Botstein, "Mapping Mendelian Factors Underlying Quantitative Traits Using RFLP Linkage Maps," Genetics 121:185-99 (1989)), regression mapping (Haley and Knott "A Simple Regression Method for Mapping Quantitative Trait Loci In Line Crosses Using Flanking Markers," Heredity 69:315-324 (1992)) or MQM mapping (Jansen, "Controlling the Type I and Type II Errors in Mapping Quantitative Trait Loci" Genetics 138: 871-881 (1994)).

Measurable traits related to ear productivity in maize include kernel row number ("KRN"), kernel count ("KC"), kernel weight ("KW"), average kernel weight ("AKW"), cob weight ("CW"), cob length ("CL"), cob diameter ("CD"), and seedling dry weight ("SDW"). These traits are considered quantitative traits and can be studied via QTL mapping. With this approach, genomic regions regulating a measurable trait are identified in populations segregating for the trait. See, e.g., Veldboom et al., "Molecular Marker-facilitated Studies In an Elite Maize Population: 1. Linkage Analysis and Determination of QTL for Morphological Traits," Theor. Appl. Genet. 88(1):7-16 (1994); Beavis et al., "Identification of Quantitative Trait Loci Using a Small Sample of Toperossed and F4 Progeny from Maize," Crop Sci. 34:882-896 (1994); Austin et al., "Comparative Mapping in F-2:3 and F-6:7 Generations of Quantitative Trait Loci for Grain Yield and Yield Components In Maize," Theor. Appl. Genet. 92(7):817-826 (1996); Veldboom et al., "Genetic Mapping of Quantitative Trait Loci in Maize in Stress and Nonstress Environments. 1. Grain Yield and Yield Components," Crop Sci. 36(5):1310-1319 (1996); Veldboom et al., "Genetic Mapping of Quantitative Trait Loci in Maize in Stress and Nonstress Environments. 2. Plant Height and Flowering," Crop Sci. 36(5):1320-1327 (1996); Bommert et al., "Thick Tassel Dwarf1 Encodes a Putative Maize Ortholog of the Arabidopsis CLAVATA1 Leucine-rich Repeat Receptor-like Kinase," Development 132(6):1235-45 (2005); Tang et al., "Dissection of the Genetic Basis of Heterosis in an Elite Maize Hybrid by QTL Mapping In an Immortalized F2 Population," Theor. Appl. Genet. 120(2): 333-40 (2009).

A primary motivation for development of molecular markers in crop species is the potential for increased efficiency in plant breeding through marker assisted selection ("MAS"). Genetic marker alleles, or alternatively, identified QTL alleles, are used to identify plants that contain a desired genotype at one or more loci, and that are expected to transfer the desired genotype, along with a desired phenotype, to their progeny. Genetic marker alleles (or QTL alleles) can be used to identify plants that contain a desired genotype at one locus, or at several unlinked or linked loci (e.g., a haplotype), and that would be expected to transfer the desired genotype, along with a desired phenotype to their progeny.

Breeding, e.g., for increased ear productivity in maize via the traditional approach is difficult due to the multigenic nature of these traits. What is needed in the art is a means to identify genes conferring increased ear productivity using molecular markers. These markers can then be (i) used to tag the favorable alleles of these genes in segregating maize populations and (ii) employed to make selection for increased ear productivity more effective.

The present invention is directed to achieving these and other objectives and to overcoming limitations in the art.

SUMMARY OF THE INVENTION

One aspect of the present invention is directed to a method for determining an ear productivity trait in maize. This method involves analyzing genomic DNA from a maize plant, germplasm, pollen, or seed for the presence of a molecular marker linked to a QTL associated with an ear productivity trait in maize, where the molecular marker is selected from L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP_35511, SNP_98111, SNP_23951, SNP_79262, SNP_19249, SNP_9084, SNP_99055, SNP_77055, SNP_45551, SNP_30953, SNP_84678, SNP_89298_2, SNP_32823, SNP_4623, SNP_90941, SNP_81248, SNP_82913, SNP_93907, SNP_90380, SNP_49724, SNP_51496, SNP_11948, SNP_18689, SNP_61221, SNP_105143, SNP_84372, SNP_27764, SNP_95039, SNP_75795, SNP_70805, SNP_43846, SNP_98032, SNP_63437, SNP_94161, SNP_34738, SNP_88270, SNP_2880, SNP_36300, and SNP_77712.

Another aspect of the present invention is directed to a method of selecting a maize plant with a desired ear productivity trait. This method involves detecting in a maize plant, germplasm, seed, or pollen at least one allele of a marker locus that is associated with a desired ear productivity trait, where the one or more marker locus localizes within a chromosome interval defined by and including L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP_

35511, SNP__98111, SNP__23951, SNP__79262, SNP__19249, SNP__9084, SNP__99055, SNP__77055, SNP__45551, SNP__30953, SNP__84678, SNP__89298__2, SNP__32823, SNP__4623, SNP__90941, SNP__81248, SNP__82913, SNP__93907, SNP__90380, SNP__49724, SNP__51496, SNP__11948, SNP__18689, SNP__61221, SNP__105143, SNP__84372, SNP__27764, SNP__95039, SNP__75795, SNP__70805, SNP__43846, SNP__98032, SNP__63437, SNP__94161, SNP__34738, SNP__88270, SNP__2880, SNP__36300, and SNP__77712. A maize plant with a desired ear productivity trait is selected by selecting the maize plant comprising the at least one allele of the marker locus.

A further aspect of the present invention is directed to a maize plant selected by methods of the present invention.

Another aspect of the present invention is directed to a method for reliably and predictably introgressing an improved ear productivity trait into a maize line. This method involves selecting plants for breeding based upon the presence of a molecular marker selected from L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP__35511, SNP__98111, SNP__23951, SNP__79262, SNP__19249, SNP__9084, SNP__99055, SNP__77055, SNP__45551, SNP__30953, SNP__84678, SNP__89298__2, SNP__32823, SNP__4623, SNP__90941, SNP__81248, SNP__82913, SNP__93907, SNP__90380, SNP__49724, SNP__51496, SNP__11948, SNP__18689, SNP__61221, SNP__105143, SNP__84372, SNP__27764, SNP__95039, SNP__75795, SNP__70805, SNP__43846, SNP__98032, SNP__63437, SNP__94161, SNP__34738, SNP__88270, SNP__2880, SNP__36300, and SNP__77712.

Another aspect of the present invention is directed to a method for producing a maize line having a desired ear productivity trait. This method involves providing a first maize line having a molecule marker selected from the group consisting of L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP__35511, SNP__98111, SNP__23951, SNP__79262, SNP__19249, SNP__9084, SNP__99055, SNP__77055, SNP__45551, SNP__30953, SNP__84678, SNP__89298__2, SNP__32823, SNP__4623, SNP__90941, SNP__81248, SNP__82913, SNP__93907, SNP__90380, SNP__49724, SNP__51496, SNP__11948, SNP__18689, SNP__61221, SNP__105143, SNP__84372, SNP__27764, SNP__95039, SNP__75795, SNP__70805, SNP__43846, SNP__98032, SNP__63437, SNP__94161, SNP__34738, SNP__88270, SNP__2880, SNP__36300, and SNP__77712, the molecular marker mapping to a genomic locus associated with a desired ear productivity trait. The desired ear productivity trait is introgressed into a maize line by selecting progeny plants for further breeding based upon the presence of the molecular marker to provide a recombinant maize line having the desired ear productivity trait.

A further aspect of the present invention is directed to a kit for selecting a maize plant by marker assisted selection of a QTL associated with a desired ear productivity trait. The kit includes primers for detecting at least one ear productivity trait marker locus selected from the group consisting of L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP__35511, SNP__98111, SNP__23951, SNP__79262, SNP__19249, SNP__9084, SNP__99055, SNP__77055, SNP__45551, SNP__30953, SNP__84678, SNP__89298__2, SNP__32823, SNP__4623, SNP__90941, SNP__81248, SNP__82913, SNP__93907, SNP__90380, SNP__49724, SNP__51496, SNP__11948, SNP__18689, SNP__61221, SNP__105143, SNP__84372, SNP__27764, SNP__95039, SNP__75795, SNP__70805, SNP__43846, SNP__98032, SNP__63437, SNP__94161, SNP__34738, SNP__88270, SNP__2880, SNP__36300, and SNP__77712. The kit also includes instructions for using the primers for detecting the ear productivity trait marker locus and correlating the locus with an improved ear productivity trait.

Another aspect of the present invention is directed to an isolated nucleic acid comprising a QTL associated with an ear productivity trait in maize. The QTL is proximal to a locus corresponding to a marker selected from the group consisting of L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP__35511, SNP__98111, SNP__23951, SNP__79262, SNP__19249, SNP__9084, SNP__99055, SNP__77055, SNP__45551, SNP__30953, SNP__84678, SNP__89298__2, SNP__32823, SNP__4623, SNP__90941, SNP__81248, SNP__82913, SNP__93907, SNP__90380, SNP__49724, SNP__51496, SNP__11948, SNP__18689, SNP__61221, SNP__105143, SNP__84372, SNP__27764, SNP__95039, SNP__75795, SNP__70805, SNP__43846, SNP__98032, SNP__63437, SNP__94161, SNP__34738, SNP__88270, SNP__2880, SNP__36300, and SNP__77712.

A further aspect of the present invention is directed to a transgenic plant comprising a recombinant nucleic acid genetically linked to a locus in maize, where the locus is proximal to a QTL associated with an ear productivity trait in a maize plant, and where the locus corresponds to a marker selected from the group consisting of L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP__35511, SNP__98111, SNP__23951, SNP__79262, SNP__19249, SNP__9084, SNP__99055, SNP__77055, SNP__45551, SNP__30953, SNP__84678, SNP__89298__2, SNP__32823, SNP__4623, SNP__90941, SNP__81248, SNP__82913, SNP__93907, SNP__90380, SNP__49724, SNP__51496, SNP__11948, SNP__18689, SNP__61221, SNP__105143, SNP__84372, SNP__27764, SNP__95039, SNP__75795, SNP__70805, SNP__43846, SNP__98032, SNP__63437, SNP__94161, SNP__34738, SNP__88270, SNP__2880, SNP__36300, and SNP__77712.

The present invention provides molecular markers genetically linked to QTL associated with ear productivity traits. The molecular markers are useful for identifying and producing maize plants with improved ear productivity traits.

Figure 1:
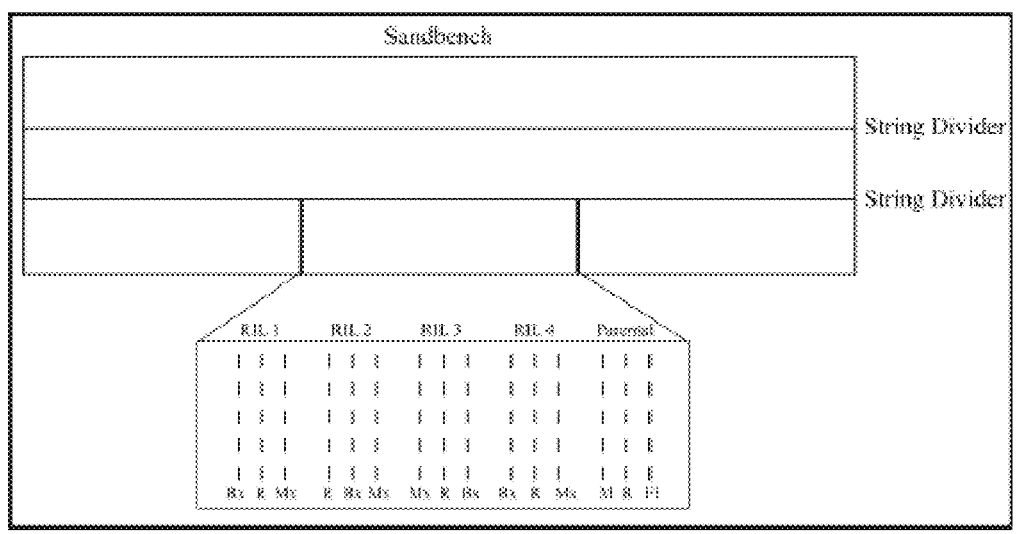
FIG. 1 is a schematic illustration of a replicated greenhouse experiment according to a randomized design with constraints to position each recombinant inbred line ("RIL") and its corresponding hybrids (B73×RIL, Mo17×RIL) at neighboring positions within sand benches. Parental genotypes (B73, Mo17, $F_1$ hybrids) were distributed throughout each replication.
Figure 2:
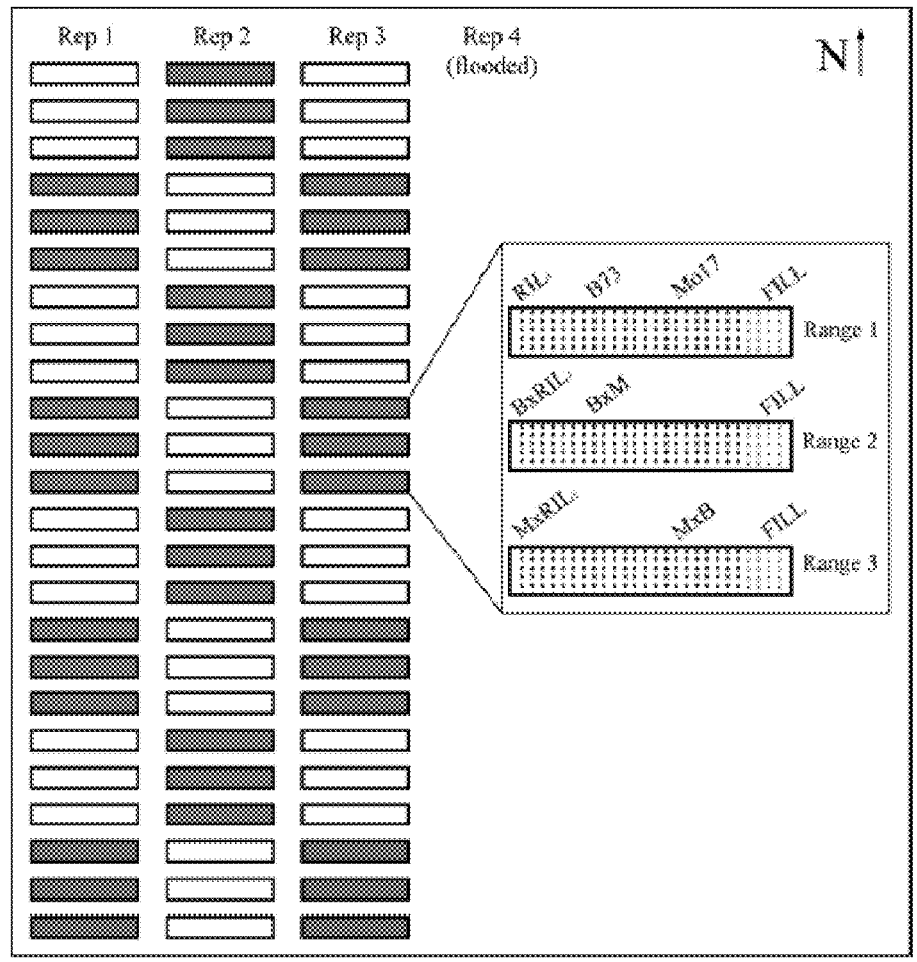
FIG. 2 is a schematic illustration showing a replicated field experiment design that was randomized with constraints to position each RIL and its corresponding hybrids (B73×RIL, Mo17×RIL) at equivalent positions within neighboring ranges. Parental genotypes (B73, Mo17, $F_1$ hybrids) were distributed throughout each replication.

Inbred and hybrid lines were contained in separate ranges to prevent shading and in-ground competition among inbred and hybrid lines.

FIGS. 3A-B are tables identifying the context sequences of molecular markers of the present invention.

FIGS. 4A-B are tables setting forth primer sequences for detecting the presence of molecular markers of the present invention.

FIGS. 5A-D are tables identifying the context sequences of molecular markers of the present invention.

FIGS. 6A-U are tables showing LS Means computed in SAS for each genotype and trait.

DETAILED DESCRIPTION OF THE INVENTION

One aspect of the present invention is directed to a method for determining an ear productivity trait in maize. This method involves analyzing genomic DNA from a maize plant, germplasm, pollen, or seed for the presence of a molecular marker linked to a QTL associated with an ear productivity trait in maize, where the molecular marker is selected from L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP__35511, SNP__98111, SNP__23951, SNP__79262, SNP__19249, SNP__9084, SNP__99055, SNP__77055, SNP__45551, SNP__30953, SNP__84678, SNP__89298__2, SNP__32823, SNP__4623, SNP__90941, SNP__81248, SNP__82913, SNP__93907, SNP__90380, SNP__49724, SNP__51496, SNP__11948, SNP__18689, SNP__61221, SNP__105143, SNP__84372, SNP__27764, SNP__95039, SNP__75795, SNP__70805, SNP__43846, SNP__98032, SNP__63437, SNP__94161, SNP__34738, SNP__88270, SNP__2880, SNP__36300, and SNP__77712.

Maize (*Zea mays* L.) is often referred to as corn in the United States. As used herein, a maize "plant" can be a whole plant, any part thereof, or a cell or tissue culture derived from a plant. Thus, the term "plant" can refer to any of whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

Pursuant to the present invention, ear productivity traits may include, for example, measurable traits such as kernel row number (KRN), kernel count (KC), kernel weight (KW), average kernel weight (AKW), cob weight (CW), cob length (CL), cob diameter (CD), and seedling dry weight (SDW).

A QTL is a polymorphic genetic locus with at least two alleles that differentially affect the expression of a continuously distributed phenotypic trait, such as the measurable ear productivity traits described herein.

As used herein, a marker is a nucleotide sequence or encoded product thereof (e.g., a protein) used as a point of reference. For markers to be useful at detecting recombinations, they need to detect differences, or polymorphisms, within the population being monitored. For molecular markers, this means differences at the DNA level due to polynucleotide sequence differences (e.g., simple sequence repeats ("SSRs"), restriction fragment length polymorphisms ("RFLPs"), amplified fragment length polymorphisms ("AFLPs"), single nucleotide polymorphisms ("SNPs"). All markers are used to define a specific locus on the maize genome. Large numbers of these markers have been mapped. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage where the trait can be expressed.

The genomic variability of a marker can be of any origin, for example, insertions, deletions, duplications, repetitive elements, point mutations, recombination events, or the presence and sequence of transposable elements. Molecular markers can be derived from genomic or expressed nucleic acids (e.g., ESTs) and can also refer to nucleic acids used as probes or primer pairs capable of amplifying sequence fragments via the use of PCR-based methods. A large number of maize molecular markers are known in the art, and are published or available from various sources.

In the context of the present invention, a QTL associated with an ear productivity trait means a nucleic acid and a phenotypic trait that are in linkage disequilibrium, i.e., the nucleic acid and the trait are found together in progeny plants more often than if the nucleic acid and phenotype segregated separately.

Recombination frequency measures the extent to which a molecular marker is linked with a QTL. Lower recombination frequencies, typically measured in centiMorgans ("cM"), indicate greater linkage between the QTL and the molecular marker. The extent to which two features are linked is often referred to as the genetic distance. The genetic distance is also typically related to the physical distance between the marker and the QTL. However, certain biological phenomenon (including recombinational "hot spots") can affect the relationship between physical distance and genetic distance. Generally, the usefulness of a molecular marker is determined by the genetic and physical distance between the marker and the selectable trait of interest. The linkage relationship between a molecular marker and a phenotype is given as a "probability" or "adjusted probability." Linkage can be expressed as a desired limit or range. For example, in some embodiments, any marker is linked (genetically and physically) to any other marker when the markers are separated by less than 50, 40, 30, 25, 20, or 15 map units (or cM). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

Data provided herein set forth a "logarithm of odds (LOD) value" or "LOD score" (Risch, "Genetic Linkage: Interpreting LOD Scores," *Science* 255:803-804 (1992), which is hereby incorporated by reference in its entirety). This is used in interval mapping to describe the degree of linkage between two marker loci. A LOD score of three (3.0) between two markers indicates that linkage is 1000 times more likely than no linkage, while a LOD score of two (2.0) indicates that linkage is 100 times more likely than no linkage. LOD scores greater than or equal to two (2.0) may be used to detect linkage.

According to the present invention, genomic DNA from a maize plant, germplasm, pollen, or seed is analyzed for the presence of a molecular marker linked to a QTL associated with an ear productivity trait in maize. Context DNA sequences for QTLs of the present invention are identified in the tables of FIGS. 3A-B (SEQ ID NOs:1-39) and FIGS. 5A-D (SEQ ID NOs:118-143). The complete genomic sequence of Maize has been published (Schnable et al., "The B73 Maize Genome: Complexity, Diversity and Dynamics," *Science* 326(5956):1112-1115 (2009), which is hereby incorporated by reference in its entirety) and may be helpful in carrying out the methods of the present invention. Analyzing genomic DNA from a maize plant, germplasm, pollen, or seed to determine the presence of a molecular marker corresponding to genetic polymorphisms between members of a population can be carried out by methods well-established in the art. These include, e.g., DNA sequencing, PCR-based sequence specific amplification methods, detection of RFLP, detection of isozyme markers, detection of polynucleotide polymorphisms by allele specific hybridization, detection of amplified variable sequences of the plant genome, detection of self-sustained sequence replication, detection of SSRs, detection of SNPs, or detection of AFLPs. Well-established methods are also known for the detection of expressed sequence tags ("ESTs") and SSR markers derived from EST sequences and randomly amplified polymorphic DNA.

The methods of the present invention may involve an automated system for detecting markers and/or correlating the markers with a desired phenotype (e.g., ear productivity). Thus, a typical system can include a set of marker probes or primers configured to detect at least one favorable allele of one or more marker locus associated with an ear productivity trait. These probes or primers are configured to detect the marker alleles described herein, e.g., using any available allele detection format, e.g., solid or liquid phase array based detection, microfluidic-based sample detection, etc.

The typical system includes a detector that is configured to detect one or more signal outputs from the set of marker probes or primers, or amplicon thereof, thereby identifying the presence or absence of the allele. A wide variety of signal detection apparatus are available, including photo multiplier tubes, spectrophotometers, CCD arrays, arrays and array scanners, scanning detectors, phototubes and photodiodes, microscope stations, galvo-scans, microfluidic nucleic acid amplification detection appliances, and the like. The precise configuration of the detector will depend, in part, on the type of label used to detect the marker allele, as well as the instrumentation that is most conveniently obtained for the user. Detectors that detect fluorescence, phosphorescence, radioactivity, pH, charge, absorbance, luminescence, temperature, magnetism or the like can be used. Typical detector examples include light (e.g., fluorescence) detectors or radioactivity detectors. For example, detection of a light emission (e.g., a fluorescence emission) or other probe label is indicative of the presence or absence of a marker allele. Fluorescent detection is generally used for detection of amplified nucleic acids (however, upstream and/or downstream operations can also be performed on amplicons, which can involve other detection methods). In general, the detector detects one or more label (e.g., light) emission from a probe label, which is indicative of the presence or absence of a marker allele.

The detector(s) optionally monitors one or a plurality of signals from an amplification reaction. For example, the detector can monitor optical signals which correspond to "real time" amplification assay results.

System instructions that correlate the presence or absence of the favorable allele with the predicted tolerance are also a feature of the invention. For example, the instructions can include at least one look-up table that includes a correlation between the presence or absence of the favorable alleles and the predicted ear productivity trait. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector. As noted, in one typical example, the system instructions include at least one look-up table that includes a correlation between the presence or absence of the favorable alleles and predicted tolerance or improved tolerance. The instructions also typically include instructions providing a user interface with the system, e.g., to permit a user to view results of a sample analysis and to input parameters into the system.

The system typically includes components for storing or transmitting computer readable data representing or designating the alleles detected by the methods of the present invention, e.g., in an automated system. The computer readable media can include cache, main, and storage memory and/or other electronic data storage components (hard drives, floppy drives, storage drives, etc.) for storage of computer code. Data representing alleles detected by the method of the present invention can also be electronically, optically, or magnetically transmitted in a computer data signal embodied in a transmission medium over a network such as an intranet or internet or combinations thereof. The system can also, or alternatively, transmit data via wireless, or other available transmission alternatives.

During operation, the system typically comprises a sample that is to be analyzed, such as a plant tissue, or material isolated from the tissue such as genomic DNA, amplified genomic DNA, cDNA, amplified cDNA, RNA, amplified RNA, or the like.

Automated systems for detecting markers and/or correlating the markers with a desired phenotype may involve data entering a computer which corresponds to physical objects or processes external to the computer, e.g., a marker allele, and a process that, within a computer, causes a physical transformation of the input signals to different output signals. In other words, the input data, e.g., amplification of a particular marker allele, is transformed to output data, e.g., the identification of the allelic form of a chromosome segment. The process within the computer is a set of instructions, or program, by which positive amplification or hybridization signals are recognized by the integrated system and attributed to individual samples as a genotype. Additional programs correlate the identity of individual samples with phenotypic values or marker alleles, e.g., statistical methods. In addition there are numerous e.g. C/C++ programs for computing, Delphi and/or Java programs for GUI interfaces, and productivity tools (e.g. Microsoft Excel and/or SigmaPlot) for charting or creating look up tables of relevant allele-trait correlations. Other useful software tools in the context of the integrated systems of the invention include statistical packages such as SAS, Genstat, Matlab, Mathematica, and S-Plus and genetic modeling packages such as QU-GENE. Furthermore, additional programming languages such as visual basic are also suitably employed in the integrated systems.

By way of example, ear productivity marker allele values assigned to a population of progeny descending from crosses between elite lines are recorded in a computer readable medium, thereby establishing a database corresponding tolerance alleles with unique identifiers for members of the population of progeny. Any file or folder, whether custom-made or commercially available (e.g., from Oracle or Sybase) suitable for recording data in a computer readable medium is acceptable as a database in the context of the present invention. Data regarding genotype for one or more molecular markers, e.g. SSR, RFLP, AFLP, SNP, isozyme markers or other markers as described herein, are similarly recorded in a computer accessible database. Optionally, marker data is obtained using an integrated system that automates one or more aspects of the assay (or assays) used to determine marker genotype. In such a system, input data corresponding to genotypes for molecular markers are relayed from a detector, e.g., an array, a scanner, a CCD, or other detection device directly to files in a computer readable medium accessible to the central processing unit. A set of system instructions (typically embodied in one or more programs) encoding the correlations between tolerance and the alleles of the invention is then executed by the computational device to identify correlations between marker alleles and predicted trait phenotypes.

Typically, the system also includes a user input device, such as a keyboard, a mouse, a touchscreen, or the like, for, e.g., selecting files, retrieving data, reviewing tables of maker information, etc., and an output device (e.g., a monitor, a printer, etc.) for viewing or recovering the product of the statistical analysis.

Integrated systems comprising a computer or computer readable medium comprising set of files and/or a database with at least one data set that corresponds to the marker alleles herein are provided. The system optionally also includes a user interface allowing a user to selectively view one or more of these databases. In addition, standard text manipulation software such as word processing software (e.g. MICROSOFT® Word or COREL® WORDPERFECT®) and database or spreadsheet software (e.g., spreadsheet software such as MICROSOFT® EXCEL®, COREL° QUATTRO PRO®, or database programs such as MICROSOFT® ACCESS® or PARADOX®) can be used in conjunction with a user interface (e.g., a GUI in a standard operating system such as a WINDOWS®, MACINTOSH®, UNIX®, or LINUX® systems) to manipulate strings of characters corresponding to the alleles or other features of the database.

The system may optionally include components for sample manipulation, e.g. incorporating robotic devices. For example, a robotic liquid control armature for transferring solutions (e.g., plant cell extracts) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support is commonly a feature of the integrated system. Many such automated robotic fluid handling systems are commercially available. For example, a variety of automated systems are available from Caliper Technologies (Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). As an alternative to conventional robotics, microfluidic systems for performing fluid handling and detection are now widely available, e.g., from Caliper Technologies Corp. (Hopkinton, Mass.) and Agilent technologies (Palo Alto, Calif.).

Systems for molecular marker analysis can include a digital computer with one or more of high-throughput liquid control software, image analysis software for analyzing data from marker labels, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes hybridized, e.g., to markers on a solid support operably linked to the digital computer. The image scanner interfaces with the image analysis software to provide a measurement of, e.g., nucleic acid probe label intensity upon hybridization to an arrayed sample nucleic acid population (e.g., comprising one or more markers), where the probe label intensity measurement is interpreted by the data interpretation software to show whether, and to what degree, the labeled probe hybridizes to a marker nucleic acid (e.g., an amplified marker allele). The data so derived is then correlated with sample identity, to determine the identity of a plant with a particular genotype(s) for particular markers or alleles, e.g., to facilitate marker assisted selection of maize plants with favorable allelic forms of chromosome segments involved in agronomic performance (e.g., ear productivity traits).

Optical images, e.g., hybridization patterns viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing, and analyzing a digitized video or digitized optical image, e.g., using PC (INTEL® x86 or PENTIUM® chip-compatible MS-DOS®, OS/2®, WINDOWS®, WINDOWS® NT or WINDOWS® 95 based machines), MACINTOSH®, LINUX®, or UNIX® based (e.g. SUN® work station) computers.

According to one embodiment, the ear productivity trait is kernel row number (KRN) and the marker is selected from L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP__77055, SNP__81248, SNP__82913, SNP__90380, SNP__11948, SNP__61221, SNP__70805, SNP__94161, SNP__2880, and SNP__36300.

In another embodiment, the ear productivity trait is cob weight (CW) and the marker is selected from SNP__98111, SNP__32823, SNP__4623, SNP__90941, SNP__27764, SNP__95039, SNP__75795, SNP__34738, and SNP__77712.

In yet another embodiment, the ear productivity trait is cob diameter (CD) and the marker is selected from SNP__90941, SNP__82913, SNP__93907, SNP__105143, SNP__43846, SNP__98032, SNP__88270, and SNP__77712.

In still another embodiment, the ear productivity trait is cob length (CL) and the marker is selected from SNP__35511, SNP__19249, and SNP__49724.

In another embodiment, the ear productivity trait is kernel weight (KW) and the marker is selected from SNP__79262, SNP__9084, and SNP__84372.

In yet another embodiment, the ear productivity trait is kernel count (KC) and the marker is selected from SNP__9084, SNP__99055, SNP__45551, SNP__89298__2, SNP__51496, and SNP__63437.

In addition to the markers identified herein, other markers linked to the markers described herein can be used to predict ear productivity in a maize plant and are therefore also useful in carrying out the methods of the present invention. This includes any marker within, e.g., 50 cM of the markers associated with ear productivity at a p-level ≤0.01 in the association analysis. The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart.

After a desired phenotype and a polymorphic chromosomal locus, e.g., a marker locus or QTL, are determined to segregate together, it is possible to use those polymorphic loci to select for alleles corresponding to the desired phenotype—a process called marker-assisted selection ("MAS"). In brief, a nucleic acid corresponding to the marker nucleic acid is detected in a biological sample from a plant to be selected. This detection can take the from of hybridization of a probe nucleic acid to a marker, e.g., using allele-specific hybridization, Southern analysis, northern analysis, in situ hybridization, hybridization of primers followed by PCR amplification of a region of the marker, or the like. A variety of procedures for detecting markers are described herein. After the presence (or absence) of a particular marker in the biological sample is verified, the plant is selected, i.e., used to make progeny plants by selective breeding.

Although particular marker alleles can show co-segregation with increased ear productivity, the marker locus is not necessarily responsible for the expression of ear productivity phenotypes. For example, it is not a requirement that the marker polynucleotide sequence be part of a gene that imparts increased ear productivity (for example, be part of the gene open reading frame). The association between a specific marker allele and a particular ear productivity phenotype is due to the original "coupling" linkage phase between the marker allele and the allele in the ancestral maize line from which the allele originated. Eventually, with repeated recombination, crossing over events between the marker and genetic locus can change this orientation. For this reason, the favorable marker allele may change depending on the linkage phase that exists within the parent used to create segregating populations. This does not change the fact that the marker can be used to monitor segregation of the phenotype. It only changes which marker allele is considered favorable in a given segregating population. Chromosomal intervals (i.e. any and all intervals defined by any of the markers of the present invention) that correlate with ear productivity are provided herein.

A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as a marker for ear productivity traits. The intervals described herein are set forth in Tables 2 and 4, and encompass markers that co-segregate with ear productivity traits. The clustering of markers occurs in relatively small domains on the chromosomes, indicating the presence of a gene controlling the trait of interest in those chromosome regions.

Maize breeders desire combinations of desirable traits to develop improved maize varieties. Screening large numbers of samples by non-molecular methods (e.g., trait evaluation in maize plants) can be expensive, time consuming, and unreliable. Use of the polymorphic markers described herein genetically linked to ear productivity loci provide effective methods for selecting high-yielding varieties in breeding programs. For example, one advantage of marker-assisted selection over field evaluations is that MAS can be done at any time of year, regardless of the growing season. Moreover, environmental effects are largely irrelevant to marker-assisted selection.

When a plant population is segregating for multiple loci affecting one or multiple traits, e.g., multiple loci involved in ear productivity, or multiple loci each involved in ear productivity, the efficiency of MAS compared to phenotypic screening becomes even greater, because all of the loci can be evaluated in the lab together from a single sample of DNA. In the present invention, markers of the present invention can be assayed simultaneously or sequentially in a single sample or population of samples.

Thus, another aspect of the present invention is directed to a method of selecting a maize plant with desired ear productivity trait. This method involves detecting in a maize plant, germplasm, seed, or pollen at least one allele of a marker locus that is associated with a desired ear productivity trait, where the one or more marker locus localizes within a chromosome interval defined by and including L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP__35511, SNP__98111, SNP__23951, SNP__79262, SNP__19249, SNP__9084, SNP__99055, SNP__77055, SNP__45551, SNP__30953, SNP__84678, SNP__89298_2, SNP__32823, SNP__4623, SNP__90941, SNP__81248, SNP__82913, SNP__93907, SNP__90380, SNP__49724, SNP__51496, SNP__11948, SNP__18689, SNP__61221, SNP__105143, SNP__84372, SNP__27764, SNP__95039, SNP__75795, SNP__70805, SNP__43846, SNP__98032, SNP__63437, SNP__94161, SNP__34738, SNP__88270, SNP__2880, SNP__36300, and SNP__77712. A maize plant with a desired ear productivity trait is selected by selecting the maize plant comprising the at least one allele of the marker locus.

In one embodiment, selecting the maize plant pursuant to this method of the present invention occurs as part of a breeding program to improve a maize variety's ear productivity. Breeding programs are well-known in the art and may include, e.g., crossing, making hybrids, backcrossing, self-crossing, double haploid breeding, and/or combinations thereof.

Field crops are bred through techniques that take advantage of the plant's method of pollination. A plant is self-pollinated if pollen from one flower is transferred to the same or another flower of the same plant. A plant is sib pollinated when individuals within the same family or line are used for pollination. A plant is cross-pollinated if the pollen comes from a flower on a different plant from a different family or line.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of heterogeneous plants that differ genetically and will not be uniform.

Maize can be bred by both self-pollination (self-crossing) and cross-pollination (crossing) techniques. Maize has separate male and female flowers on the same plant, located on the tassel and the ear, respectively.

Crossing means the fusion of gametes via pollination to produce progeny (i.e., cells, seeds, or plants). The term encompasses both sexual crosses (the pollination of one plant by another) and selfing (self-pollination, i.e., when the pollen and ovule are from the same plant). Natural pollination occurs in maize when wind blows pollen from the tassels to the silks that protrude from the tops of the ears. Large scale commercial maize hybrid production, as it is practiced today, requires the use of some form of male sterility system which controls or inactivates male fertility. A reliable method of controlling male fertility in plants also offers the opportunity for improved plant breeding. This is especially true for development of maize hybrids, which relies upon some sort of male sterility system. There are several ways in which a maize plant can be manipulated so that is male sterile. These include use of manual or mechanical emasculation (or detasseling), cytoplasmic genetic male sterility, nuclear genetic male sterility, gametocides and the like, which are discussed infra.

The development of a hybrid maize variety in a maize plant breeding program involves three steps: (1) the selection of plants from various germplasm pools for initial breeding crosses; (2) the selfing of the selected plants from the breeding crosses for several generations to produce a series of inbred lines, which, individually breed true and are highly uniform; and (3) crossing a selected inbred line with an unrelated inbred line to produce the hybrid progeny ($F_1$). After a sufficient amount of inbreeding, successive filial generations will merely serve to increase seed of the developed inbred. Preferably, an inbred line should comprise homozygous alleles at about 95% or more of its loci.

As noted above, hybrid maize seed is often produced by a male sterility system incorporating manual or mechanical detasseling. By way of example, alternate strips of two inbred varieties of maize can be planted in a field, and the pollen-bearing tassels removed from one of the inbreds (female) prior to pollen shed. Provided that there is sufficient isolation from sources of foreign maize pollen, the ears of the detasseled inbred will be fertilized only from the other inbred (male), and the resulting seed is therefore hybrid and will form hybrid plants.

The laborious detasseling process can be avoided by using cytoplasmic malesterile ("CMS") inbreds. Plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. The same hybrid seed, a portion produced from detasseled fertile maize and a portion produced using the CMS system can be blended to insure that adequate pollen loads are available for fertilization when the hybrid plants are grown.

There are several methods of conferring genetic male sterility available, such as multiple mutant genes at separate locations within the genome that confer male sterility, as disclosed in U.S. Pat. Nos. 4,654,465 and 4,727,219 to Brar et al., which are hereby incorporated by reference in their entirety, and chromosomal translocations as described in U.S. Pat. Nos. 3,861,709 and 3,710,511 to Patterson, which are hereby incorporated by reference in their entirety. In addition to these methods, U.S. Pat. No. 5,432,068 to Albertsen et al., which is hereby incorporated by reference in its entirety, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on" the promoter, which in turn allows the gene that confers male fertility to be transcribed.

There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant. See, e.g., PCT Publication No. WO 90/08828 to Fabinjanski et al., which is hereby incorporated by reference in its entirety.

The use of male sterile inbreds is but one factor in the production of maize hybrids. The development of maize hybrids in a maize plant breeding program requires, in general, the development of homozygous inbred lines, the crossing of these lines, and the evaluation of the crosses. Maize plant breeding programs combine the genetic backgrounds from two or more inbred lines or various other germplasm sources into breeding populations from which new inbred lines are developed by selfing and selection of desired phenotypes. Hybrids also can be used as a source of plant breeding material or as source populations from which to develop or derive new maize lines. Plant breeding techniques known in the art and used in a maize plant breeding program include, but are not limited to, recurrent selection, backcrossing, double haploids, pedigree breeding, restriction fragment length polymorphism enhanced selection, genetic marker enhanced selection, and transformation. Often a combination of these techniques are used. The inbred lines derived from hybrids can be developed using plant breeding techniques as described herein. New inbreds are crossed with other inbred lines and the hybrids from these crosses are evaluated to determine which of those have commercial potential.

Backcrossing refers to the process whereby hybrid progeny are repeatedly crossed back to one of the parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot et al., "Marker-assisted Backcrossing: A Practical Example," *Techniques et Utilisations des Marqueurs Moleculaires Les Colloques*, vol. 72, pp. 45-56 (1995) and Openshaw et al., "Marker-assisted Selection in Backcross Breeding," *Analysis of Molecular Marker Data*, pp. 41-43 (1994), which are hereby incorporated by reference in their entirety. The initial cross gives rise to the $F_1$ generation; the term "BC1" then refers to the second use of the recurrent parent, "BC2" refers to the third use of the recurrent parent, and so on.

Backcrossing can be used to improve inbred lines and a hybrid which is made using those inbreds. Backcrossing can be used to transfer a specific desirable trait from one line, the donor parent, to an inbred called the recurrent parent which has overall good agronomic characteristics yet that lacks the desirable trait. This transfer of the desirable trait into an inbred line with overall good agronomic characteristics can be accomplished by first crossing a recurrent parent to a donor parent (non-recurrent parent). The progeny of this cross is then mated back to the recurrent parent followed by selection in the resultant progeny for the desired trait to be transferred from the non-recurrent parent. Typically after four or more backcross generations with selection for the desired trait, the progeny will contain essentially all genes of the recurrent parent except for the genes controlling the desired trait. But the number of backcross generations can be less if molecular markers are used during the selection or elite germplasm is used as the donor parent. The last backcross generation is then selfed to give pure breeding progeny for the gene(s) being transferred.

Backcrossing can also be used in conjunction with pedigree breeding to develop new inbred lines. For example, an $F_1$ can be created that is backcrossed to one of its parent lines to create a BC1. Progeny are selfed and selected so that the newly developed inbred has many of the attributes of the recurrent parent and some of the desired attributes of the non-recurrent parent.

Recurrent selection is a method used in a plant breeding program to improve a population of plants. The method entails individual plants cross pollinating with each other to form progeny which are then grown. The superior progeny are then selected by any number of methods, which include individual plant, half sib progeny, full sib progeny, selfed progeny, and topcrossing. The selected progeny are cross pollinated with each other to form progeny for another population. This population is planted and again superior plants are selected to cross pollinate with each other. Recurrent selection is a cyclical process and, therefore, can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds. Mass selection is a useful technique when used in conjunction with molecular marker enhanced selection.

The production of double haploids can also be used in a breeding program. Double haploids are produced by the doubling of a set of chromosomes (1N) from a heterozygous plant to produce a completely homozygous individual. See, e.g., Wan et al., "Efficient Production of Doubled Haploid Plants Through Colchicine Treatment of Anther-Derived Maize Callus." *Theoretical and Applied Genetics* 77:889-892 (1989) and U.S. Patent Application Publication No. 2003/0005479, which are hereby incorporated by reference in their entirety. This can be advantageous because the process omits the generations of selfing needed to obtain a homozygous plant from a heterozygous source. Double haploid breeding methods may be used at any step in a breeding process. For example, instead of selfing out of the hybrid produced from the inbred, one could first cross the hybrid to either a parent line or a different inbred, and then self out of that cross.

A further aspect of the present invention is directed to a maize plant selected pursuant to the methods of the present invention.

Marker loci of the present invention can be introgressed into any desired genomic background, germplasm, plant, line, variety, etc., as part of an overall MAS breeding program designed to enhance maize yield, or for any other purpose. Thus, another aspect of the present invention is directed to a method for reliably and predictably introgressing an improved ear productivity trait into a maize line. This method involves selecting plants for breeding based upon the presence of a molecular marker selected from L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP__35511, SNP__98111, SNP__23951, SNP__79262, SNP__19249, SNP__9084, SNP__99055, SNP__77055, SNP__45551, SNP__30953, SNP__84678, SNP__89298__2, SNP__32823, SNP__4623, SNP__90941, SNP__81248, SNP__82913, SNP__93907, SNP__90380, SNP__49724, SNP__51496, SNP__11948, SNP__18689, SNP__61221, SNP__105143, SNP__84372, SNP__27764, SNP__95039, SNP__75795, SNP__70805, SNP__43846, SNP__98032, SNP__63437, SNP__94161, SNP__34738, SNP__88270, SNP__2880, SNP__36300, and SNP__77712.

Introgression refers to the transmission of a desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene or a selected allele of a marker or QTL.

Offspring possessing the desired allele can be repeatedly backcrossed to a line having a desired genetic background and selected for the desired allele, to result in the allele becoming fixed in a selected genetic background. For example, markers described herein may be introgressed into a recurrent parent. The recurrent parent line with the introgressed gene or locus may then have a desired ear productivity trait.

Another aspect of the present invention is directed to a method for producing a maize line having a desired ear productivity trait. This method involves providing a first maize line having a molecule marker selected from the group consisting of L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP_35511, SNP_98111, SNP_23951, SNP_79262, SNP_19249, SNP_9084, SNP_99055, SNP_77055, SNP_45551, SNP_30953, SNP_84678, SNP_89298_2, SNP_32823, SNP_4623, SNP_90941, SNP_81248, SNP_82913, SNP_93907, SNP_90380, SNP_49724, SNP_51496, SNP_11948, SNP_18689, SNP_61221, SNP_105143, SNP_84372, SNP_27764, SNP_95039, SNP_75795, SNP_70805, SNP_43846, SNP_98032, SNP_63437, SNP_94161, SNP_34738, SNP_88270, SNP_2880, SNP_36300, and SNP_77712, the molecular marker mapping to a genomic locus associated with a desired ear productivity trait. The desired ear productivity trait is introgressed into a maize line by selecting progeny plants for further breeding based upon the presence of the molecular marker to provide a recombinant maize line having the desired ear productivity trait.

Another aspect of the present invention is directed to a kit for selecting a maize plant by marker assisted selection of a QTL associated with a desired ear productivity trait. The kit includes primers for detecting at least one ear productivity trait marker locus selected from the group consisting of L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP_35511, SNP_98111, SNP_23951, SNP_79262, SNP_19249, SNP_9084, SNP_99055, SNP_77055, SNP_45551, SNP_30953, SNP_84678, SNP_89298_2, SNP_32823, SNP_4623, SNP_90941, SNP_81248, SNP_82913, SNP_93907, SNP_90380, SNP_49724, SNP_51496, SNP_11948, SNP_18689, SNP_61221, SNP_105143, SNP_84372, SNP_27764, SNP_95039, SNP_75795, SNP_70805, SNP_43846, SNP_98032, SNP_63437, SNP_94161, SNP_34738, SNP_88270, SNP_2880, SNP_36300, and SNP_77712. The kit also includes instructions for using the primers for detecting the ear productivity trait marker locus and correlating the locus with an improved ear productivity trait.

Suitable primers for detecting ear productivity trait marker loci of the present invention can be generated from the sequence data provided in FIGS. 3A-B and FIGS. 5A-D. In one embodiment, primers are selected from those set forth in FIGS. 4A-B.

Another aspect of the present invention is directed to an isolated nucleic acid comprising a QTL associated with an ear productivity trait in maize. The QTL is proximal to a locus corresponding to a marker selected from the group consisting of L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP_35511, SNP_98111, SNP_23951, SNP_79262, SNP_19249, SNP_9084, SNP_99055, SNP_77055, SNP_45551, SNP_30953, SNP_84678, SNP_89298_2, SNP_32823, SNP_4623, SNP_90941, SNP_81248, SNP_82913, SNP_93907, SNP_90380, SNP_49724, SNP_51496, SNP_11948, SNP_18689, SNP_61221, SNP_105143, SNP_84372, SNP_27764, SNP_95039, SNP_75795, SNP_70805, SNP_43846, SNP_98032, SNP_63437, SNP_94161, SNP_34738, SNP_88270, SNP_2880, SNP_36300, and SNP_77712.

A further aspect of the present invention is directed to a transgenic plant comprising a recombinant nucleic acid genetically linked to a locus in maize, where the locus is proximal to a QTL associated with an ear productivity trait in a maize plant, and where the locus corresponds to a marker selected from the group consisting of L00401, L004011 c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP_35511, SNP_98111, SNP_23951, SNP_79262, SNP_19249, SNP_9084, SNP_99055, SNP_77055, SNP_45551, SNP_30953, SNP_84678, SNP_89298_2, SNP_32823, SNP_4623, SNP_90941, SNP_81248, SNP_82913, SNP_93907, SNP_90380, SNP_49724, SNP_51496, SNP_11948, SNP_18689, SNP_61221, SNP_105143, SNP_84372, SNP_27764, SNP_95039, SNP_75795, SNP_70805, SNP_43846, SNP_98032, SNP_63437, SNP_94161, SNP_34738, SNP_88270, SNP_2880, SNP_36300, and SNP_77712.

Methods of producing recombinant nucleic acids for purposes of making transgenic plants are well-known. In one embodiment, the present invention utilizes recombinant nucleic acid sequences that are genetically linked to a locus in maize, where the locus is proximal to a QTL associated with an ear productivity trait. The locus corresponds to one or more of the markers described herein. Nucleic acid sequences for making transgenic plants according to the present invention may be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pBI121, pBI525, pG-Cha, p35S-Cha, pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pET series (see Studier et al., "Use of T7 RNA Polymerase to Direct Expression of Cloned Genes," *Gene Expression Technology* vol. 185 (1990), which is hereby incorporated by reference in its entirety), and any derivatives thereof.

Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor, N.Y., Cold Spring Harbor Press (1989), and Ausubel et al., *Current*

*Protocols in Molecular Biology*, New York, N.Y., John Wiley & Sons (1989), which are hereby incorporated by reference in their entirety.

In preparing a nucleic acid vector for expression, the various nucleic acid sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA ("T-DNA") is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley et al., "Expression of Bacterial Genes in Plant Cells," *Proc. Nat'l Acad. Sci.* 80:4803-4807 (1983), which is hereby incorporated by reference in its entirety).

Further improvement of this technique led to the development of the binary vector system (Bevan, "Binary *Agrobacterium* Vectors for Plant Transformation," *Nucleic Acids Res.* 12:8711-8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly-used vector is pBin19 (Frisch et al., "Complete Sequence of the Binary Vector Bin19," *Plant Molec. Biol.* 27:405-409 (1995), which is hereby incorporated by reference in its entirety). Any appropriate vectors now known or later described for genetic transformation are suitable for use with the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used. Tissue-specific and organ-specific promoters can also be used.

A constitutive promoter is a promoter that directs expression of a gene throughout the development and life of an organism. Examples of some constitutive promoters that are widely used for inducing expression of transgenes include the nopaline synthase ("NOS") gene promoter, from *Agrobacterium tumefaciens* (U.S. Pat. No. 5,034,322 to Rogers et al., which is hereby incorporated by reference in its entirety), the cauliflower mosaic virus (CaMV) 35S and 19S promoters (U.S. Pat. No. 5,352,605 to Fraley et al., which is hereby incorporated by reference in its entirety), those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide, or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter is a glucocorticoid-inducible promoter (Schena et al., "A Steroid-Inducible Gene Expression System for Plant Cells," *Proc. Natl. Acad. Sci.* 88:10421-5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog (Schena et al., "A Steroid-Inducible Gene Expression System for Plant Cells," *Proc. Natl. Acad. Sci. USA* 88:10421-5 (1991); Aoyama et al., "A Glucocorticoid-Mediated Transcriptional Induction System in Transgenic Plants," *Plant J.* 11:605-612 (1997); and McNellis et al., "Glucocorticoid-Inducible Expression of a Bacterial Avirulence Gene in Transgenic *Arabidopsis* Induces Hypersensitive Cell Death," *Plant J.* 14(2):247-57 (1998), which are hereby incorporated by reference in their entirety). In addition, inducible promoters include promoters that function in a tissue specific manner to regulate the gene of interest within selected tissues of the plant. Examples of such tissue specific or developmentally regulated promoters include seed, flower, fruit, or root specific promoters as are well known by those of ordinary skill in the art (U.S. Pat. No. 5,750,385 to Shewmaker et al., which is hereby incorporated by reference in its entirety).

A number of tissue- and organ-specific promoters have been developed for use in genetic engineering of plants (Potenza et al., "Targeting Transgene Expression in Research, Agricultural, and Environmental Applications: Promoters Used in Plant Transformation," *In Vitro Cell. Dev. Biol. Plant* 40:1-22 (2004), which is hereby incorporated by reference in its entirety). Examples of such promoters include those that are floral-specific (Annadana et al., "Cloning of the Chrysanthemum UEP1 Promoter and Comparative Expression in Florets and Leaves of *Dendranthema grandiflora*," *Transgenic Res.* 11:437-445 (2002), which is hereby incorporated by reference in its entirety), seed-specific (Kluth et al., "5' Deletion of a gbss1 Promoter Region Leads to Changes in Tissue and Developmental Specificities," *Plant Mol. Biol.* 49:669-682 (2002), which is hereby incorporated by reference in its entirety), root-specific (Yamamoto et al., "Characterization of cis-acting Sequences Regulating Root-Specific Gene Expression in Tobacco," *Plant Cell* 3:371-382 (1991), which is hereby incorporated by reference in its entirety), fruit-specific (Fraser et al., "Evaluation of Transgenic Tomato Plants Expressing an Additional Phytoene Synthase in a Fruit-Specific Manner," *Proc. Natl. Acad. Sci. USA* 99:1092-1097 (2002), which is hereby incorporated by reference in its entirety), and tuber/storage organ-specific (Visser et al., "Expression of a Chimaeric Granule-Bound Starch Synthase-GUS Gene in Transgenic Potato Plants," *Plant Mol. Biol.* 17:691-699 (1991), which is hereby incorporated by reference in its entirety). Targeted expression of an introduced gene (transgene) is necessary when expression of the transgene could have detrimental effects if expressed throughout the plant. On the other hand, silencing a gene throughout a plant could also have negative effects. However, this problem could be avoided by localizing the silencing to a region by a tissue-specific promoter.

Nucleic acid constructs of the present invention include an operable 3' regulatory region, selected from among those which are capable of providing correct transcription termination and polyadenylation of mRNA for expression in the host cell of choice, operably linked to a nucleic acid molecule configured to silence BBTV. A number of 3' regulatory regions are known to be operable in plants. Exemplary 3' regulatory regions include, without limitation, the nopaline synthase ("nos") 3' regulatory region (Fraley et al., "Expression of Bacterial Genes in Plant Cells," *Proc. Nat'l Acad. Sci. USA* 80:4803-4807 (1983), which is hereby incorporated by reference in its entirety) and the cauliflower mosaic virus ("CaMV") 3' regulatory region (Odell et al., "Identification of DNA Sequences Required for Activity of the Cauliflower Mosaic Virus 35S Promoter," *Nature* 313(6005):810-812 (1985), which is hereby incorporated by reference in its entirety). Virtually any 3' regulatory region known to be operable in plants would be suitable for use in conjunction with the present invention.

The different components described supra can be ligated together to produce the expression systems which contain the nucleic acid constructs of the present invention, using well known molecular cloning techniques as described in Sambrook et al., *Molecular Cloning: A Laboratory Manual*, Second Edition Cold Spring Harbor, N.Y., Cold Spring Harbor Press (1989), and Ausubel et al. *Current Protocols in Molecular Biology*, New York, N.Y., John Wiley & Sons (1989), which are hereby incorporated by reference in their entirety.

Once the nucleic acid construct of the present invention has been prepared, it is ready to be incorporated into a host cell. Accordingly, another aspect of the present invention relates to a recombinant host cell containing one or more of the nucleic acid constructs of the present invention. Basically, this method is carried out by transforming a host cell with a nucleic acid construct of the present invention under conditions effective to achieve transcription of the nucleic acid molecule in the host cell. This is achieved with standard cloning procedures known in the art, such as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell. Methods of transformation may result in transient or stable expression of the nucleic acid under control of the promoter. Preferably, a nucleic acid construct of the present invention is stably inserted into the genome of the recombinant plant cell as a result of the transformation, although transient expression can serve an important purpose.

Plant tissue suitable for transformation includes leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue can be achieved by particle bombardment (Klein et al., "High-Velocity Microprojectiles for Delivering Nucleic Acids Into Living Cells," *Nature* 327:70-73 (1987), which is hereby incorporated by reference in its entirety), also known as biolistic transformation of the host cell, as disclosed in U.S. Pat. Nos. 4,945,050; 5,036,006; and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports* 14:6-12 (1995), which are hereby incorporated by reference in their entirety.

In particle bombardment, tungsten or gold microparticles (1 to 2 μm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. Other variations of particle bombardment, now known or hereafter developed, can also be used.

An appropriate method of stably introducing the nucleic acid construct into plant cells is to infect a plant cell with *Agrobacterium tumefaciens* or *Agrobacterium rhizogenes* previously transformed with the nucleic acid construct of the present invention. As described supra, the Ti (or R1) plasmid of *Agrobacterium* enables the highly successful transfer of a foreign nucleic acid molecule into plant cells. A variation of *Agrobacterium* transformation uses vacuum infiltration in which whole plants are used (Senior, "Uses of Plant Gene Silencing," *Biotechnology and Genetic Engineering Reviews* 15:79-119 (1998), which is hereby incorporated by reference in its entirety).

Yet another method of introduction is fusion of protoplasts with other entities, either minicells, cells, lysosomes, or other fusible lipid-surfaced bodies (Fraley et al., "Liposome-mediated Delivery of Tobacco Mosaic Virus RNA Into Tobacco Protoplasts: A Sensitive Assay for Monitoring Liposome-protoplast Interactions," *Proc. Natl. Acad. Sci. USA* 79:1859-63 (1982), which is hereby incorporated by reference in its entirety). The nucleic acid molecule may also be introduced into the plant cells by electroporation (Fromm et al., "Expression of Genes Transferred into Monocot and Dicot Plant Cells by Electroporation," *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. Other methods of transformation include polyethylene-mediated plant transformation, micro-injection, physical abrasives, and laser beams (Senior, "Uses of Plant Gene Silencing," *Biotechnology and Genetic Engineering Reviews* 15:79-119 (1998), which is hereby incorporated by reference in its entirety). The precise method of transformation is not critical to the practice of the present invention. Any method that results in efficient transformation of the host cell of choice is appropriate for practicing the present invention.

After transformation, the transformed plant cells must be regenerated. Plant regeneration from cultured protoplasts is described in Evans et al., *Handbook of Plant Cell Cultures, Vol.* 1, New York, N.Y., MacMillan Publishing Co. (1983); Vasil, ed., *Cell Culture and Somatic Cell Genetics of Plants*, Vol. I (1984) and Vol. III (1986), Orlando, Acad. Press; and Fitch et al., "Somatic Embryogenesis and Plant Regeneration from Immature Zygotic Embryos of Papaya (*Carica papaya* L.)," *Plant Cell Rep.* 9:320 (1990), which are hereby incorporated by reference in their entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the neomycin phosphotransferae II ("nptII") gene which confers kanamycin resistance (Fraley et al., "Expression of Bacterial Genes in Plant Cells," *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the transgene (Sambrook et al., *Molecular Cloning: A Laboratory Manual*, Cold Spring Harbor, N.Y., Cold Spring Harbor Press (1989), which is hereby incorporated by reference in its entirety).

In one embodiment, the transgenic plant is transformed with a bacterial artificial chromosome ("BAC"). A BAC is a cloning vector derived from the naturally occurring F factor of *Escherichia coli*. BACs can accept large inserts of a DNA sequence. In maize, a number of BACs, each containing a large insert of maize genomic DNA, have been assembled into contigs (overlapping contiguous genetic fragments, or "contiguous DNA"). BACs have a propensity for coming together to form contiguous stretches of DNA. A BAC "assembles" to a contig based on sequence alignment, if the BAC is sequenced, or via the alignment of its BAC fingerprint to the fingerprints of other BACs. The assemblies can be found using the Maize Genome Browser, which is publicly available on the internet.

EXAMPLES

The following examples are provided to illustrate embodiments of the present invention but are by no means intended to limit its scope.

Example 1

Detection of QTL and hQTL for Yield-Related Traits and Heterosis

Kernel row number (KRN), kernel count (KC), kernel weight (KW), average kernel weight (AKW), cob weight (CW), cob length (CL), cob diameter (CD), and seedling dry weight (SDW) were measured for above-ground tissues. These traits were selected based on the ability to measure them post-harvest over long periods in the lab and the ability to store samples and re-measure samples with outlying data points. The overall goal of this study was to identify: (1) regions of the genome that regulate yield-related traits and (2) regions of the genome that regulate the amount of heterosis for yield-related traits.

Genetic Stocks

The ISU 291R1SNP Map (N=1,016 markers) was developed using 291 IBM RILs. These RILs were self-pollinated and crossed onto both B73 and Mo17 inbred lines using pollen from the same male (RIL) plant. The seed from a single ear for each cross-type was used in all four biological replications when possible (the use of multiple seed sources was rare).

Seedling Dry Weight Experimental Design

The seedling dry weight experiment was conducted in a greenhouse to reduce environmental effects. Seedlings were grown with 15 hours of light each day. The 291 RILs and their crosses onto B73 and Mo17 were grown in sand benches along with B73, Mo17, B73×Mo17, and Mo17×B73. The design was a randomized complete block design (FIG. 1), where a RIL and its crosses to B73 and Mo17 (or the parent lines B73, Mo17, and their hybrids) were blocked together, but randomly assigned to a location among the sand benches. The parent lines were sampled more extensively within each replication (50 sets of ~5 seedlings per parent per replication). In each replication, average seedling dry weight at two weeks was recorded based on ~5 seedlings per line.

Due to seed availability, the RILs and their cross-types were divided into two groups for processing (Group A and Group B). For some replications, the planting was distributed over a two-day period. In such cases, half of the rep was planted (sand benches 1-3) on the first day, and half on the second (sand benches 3-6). Harvest was also distributed such that all plants (regardless of planting date) were harvested 2 weeks after planting.

Group A (198 RILs and their crosses to B73 and Mo17), 4 replications (Rep 1, Rep 2, Rep 3, Rep4, and Reps 1B and 2B) were planted and processed in the Fall of the first year and each planting included a single replication. Due to limited daylight in the winter strongly affecting plant growth in the sand benches, the remaining RILs (Group B) were processed in the Fall a year later (Reps 1B and 2B were discarded and regrown in the second season). For RILs or their hybrids failing to germinate in the first year, an alternative seed pack was selected and the RIL and its hybrids were added to the Group B replications in the second year. These instances were not common, however. Because the Group B replications were smaller (~100 RILs and their hybrids), two replications could fit within the greenhouse sand benches in a single growth period (Rep 3B, Rep 4B, Reps 1B-2B redo replications). To estimate the variance from the first year to the second, lines from both Group A (N=95 randomly selected) and Group B (N=all 110) were selected for an additional replication (Rep 5) in the second year.

At harvest, seedlings from a single row/genotype were pooled and stored in a pollination bag and the number of seedlings within the row was recorded. The samples were held in ~60° C. driers housed at the Iowa State University Agronomy Farm for 2-3 days, followed by weight measurements for all tissue within each bag. The per plant dry weight average (g) was calculated based on the total weight of the pooled plants divided by the number of plants in the row.

Adult-Stage Trait Experimental Design

For each of four biological replications, randomization was conducted with restrictions such that inbred and hybrid lines were kept in separate ranges to avoid competition. A triplet of ranges was comprised of 3, 50-row blocks where each block was randomly assigned to contain RIL, B73×RIL, or Mo17× RIL lines. The RIL ranges included 36-37 RILs, 5 B73, 5 Mo17, and 3-4 rows of fill seed/plants (to allow for even distribution of informative lines across the 24 ranges within each replication). Genotypes within the ranges of each triplet were arranged according to the design of the RIL range so that a given RIL and its crosses to B73 and Mo17 were in equivalent positions within neighboring ranges. Positions of the parental lines (B73, Mo17, and $F_1$ hybrids) were randomly assigned within each set of ranges, maintaining separation of inbred and hybrid lines.

Reps 1-2 and reps 3-4 were planted at the Iowa State University Johnson Farm in Ames, Iowa. Due to excessive flooding, the fourth biological replication was severely damaged and many rows failed to germinate. Thus, only Replications 1-3 were harvested for the QTL study.

Adult-Stage Tissue Sample Processing and Data Collection

The primary ear for each plant was harvested by hand. Harvest was conducted in an order such that within each replication, a given RIL and its hybrids with B73 and Mo17 were harvested, dried, stored, and measured on the same dates. At harvest, two identical harvest tags containing sample information and a unique barcode were affixed to each sample. Ears were then dried for 2-3 days at ~38° C.

Prior to shelling the kernels from the cobs, the number of rows of kernels was counted (KRN) and recorded for each sample. At the shelling stage, kernels from a single ear were stored in a seed envelope and the cob was stored in a sealable, plastic bag, each receiving one of the two identical barcoded labels. Thus, it is possible to relate the kernel and cob data for each plant.

Barcode scanners were used to automatically enter the unique sample identifier (field row and plant-in-row) into MICROSOFT® EXCEL®. Each measurement instrument was equipped to send digital data to a PC through an RS232 cable using WinWedge software (TALtech, Philadelphia, Pa.), allowing for efficient and reliable data entry.

Individual cobs were weighed (CW) using the ATL-822-I digital scale (Acculab, Bradford, Mass.). Cob maximum cob diameter (CD) and length (CL) were measured using a digital caliper (F.V. Fowler, Newton, Mass.). Kernels with mold damage or pest damage were manually filtered from each seed pack. Kernel number (KC) was measured using the Old Mill 850-3 seed counter (International Marketing and Design Co., San Antonio, Tex.). Immediately after, the total kernel weight (KW) for non-filtered kernels was measured using the digital scale (Acculab, Bradford, Mass.). For each sample, average kernel weights (AKW) were calculated by dividing the total weight (g) by the total kernel count (not including the "bad" kernels).

Statistical Analysis

Data were compiled into single spreadsheets for each trait. Quality checks were performed to identify improbable values. Such cases were individually investigated to either confirm the value or correct the error.

LS Means for each genotype were estimated in SAS (company) for the seedling dry weight experiment conducted in the greenhouse using the following model:
proc mixed data=one;
class exp rep sandbench section block crosstype scale;
model y=crosstype scale;
random exp sandbench section(sandbench) block(section sandbench) rep(exp)exp*sandbench exp*section(sandbench)exp*block(section sandbench) sandbench*rep (exp) section*rep(exp sandbench) block*rep(section sandbench exp).

LS Means for each genotype were estimated in SAS (company) using the following model for the field-based traits:
proc mixed data=one;
class rep range col genotype rangeblock dash;
model trait=rep genotype dash/outp=check;
random rangeblock(rep) range(rangeblock rep) col(rangeblock rep) range*col(rangeblock rep)

Mean estimates produced by these models (FIGS. 6A-U) were used for subsequent QTL mapping. The QTL mapping was conducted using custom R (Version 2.2.1) scripts authored by Dan Nettleton. For each trait and population (RIL, B73×RIL, Mo17×RIL), 11 QTL analyses were conducted (FIGS. 6A-U).

In addition to mapping each trait per se, QTL for high-parent heterosis ("HPH") and mid-parent heterosis ("MPH") were mapped in the B73×RIL and Mo17×RIL hybrids. HPH and MPH were calculated:

$$HPH=B73\times RIL-max[B73,RIL]$$

$$HPH=Mo17\times RIL-max[Mo17,RIL]$$

$$MPH=B73\times RIL-mean[B73,RIL]$$

$$MPH=Mo17\times RIL-mean[Mo17,RIL]$$

The resulting HPH and MPH values were then used as input for the QTL analysis. For each significant QTL, the magnitude and direction of effect, percentage variation explained by the QTL, and confidence intervals (1.5 LOD dropdown) were calculated.

Results

Quantitative measures of kernel traits (number of rows, count, weight, average weight), cob traits (length, diameter, and weight), and seedling dry weight were collected for 291 RILs and their hybrids (B73×RIL and Mo17×RIL) in addition to the inbred parents B73, Mo17, and their reciprocal $F_1$ hybrids. Although hybrids exhibit heterosis for many traits, not all quantitative traits exhibit heterosis (Table 1). Hybrids outperformed their inbred parents for average kernel weight, kernel count per ear, cob weight, cob length, and seedling dry weight. B73 appears dominant for the cob diameter and number of rows of kernels and outperformed the hybrids and Mo17 for both traits.

Multiple QTL were detected within each population and trait (Tables 1-2), some of which overlap across analysis type and trait measured. Using the 1.5 LOD dropdown to determine confidence intervals, ~⅔ of the 85 significant QTL exhibited interval sizes less than 20 cM, but the overall range is from 2.8-149.3 cM. Within traits, the favorable allele for QTL can differ (B73 or Mo17) and the magnitude of effect is variable (13% increase in amount of heterosis for cob weight on Chromosome 1, 6% increase in heterosis for average kernel weight on Chromosome 3).

TABLE 1

QTL Analyses Conducted

| No. | Analysis | Comparison | Trait Mapped |
|---|---|---|---|
| 1 | BxRIL | BxRIL$_{BB}$ vs BXRIL$_{MM}$ | BB vs BM |
| 2 | RIL | RIL$_{BB}$ vs RIL$_{MM}$ | BB vs MM |
| 3 | MxRIL | MxRIL$_{BB}$ vs MxRIL$_{MM}$ | BM vs MM |
| 4 | BxRIL HPH | BxRIL$_{BB}$ vs BxRIL$_{MM}$ | High-parent heterosis BB vs BM |
| 5 | MxRIL HPH | MxRIL$_{BB}$ vs MxRIL$_{MM}$ | High-parent heterosis BM vs MM |
| 6 | BxRIL MPH | BxRIL$_{BB}$ vs BxRIL$_{MM}$ | Mid-parent heterosis BB vs BM |
| 7 | MxRIL MPH | MxRIL$_{BB}$ vs MxRIL$_{MM}$ | Mid-parent heterosis BM vs MM |
| 8 | BxRIL % HPH | BxRIL$_{BB}$ vs BxRIL$_{MM}$ | % High-parent heterosis BB vs BM |
| 9 | MxRIL % HPH | MxRIL$_{BB}$ vs MxRIL$_{MM}$ | % High-parent heterosis BM vs MM |
| 10 | BxRIL % MPH | BxRIL$_{BB}$ vs BxRIL$_{MM}$ | % Mid-parent heterosis BB vs BM |
| 11 | MxRIL % MPH | MxRIL$_{BB}$ vs MxRIL$_{MM}$ | % Mid-parent heterosis BM vs MM |

TABLE 2

Significant QTL for All Traits

| Trait | Analysis | Sig. Marker | P-value[1] | Chr | cM | Confidence Interval[2] Lower cM | Confidence Interval[2] Upper cM | Length (cM) | Effect Size[3] | % Var[4] | Action[5] |
|---|---|---|---|---|---|---|---|---|---|---|---|
| CL | BxRIL | SNP_35511 | 0.006 | 1 | 73.2 | 71.7 | 102.9 | 31.2 | -8.37 | 0.07 | BB < BM |
| CW | M HPH | SNP_98111 | 0.004 | 1 | 78.4 | 73.2 | 84 | 10.8 | 2.18 | 0.07 | BM > MM |
| CW | M MPH | SNP_98111 | 0.012 | 1 | 78.4 | 74.9 | 215.4 | 140.5 | 1.89 | 0.06 | BM > MM |
| CW | M pHPH | SNP_98111 | 0.005 | 1 | 78.4 | 73.2 | 84 | 10.8 | 0.13 | 0.07 | BM > MM |
| CW | M pMPH | SNP_98111 | 0.006 | 1 | 78.4 | 74.9 | 84 | 9.1 | 0.15 | 0.07 | BM > MM |
| AKW | RIL | SNP_23951 | 0.034 | 1 | 95.3 | 79.3 | 106.4 | 27.1 | -0.02 | 0.06 | BB < MM |
| KW | BxRIL | SNP_79262 | 0.02 | 1 | 101.6 | 71.7 | 104.1 | 32.4 | -13.21 | 0.05 | BB < BM |
| CL | M pMPH | SNP_19249 | 0.042 | 1 | 175.6 | 168.2 | 194.7 | 26.5 | 0.05 | 0.05 | BM > MM |
| KC | M MPH | SNP_9084 | 0.011 | 3 | 87.5 | 82.5 | 90.6 | 8.1 | 39.62 | 0.06 | BM > MM |
| KW | M MPH | SNP_9084 | 0.028 | 3 | 87.5 | 82.9 | 90.6 | 7.7 | 13.19 | 0.06 | BM > MM |
| KC | MxRIL | SNP_99055 | 0.024 | 3 | 88.2 | 80.5 | 93.8 | 13.3 | 36.5 | 0.06 | BM > MM |
| KRN | RIL | SNP_77055 | 0.007 | 3 | 92.9 | 88.2 | 229 | 140.8 | 0.92 | 0.07 | BB > MM |
| KRN | MxRIL | SNP_77055 | 0.001 | 3 | 92.9 | 85 | 94 | 9 | 0.65 | 0.13 | BM > MM |
| KC | B pHPH | SNP_45551 | 0.044 | 3 | 141.1 | 135.3 | 147.2 | 11.9 | -0.1 | 0.05 | BB < BM |
| AKW | B HPH | SNP_30953 | 0.004 | 3 | 188.7 | 185 | 191.4 | 6.4 | -0.02 | 0.08 | BB < BM |
| AKW | B pHPH | SNP_30953 | 0.001 | 3 | 188.7 | 185 | 191.4 | 6.4 | -0.06 | 0.08 | BB < BM |
| SDW | B HPH | SNP_84678 | 0.044 | 3 | 217.3 | 80.5 | 229.8 | 149.3 | -0.01 | 0.05 | BB < BM |
| SDW | B MPH | SNP_84678 | 0.01 | 3 | 217.3 | 82.9 | 229.8 | 146.9 | -0.01 | 0.06 | BB < BM |
| SDW | B pMPH | SNP_84678 | 0.016 | 3 | 217.3 | 81.7 | 229.8 | 148.1 | -0.1 | 0.06 | BB < BM |
| KC | RIL | SNP_89298_2 | 0.001 | 4 | 16 | 16 | 19.5 | 3.5 | 62.44 | 0.08 | BB > MM |
| CW | MxRIL | SNP_32823 | 0.001 | 4 | 41.1 | 30.1 | 43.3 | 13.2 | 2.48 | 0.1 | BM > MM |
| CW | RIL | SNP_4623 | 0.001 | 4 | 42.2 | 30.1 | 54.5 | 24.4 | 3.35 | 0.11 | BB > MM |
| CD | BxRIL | SNP_90941 | 0.001 | 4 | 54.5 | 48.2 | 62.2 | 14 | 1.26 | 0.16 | BB > BM |
| CD | MxRIL | SNP_90941 | 0.001 | 4 | 54.5 | 48.2 | 65.6 | 17.4 | 0.84 | 0.12 | BM > MM |
| CD | B HPH | SNP_90941 | 0.001 | 4 | 54.5 | 48.2 | 57.4 | 9.2 | 1.16 | 0.14 | BB > BM |
| CD | B pHPH | SNP_90941 | 0.001 | 4 | 54.5 | 48.2 | 57.4 | 9.2 | 0.04 | 0.14 | BB > BM |
| CW | BxRIL | SNP_90941 | 0.001 | 4 | 54.5 | 48.2 | 62.2 | 14 | 2.86 | 0.09 | BB > BM |
| CW | B HPH | SNP_90941 | 0.001 | 4 | 54.5 | 48.2 | 62.2 | 14 | 2.5 | 0.07 | BB > BM |
| CW | B pHPH | SNP_90941 | 0.003 | 4 | 54.5 | 48.2 | 62.2 | 14 | 0.11 | 0.08 | BB > BM |
| KRN | MxRIL | SNP_81248 | 0.001 | 4 | 54.5 | 30.1 | 62.2 | 32.1 | 0.51 | 0.09 | BM > MM |
| CD | RIL | SNP_82913 | 0.001 | 4 | 57.4 | 48.2 | 65.6 | 17.4 | 1.64 | 0.16 | BB > MM |
| KRN | RIL | SNP_82913 | 0.001 | 4 | 57.4 | 48.2 | 65.6 | 17.4 | 1.32 | 0.15 | BB > MM |
| KRN | M HPH | SNP_82913 | 0.001 | 4 | 57.4 | 54.7 | 65.6 | 10.9 | -0.87 | 0.13 | BM < MM |
| KRN | M pHPH | SNP_82913 | 0.001 | 4 | 57.4 | 54.7 | 65.6 | 10.9 | -0.06 | 0.13 | BM < MM |
| CD | M HPH | SNP_93907 | 0.006 | 4 | 62.2 | 8.1 | 100.3 | 92.2 | -0.79 | 0.07 | BM < MM |
| CD | M pHPH | SNP_93907 | 0.014 | 4 | 62.2 | 8.1 | 100.3 | 92.2 | -0.03 | 0.06 | BM < MM |
| KW | RIL | SNP_93907 | 0.021 | 4 | 62.2 | 16 | 100.3 | 84.3 | 13.82 | 0.06 | BB > MM |
| KRN | BxRIL | SNP_90380 | 0.001 | 4 | 65.6 | 48.2 | 67.5 | 19.3 | 0.75 | 0.11 | BB > BM |
| KRN | B HPH | SNP_90380 | 0.001 | 4 | 65.6 | 48.2 | 67.5 | 19.3 | 0.67 | 0.1 | BB > BM |
| KRN | B pHPH | SNP_90380 | 0.002 | 4 | 65.6 | 48.2 | 67.5 | 19.3 | 0.04 | 0.1 | BB > BM |
| CL | RIL | SNP_49724 | 0.022 | 5 | 44.2 | 42.9 | 55.1 | 12.2 | -10.16 | 0.06 | BB < MM |
| KC | MxRIL | SNP_51496 | 0.011 | 5 | 73.8 | 66.8 | 85.5 | 18.7 | 39.15 | 0.07 | BM > MM |
| KRN | RIL | SNP_11948 | 0.001 | 5 | 73.8 | 70.8 | 76.5 | 5.7 | 1.03 | 0.09 | BB > MM |
| SDW | MxRIL | SNP_18689 | 0.012 | 5 | 73.8 | 69.1 | 91.2 | 22.1 | 0.01 | 0.06 | BM > MM |
| SDW | M HPH | SNP_18689 | 0.032 | 5 | 73.8 | 69.1 | 76.5 | 7.4 | 0.01 | 0.06 | BM > MM |

TABLE 2-continued

Significant QTL for All Traits

| Trait | Analysis | Sig. Marker | P-value[1] | Chr | cM | Confidence Interval[2] Lower cM | Confidence Interval[2] Upper cM | Length (cM) | Effect Size[3] | % Var[4] | Action[5] |
|---|---|---|---|---|---|---|---|---|---|---|---|
| SDW | M MPH | SNP_18689 | 0.029 | 5 | 73.8 | 69.1 | 75.9 | 6.8 | 0.01 | 0.06 | BM > MM |
| SDW | M pHPH | SNP_18689 | 0.046 | 5 | 73.8 | 69.1 | 76.5 | 7.4 | 0.08 | 0.05 | BM > MM |
| KRN | BxRIL | SNP_61221 | 0.012 | 5 | 75.7 | 70.8 | 76.6 | 5.8 | 0.55 | 0.06 | BB > BM |
| KRN | MxRIL | SNP_61221 | 0.006 | 5 | 75.7 | 70.8 | 98.6 | 27.8 | 0.46 | 0.07 | BM > MM |
| CD | MxRIL | SNP_105143 | 0.005 | 5 | 75.9 | 61.5 | 76.6 | 15.1 | 0.63 | 0.07 | BM > MM |
| KW | MxRIL | SNP_84372 | 0.001 | 5 | 81.6 | 72.2 | 85.5 | 13.3 | 15.19 | 0.08 | BM > MM |
| KW | M HPH | SNP_84372 | 0.026 | 5 | 81.6 | 70.8 | 113.8 | 43 | 13.2 | 0.06 | BM > MM |
| KW | M MPH | SNP_84372 | 0.009 | 5 | 81.6 | 70.8 | 105.7 | 34.9 | 13.97 | 0.06 | BM > MM |
| CW | MxRIL | SNP_27764 | 0.01 | 5 | 113.8 | 66.8 | 126 | 59.2 | 2.04 | 0.07 | BM > MM |
| CW | M MPH | SNP_95039 | 0.018 | 5 | 113.8 | 105.7 | 126 | 20.3 | 1.89 | 0.06 | BM > MM |
| CW | BxRIL | SNP_75795 | 0.003 | 6 | 114.2 | 102.3 | 116.4 | 14.1 | −2.58 | 0.07 | BB < BM |
| CW | B HPH | SNP_75795 | 0.018 | 6 | 114.2 | 102.3 | 119.6 | 17.3 | −2.36 | 0.06 | BB < BM |
| CW | B pHPH | SNP_75795 | 0.021 | 6 | 114.2 | 102.3 | 119.6 | 17.3 | −0.1 | 0.06 | BB < BM |
| KRN | RIL | SNP_70805 | 0.003 | 7 | 34.5 | 28.6 | 36 | 7.4 | −0.95 | 0.08 | BB < MM |
| CD | RIL | SNP_43846 | 0.049 | 7 | 42.2 | 22 | 101.2 | 79.2 | −0.97 | 0.05 | BB < MM |
| CD | BxRIL | SNP_98032 | 0.033 | 7 | 43.6 | 22 | 101.2 | 79.2 | −0.77 | 0.05 | BB < BM |
| KC | RIL | SNP_63437 | 0.043 | 7 | 65.5 | 59.4 | 71.6 | 12.2 | −50.81 | 0.05 | BB < MM |
| KRN | BxRIL | SNP_94161 | 0.026 | 7 | 78.3 | 65.5 | 82.1 | 16.6 | −0.54 | 0.06 | BB < BM |
| KRN | B HPH | SNP_94161 | 0.027 | 7 | 78.3 | 65.5 | 82.1 | 16.6 | −0.53 | 0.06 | BB < BM |
| KRN | B pHPH | SNP_94161 | 0.022 | 7 | 78.3 | 65.5 | 82.1 | 16.6 | −0.03 | 0.06 | BB < BM |
| CW | B HPH | SNP_34738 | 0.037 | 7 | 85.8 | 82.1 | 88.5 | 6.4 | −2.18 | 0.05 | BB < BM |
| CW | B pHPH | SNP_34738 | 0.044 | 7 | 85.8 | 82.1 | 88.5 | 6.4 | −0.09 | 0.05 | BB < BM |
| CD | BxRIL | SNP_88270 | 0.02 | 8 | 43.6 | 36.7 | 46.7 | 10 | −0.77 | 0.06 | BB < BM |
| CD | B HPH | SNP_88270 | 0.008 | 8 | 43.6 | 36.7 | 46.7 | 10 | −0.77 | 0.06 | BB < BM |
| CD | B MPH | SNP_88270 | 0.01 | 8 | 43.6 | 36.7 | 46.7 | 10 | −0.58 | 0.06 | BB < BM |
| CD | B pHPH | SNP_88270 | 0.009 | 8 | 43.6 | 36.7 | 46.7 | 10 | −0.03 | 0.06 | BB < BM |
| CD | B pMPH | SNP_88270 | 0.018 | 8 | 43.6 | 36.7 | 46.7 | 10 | −0.02 | 0.05 | BB < BM |
| KRN | MxRIL | SNP_2880 | 0.022 | 8 | 80.9 | 78.7 | 89.8 | 11.1 | 0.44 | 0.06 | BM > MM |
| KRN | M MPH | SNP_36300 | 0.015 | 10 | 1.5 | 0 | 2.8 | 2.8 | −0.32 | 0.06 | BM < MM |
| KRN | M pMPH | SNP_36300 | 0.013 | 10 | 1.5 | 0 | 2.8 | 2.8 | −0.03 | 0.06 | BM < MM |
| CD | BxRIL | SNP_77712 | 0.001 | 10 | 53.4 | 50.2 | 58.1 | 7.9 | −1 | 0.08 | BB < BM |
| CD | B HPH | SNP_77712 | 0.002 | 10 | 53.4 | 50.2 | 58.1 | 7.9 | −0.94 | 0.08 | BB < BM |
| CD | B MPH | SNP_77712 | 0.002 | 10 | 53.4 | 50.2 | 58.1 | 7.9 | −0.69 | 0.07 | BB < BM |
| CD | B pHPH | SNP_77712 | 0.001 | 10 | 53.4 | 50.2 | 58.1 | 7.9 | −0.03 | 0.08 | BB < BM |
| CD | B pHPH | SNP_77712 | 0.004 | 10 | 53.4 | 50.2 | 58.1 | 7.9 | −0.03 | 0.06 | BB < BM |
| CW | BxRIL | SNP_77712 | 0.003 | 10 | 53.4 | 50.2 | 59.5 | 9.3 | −2.59 | 0.07 | BB < BM |
| CW | B HPH | SNP_77712 | 0.003 | 10 | 53.4 | 50.2 | 65.5 | 15.3 | −2.46 | 0.06 | BB < BM |
| CW | B MPH | SNP_77712 | 0.039 | 10 | 53.4 | 50.2 | 71.6 | 21.4 | −2.01 | 0.05 | BB < BM |
| CW | B pHPH | SNP_77712 | 0.007 | 10 | 53.4 | 50.2 | 65.5 | 15.3 | −0.1 | 0.07 | BB < BM |

[1]Genome-wise error rate P-Value;
[2]Confidence interval determined by 1.5 LOD drop-down from significant peak
[3]B73xRIL$_{BB}$ − B73xRIL$_{MM}$ (B73xRIL); Mo17xRIL$_{BB}$ − Mo17xRIL$_{MM}$ (Mo17xRIL), RIL$_{BB}$ − RIL$_{MM}$ (RIL)
[4]Percent variation explained by the QTL
[5]Direction of effect for significant QTL QTL for amount of heterosis were detected where heterozygous lines exhibited more heterosis than the homozygotes (B73xRIL HPH for AKW, SDW, CW, KRN, and CD; Mo17xRIL HPH for CW, SDW). QTL were also detected, however, with homozygous loci favorable over heterozygous loci. Variation of effect size and favorable allele combination suggest that not one single inbred (B73 or Mo17) contributes "more" to heterosis and that heterozygosity per se is not sufficient to explain improved performance of hybrids over inbreds for these particular traits.

Correlation between traits was calculated (Table 3). High correlation between some traits was expected. For example, the total kernel weight per ear would be expected to increase with the total number of kernels on the ear (correlation=0.94). Correlations between seedling dry weight and all other traits are generally low, but might be due to different environments (greenhouse vs. field). However, some correlation is observed for seedling dry weight with cob length and kernel weights.

TABLE 3

Pair-wise Trait Correlation of LS Means for Each Genotype

| | CW | CD | CL | KRN | KW | KC | AKW | SDW |
|---|---|---|---|---|---|---|---|---|
| CW | — | | | | | | | |
| CD | 0.78 | — | | | | | | |
| CL | 0.66 | 0.25 | — | | | | | |
| KRN | 0.46 | 0.73 | −0.17 | — | | | | |
| KW | 0.24 | 0.53 | 0.8 | 0.24 | — | | | |
| KC | 0.84 | 0.64 | 0.69 | 0.46 | 0.94 | — | | |
| AKW | 0.45 | 0.13 | 0.65 | −0.28 | 0.65 | 0.39 | — | |
| SDW | 0.35 | 0.08 | 0.5 | −0.09 | 0.52 | 0.42 | 0.45 | — |

QTL controlling an increase in the trait value and/or in the amount of heterosis observed for the trait have been selected for fine-mapping experiments with the ultimate goal of cloning the gene(s) responsible for the increase in trait value and/or amount of heterosis.

Example 2

Detection of KRN QTL in the Nested Association Mapping (NAM) Population of Maize Genetic Stocks The Maize Nested Association Mapping ("NAM") population was formed by crossing 25 diverse lines to the inbred B73, and then ~200 RILs were created from each of the 25 families. The NAM RIL genetic stocks are publicly available upon request to the Maize Genetics Cooperation Stock Center. During the summer nursery season of two different years, approximately ⅔ of the NAM RILs were planted in 5 plant rows in Ames, Iowa.

Data Collection

All plants were self-pollinated. A photograph was taken of each of the mature ears. KRN data were obtained by manually counting the number of rows on each ear that are visible in the photographs and by subsequently correcting for the rows that are hidden on the far side of each ear. A quality score ("QS") was assigned for each KRN count. The QS ranged from 0 to 5, indicating a confidence level of KRN count that could be collected from the photograph. Four terms were taken into consideration when assigning QS: whether the ear was developed, whether there were missing kernels in any rows, whether there were twisted kernel rows, and whether any partial rows were visible in the photo.

Data were entered into spreadsheets. Quality checks were performed to identify improbable values. Such cases were individually investigated to either confirm the value or correct the error.

Statistical Analysis

Raw KRN counts (X) were transformed using the formula 2x+2 which a pilot study indicated did the best job of converting KRN counts from photograph to numbers that would match counts obtained by determined KRNs directly from ears. These corrected KRN values were used for QTL mapping via each of two methods. The first method ("wmean") used weighted means, in which the KRN count is weighted by the QS to calculate the mean value of a specific RIL. The other method ("trim") makes use of a trimmed weighted mean, in which values with QS</=2 are removed prior to QTL analysis.

Mean estimates of KRN for each NAM RIL were used for subsequent QTL mapping. The QTL mapping was conducted using package R/qtl (Version 1.16-4) and custom scripts were developed to format and visualize the results. A separate QTL mapping analysis was conducted for each of the analyzed NAM populations. Mapping was conducted using the standard interval method (EM algorithm). The significance threshold was determined using 1,000 permutation tests. The confidence intervals were calculated based on the 1.5 LOD dropdown values. Results are set forth in Table 4.

TABLE 4

QTL for KRN

| Population (B73x) | Method | Chr | Sig. Pos. | Sig. Marker | Locus Name | Marker Name | LOD | Threshold | Confidence Interval | C.I. Length |
|---|---|---|---|---|---|---|---|---|---|---|
| CML333 | wmean | 1 | 116.2 | L00401 | L00401 | PZA01216.1 | 3.96 | 3.18 | 94.9-124.2 | 29.3 |
| CML333 | trim | 1 | 116.2 | L004011 | L00401 | PZA01216.1 | 3.86 | 2.94 | 109.9-124.2 | 14.3 |
| I114H | wmean | 1 | 28 | c1.loc28 | L00454 | PZA01497.1 | 3.41 | 3.02 | 20.1-37.8 | 17.7 |
| I114H | wmean | 2 | 69.4 | L01176 | L01176 | PZB00183.4 | 4.54 | 3.02 | 64.2-71.3 | 7.1 |
| I114H | trim | 2 | 70 | c2.loc70 | L00644 | PZA02450.1 | 4.52 | 3.1 | 64.2-71.3 | 7.1 |
| Ky21 | wmean | 2 | 66 | c2.loc66 | L00538 | PZA01993.7 | 3.47 | 3.04 | 54.9-103.7 | 48.8 |
| P39 | wmean | 2 | 54.9 | L01157 | L01157 | PZA03142.5 | 3.41 | 3.09 | 52-85.5 | 33.5 |
| CML322 | wmean | 3 | 55.5 | L00033 | L00951 | zb21.1 | 3.12 | 3.07 | 50.2-68.9 | 18.7 |
| CML322 | trim | 3 | 55.5 | L000331 | L00951 | zb21.1 | 3.15 | 3.1 | 38.3-68.9 | 30.6 |
| Ms71 | wmean | 3 | 54.3 | L00198c | L00198c | PZA00210.1/9 | 5.2 | 2.96 | 50.2-57.6 | 7.4 |
| Ms71 | trim | 3 | 54.3 | L00198c1 | L00198c | PZA00210.1/9 | 5.18 | 2.99 | 50.2-57.6 | 7.4 |
| P39 | wmean | 3 | 52 | c3.loc52 | L00641 | PZA02427.1 | 3.29 | 3.09 | 33.7-90 | 56.3 |
| CML103 | wmean | 4 | 119.8 | L01138 | L01138 | PZA02585.2 | 4.36 | 2.96 | 111.5-135.6 | 24.1 |
| CML103 | trim | 4 | 119.8 | L011381 | L01138 | PZA02585.2 | 3.48 | 2.92 | 110.4-141.1 | 30.7 |
| CML322 | wmean | 4 | 126 | c4.loc126 | L00067 | PHM2100.21 | 3.43 | 3.07 | 111.3-135.6 | 24.3 |
| CML322 | trim | 4 | 126 | c4.loc1261 | L00067 | PHM2100.21 | 4.47 | 3.1 | 116.1-129.3 | 13.2 |
| CML228 | wmean | 4 | 115.2 | L00280 | L00280 | PZA00521.3 | 3.51 | 3.06 | 107.4-136.6 | 29.2 |
| CML333 | trim | 4 | 119.6 | L00133 | L00133 | PHM5599.20 | 4.41 | 2.94 | 115.2-126.9 | 11.7 |
| Ki11 | wmean | 4 | 106 | c4.loc106 | L01014 | PZA00193.2 | 3.41 | 3.02 | 85.2-115.2 | 30 |
| Ms71 | wmean | 4 | 55.2 | L01028 | L01028 | PZA00445.22 | 4.61 | 2.96 | 40.4-69.8 | 29.4 |
| Ms71 | trim | 4 | 55.2 | L010281 | L01028 | PZA00445.22 | 4.6 | 2.99 | 43.9-76.2 | 32.3 |
| Oh43 | wmean | 4 | 118.4 | L00576 | L00576 | PZA02151.3 | 6.96 | 3.05 | 81.9-124.5 | 42.6 |
| Oh43 | trim | 4 | 118.4 | L005761 | L00576 | PZA02151.3 | 7.2 | 3.07 | 81.9-124.5 | 42.6 |
| P39 | wmean | 4 | 52 | c4.loc52 | L00042 | PHM15427.11 | 3.36 | 3.09 | 33.9-135.6 | 101.7 |
| P39 | trim | 4 | 52 | c4.loc521 | L00042 | PHM15427.11 | 3.51 | 3.11 | 33.9-135.6 | 101.7 |
| Tx303 | trim | 4 | 114 | c4.loc114 | L00280 | PZA00521.3 | 3.72 | 2.96 | 60.6-124.5 | 63.9 |
| B97 | wmean | 5 | 60.6 | L00589 | L00589 | PZA02207.1 | 4.04 | 3.09 | 47-78.4 | 31.4 |
| B97 | trim | 5 | 53.9 | L00134 | L00134 | PHM565.31 | 3.65 | 3.08 | 47-78.4 | 31.4 |
| I114H | wmean | 5 | 47 | c5.loc47 | L00835 | PZA03578.1 | 5.07 | 3.02 | 41.5-80.7 | 39.2 |
| I114H | trim | 5 | 47 | c5.loc471 | L00835 | PZA03578.1 | 5.02 | 3.1 | 41.5-81.7 | 40.2 |
| Oh43 | wmean | 5 | 83.4 | L00221 | L00221 | PZA00300.14 | 4.89 | 3.05 | 81.7-87.2 | 5.5 |
| Oh43 | trim | 5 | 83.4 | L002211 | L00221 | PZA00300.14 | 4.76 | 3.07 | 78.4-87.2 | 8.8 |
| Tx303 | wmean | 5 | 73 | c5.loc73 | L00171 | PZA00067.10 | 4.03 | 3.09 | 57.3-87.2 | 29.9 |
| Tx303 | trim | 5 | 57.6 | L00110 | L00461 | PZA01563.1 | 3.5 | 2.96 | 50.8-87.2 | 36.4 |
| CML333 | wmean | 10 | 51 | c10.loc51 | L01041 | PZA00647.9 | 6.44 | 3.18 | 44.8-61.6 | 16.8 |
| CML333 | trim | 10 | 50 | c10.loc50 | L00367 | PZA01005.1 | 5.2 | 2.94 | 44.8-75.4 | 30.6 |

Notes:
wmean, weighted mean of the KRN count;
trim, trimmed mean of the KRN count.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A method for determining an ear productivity trait in maize, said method comprising:

isolating genomic DNA from a maize plant, germplasm, pollen, or seed;

analyzing genomic DNA from the maize plant, germplasm, pollen, or seed for the presence of a molecular marker linked to a quantitative trait locus (QTL) associated with an ear productivity trait in maize, wherein the molecular marker is selected from the group consisting of L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.locl 14, L00589, L00134, c 5.loc47, c 5.loc471, L00221, L002211, c 5.loc73, L00110, c10.loc51, c10.loc50, SNP_35511, SNP_98111, SNP_23951, SNP_79262, SNP_19249, SNP_9084, SNP_99055, SNP_77055, SNP_45551, SNP_30953, SNP_84678, SNP_89298_2, SNP_32823, SNP_4623, SNP_90941, SNP_81248, SNP_82913, SNP_93907, SNP_90380, SNP_49724, SNP_51496, SNP_11948, SNP_18689, SNP_61221, SNP_105143, SNP_84372, SNP_27764, SNP_95039, SNP_75795, SNP_70805, SNP_43846, SNP_98032, SNP_63437, SNP_94161, SNP_34738, SNP_88270, SNP_2880, SNP_36300, and SNP_77712;

detecting at least one molecular marker that is associated with an ear productivity trait; and selecting a maize plant having the ear productivity trait.

2. The method according to claim 1, wherein the ear productivity trait is kernel row number (KRN) and the marker is selected from the group consisting of L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.locl 14, L00589, L00134, c 5.loc47, c 5.loc471, L00221, L002211, c 5.loc73, L00110, c10.loc51, c10.loc50, SNP_77055, SNP_81248, SNP_82913, SNP_90380, SNP_11948, SNP_61221, SNP_70805, SNP_94161, SNP_2880, and SNP_36300.

3. The method according to claim 1, wherein the ear productivity trait is cob weight (CW) and the marker is selected from the group consisting of SNP_98111, SNP_32823, SNP_4623, SNP_90941, SNP_27764, SNP_95039, SNP_75795, SNP_34738, and SNP_77712.

4. The method according to claim 1, wherein the ear productivity trait is cob diameter (CD) and the marker is selected from the group consisting of SNP_90941, SNP_82913, SNP_93907, SNP_105143, SNP_43846, SNP_98032, SNP_88270, and SNP_77712.

5. The method according to claim 1, wherein the ear productivity trait is cob length (CL) and the marker is selected from the group consisting of SNP_35511, SNP_19249, and SNP_49724.

6. The method according to claim 1, wherein the ear productivity trait is kernel weight (KW) and the marker is selected from the group consisting of SNP__79262, SNP__9084, SNP__93907, and SNP__84372.

7. The method according to claim 1, wherein the ear productivity trait is kernel count (KC) and the marker is selected from the group consisting of SNP_9084, SNP__99055, SNP__45551, SNP__89298_2, SNP__51496, and SNP__63437.

8. The method of claim 1, wherein said selecting occurs as part of a breeding program to improve a maize variety's ear productivity.

9. The method of claim 8, wherein the breeding program comprises crossing, making hybrids, backcrossing, self-crossing, double haploid breeding, and/or combinations thereof.

10. A method for producing a maize line having a desired ear productivity trait, said method comprising:

providing a first maize line having a molecular marker selected from the group consisting of L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP__35511, SNP__98111, SNP__23951, SNP__79262, SNP__19249, SNP__9084, SNP__99055, SNP__77055, SNP__45551, SNP__30953, SNP__84678, SNP__89298_2, SNP__32823, SNP__4623, SNP__90941, SNP__81248, SNP__82913, SNP__93907, SNP__90380, SNP__49724, SNP__51496, SNP__11948, SNP__18689, SNP__61221, SNP__105143, SNP__84372, SNP__27764, SNP__95039, SNP__75795, SNP__70805, SNP__43846, SNP__98032, SNP__63437, SNP__94161, SNP__34738, SNP__88270, SNP__2880, SNP__36300, and SNP__77712, the molecular marker mapping to a genomic locus associated with a desired ear productivity trait;

introgressing the desired ear productivity trait into a maize line; and selecting a maize line having the desired ear productivity trait.

11. The method according to claim 10, wherein the ear productivity trait is kernel row number (KRN) and the marker is selected from the group consisting of L00401, L004011, c 1.loc28, L01176, c 2.loc70, c 2.loc66, L01157, L00033, L000331, L00198c, L00198c1, c 3.loc52, L01138, L011381, c 4.loc126, c 4.loc1261, L00280, L00133, c 4.loc106, L01028, L010281, L00576, L005761, c 4.loc52, c 4.loc521, c 4.loc114, L00589, L00134, c 5.loc47, c 5.loc471, L00221, L002211, c 5.loc73, L00110, c10.loc51, c10.loc50, SNP__77055, SNP__81248, SNP__82913, SNP__90380, SNP__11948, SNP__61221, SNP__70805, SNP__94161, SNP__2880, and SNP__36300.

12. The method according to claim 10, wherein the ear productivity trait is cob weight (CW) and the marker is selected from the group consisting of SNP__98111, SNP__32823, SNP__4623, SNP__90941, SNP__27764, SNP__95039, SNP__75795, SNP__34738, and SNP__77712.

13. The method according to claim 10, wherein the ear productivity trait is cob diameter (CD) and the marker is selected from the group consisting of SNP__90941, SNP__82913, SNP__93907, SNP__105143, SNP__43846, SNP__98032, SNP__88270, and SNP__77712.

14. The method according to claim 10, wherein the ear productivity trait is cob length (CL) and the marker is selected from the group consisting of SNP__35511, SNP__19249, and SNP__49724.

15. The method according to claim 10, wherein the ear productivity trait is kernel weight (KW) and the marker is selected from the group consisting of SNP__79262, SNP__9084, SNP__93907, and SNP__84372.

16. The method according to claim 10, wherein the ear productivity trait is kernel count (KC) and the marker is selected from the group consisting of SNP_9084, SNP__99055, SNP__45551, SNP__89298_2, SNP__51496, and SNP__63437.

* * * * *